(12) United States Patent  (10) Patent No.: US 8,409,568 B2
Gao et al.  (45) Date of Patent: Apr. 2, 2013

(54) MUTANT ANTIBODY FC DOMAINS AND FUSION PROTEINS THEREOF

(75) Inventors: Changshou Gao, Potomac, MD (US); Herren Wu, Boyds, MD (US)

(73) Assignee: MedImmune, LLC, Gaithersburg, MD (US)

( * ) Notice: Subject to any disclaimer, the term of this patent is extended or adjusted under 35 U.S.C. 154(b) by 0 days.

(21) Appl. No.: 12/837,208

(22) Filed: Jul. 15, 2010

(65) Prior Publication Data

US 2010/0331208 A1  Dec. 30, 2010

Related U.S. Application Data

(62) Division of application No. 11/580,005, filed on Oct. 13, 2006, now Pat. No. 7,790,655.

(60) Provisional application No. 60/726,161, filed on Oct. 14, 2005.

(51) Int. Cl.
*C07K 16/00* (2006.01)
*G01N 33/563* (2006.01)
*A61K 39/395* (2006.01)

(52) U.S. Cl. ............... 424/130.1; 424/133.1; 424/134.1; 424/141.1; 424/143.1; 424/179.1; 436/512

(58) Field of Classification Search ............... 424/133.1, 424/130.1, 134.1, 141.1, 143.1, 179.1; 436/512
See application file for complete search history.

(56) References Cited

U.S. PATENT DOCUMENTS

| | | | |
|---|---|---|---|
| 5,624,821 A | 4/1997 | Winter et al. | |
| 5,648,260 A | 7/1997 | Winter et al. | |
| 5,677,425 A | 10/1997 | Bodmer et al. | |
| 5,869,046 A | 2/1999 | Presta | |
| 5,885,573 A | 3/1999 | Bluestone | |
| 5,968,742 A | 10/1999 | Bandman et al. | |
| 6,027,910 A | 2/2000 | Klis et al. | |
| 6,121,022 A | 9/2000 | Presta et al. | |
| 6,165,745 A | 12/2000 | Ward et al. | |
| 6,194,551 B1 | 2/2001 | Idusogie et al. | |
| 6,214,613 B1 | 4/2001 | Higuchi | |
| 6,277,375 B1 | 8/2001 | Ward | |
| 6,737,056 B1 | 5/2004 | Presta | |
| 6,821,505 B2 | 11/2004 | Ward | |
| 7,074,602 B2 * | 7/2006 | Cho et al. ...................... | 435/115 |
| 7,083,784 B2 | 8/2006 | Dall'Acqua | |
| 7,217,797 B2 | 5/2007 | Hinton | |
| 7,247,302 B1 | 7/2007 | Rosok | |
| 7,416,726 B2 | 8/2008 | Ravetch | |

(Continued)

FOREIGN PATENT DOCUMENTS

WO  WO 94/29351  12/1994
WO  WO-98-05787  2/1998

(Continued)

OTHER PUBLICATIONS

Alegre, Maria-Luisa et al., 1994, "A Non-Activating "Humanized" Anti-CD3 Monoclonal Antibody Retains Immunosuppressive Properties In Vivo", Transplantation, 57:1537-1543.

(Continued)

*Primary Examiner* — Christopher M Gross
*Assistant Examiner* — Jeremy C Flinders
(74) *Attorney, Agent, or Firm* — MedImmune, LLC

(57) ABSTRACT

The present invention relates to a viral vector encoding for a library of antibodies or antibody fragments that are displayed on the cell membrane when expressed in a cell. The present invention provides cells comprising the viral vector nucleic acids and methods of screening the libraries for antibodies or antibody fragments with desired characteristics.

12 Claims, 17 Drawing Sheets

U.S. PATENT DOCUMENTS

Figure 1A:
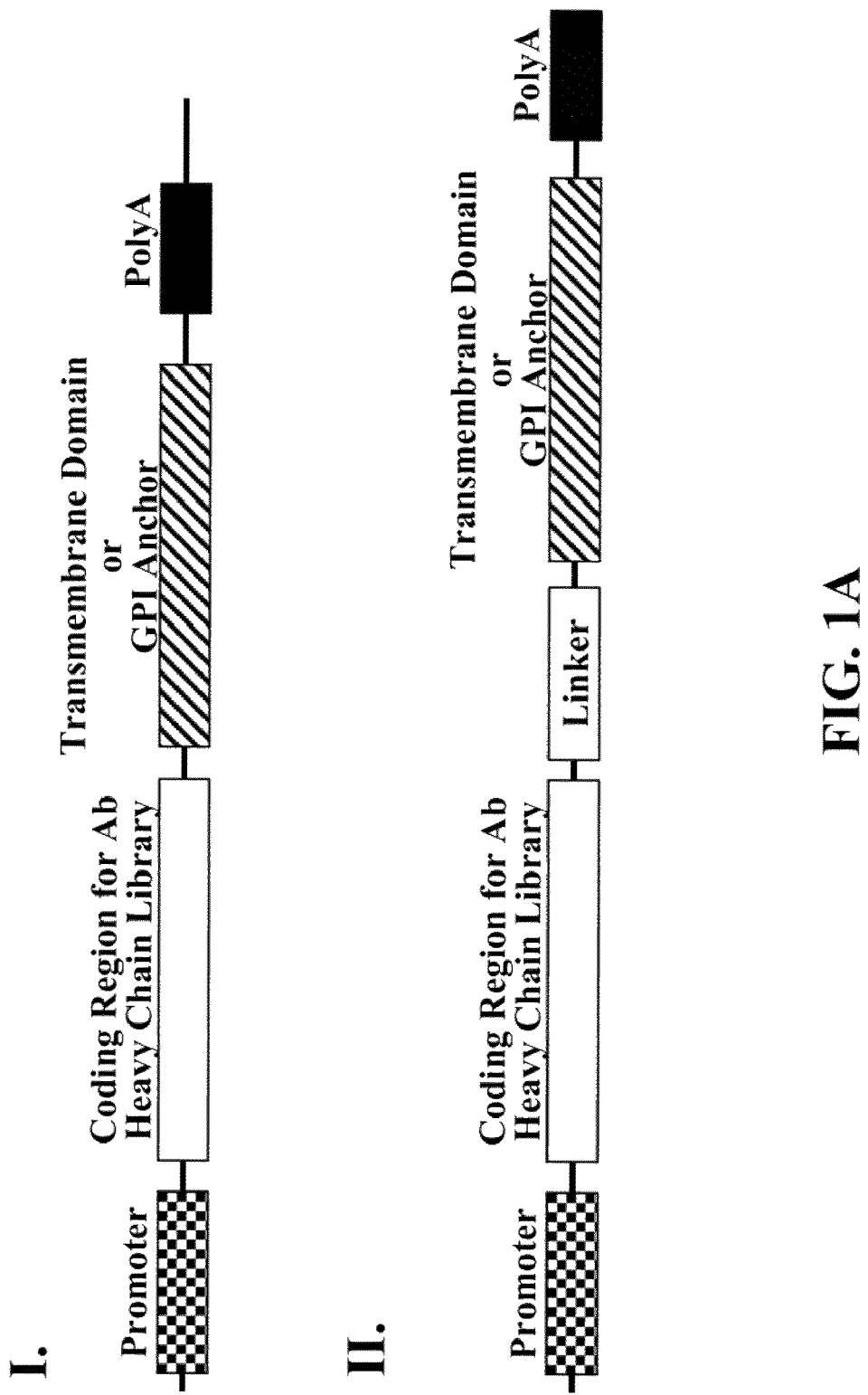

| | | |
|---|---|---|
| 7,597,889 B1 | 10/2009 | Armour |
| 2001/0036459 A1 | 11/2001 | Ravetch |
| 2002/0123057 A1 | 9/2002 | Zauderer et al. |
| 2003/0157108 A1 | 8/2003 | Presta |
| 2003/0186374 A1 | 10/2003 | Hufton et al. |
| 2003/0232395 A1 | 12/2003 | Hufton |
| 2004/0002587 A1 | 1/2004 | Watkins et al. |
| 2004/0132101 A1 | 7/2004 | Lazar |
| 2005/0037000 A1 | 2/2005 | Stavenhagen |
| 2005/0048578 A1 | 3/2005 | Zhang |
| 2005/0054832 A1 | 3/2005 | Lazar et al. |
| 2005/0064514 A1 | 3/2005 | Stavenhagen |
| 2005/0152894 A1 | 7/2005 | Krummen |
| 2006/0024298 A1 | 2/2006 | Lazar |
| 2006/0039904 A1 | 2/2006 | Wu et al. |
| 2006/0040325 A1 | 2/2006 | Wu et al. |
| 2006/0067930 A1 | 3/2006 | Adams |
| 2006/0074225 A1 | 4/2006 | Chamberlain |
| 2006/0134105 A1 | 6/2006 | Lazar |
| 2006/0173170 A1 | 8/2006 | Chamberlain |
| 2006/0205926 A1 | 9/2006 | Ross et al. |
| 2006/0235208 A1 | 10/2006 | Lazar et al. |
| 2006/0275283 A1 | 12/2006 | van Vlijmen |
| 2007/0148164 A1 | 6/2007 | Farrington |
| 2007/0148167 A1 | 6/2007 | Strohl |
| 2007/0224188 A1 | 9/2007 | Allan |
| 2008/0089892 A1 | 4/2008 | Allan |

FOREIGN PATENT DOCUMENTS

| | | |
|---|---|---|
| WO | WO 98/23289 | 6/1998 |
| WO | WO 99/54494 | 10/1999 |
| WO | WO 99/58572 | 11/1999 |
| WO | WO 01/32894 A1 | 5/2001 |
| WO | WO 01/58957 | 8/2001 |
| WO | WO 01/98352 A2 | 12/2001 |
| WO | WO 03/017944 A2 | 3/2003 |
| WO | WO 03/034275 A2 | 4/2003 |
| WO | WO 03/074679 | 9/2003 |
| WO | WO 03/104415 | 12/2003 |
| WO | WO 2004/016750 | 2/2004 |
| WO | WO 2004/029207 | 4/2004 |
| WO | WO 2004/035752 | 4/2004 |
| WO | WO 2004/099249 | 11/2004 |
| WO | WO 2005/000899 | 1/2005 |
| WO | WO 2005/040217 | 5/2005 |
| WO | WO 2005/047327 | 5/2005 |
| WO | WO 2005/063815 | 7/2005 |
| WO | WO 2005/063817 A2 | 7/2005 |
| WO | WO 2005/070963 | 8/2005 |
| WO | WO 2005/092925 | 10/2005 |
| WO | WO 2006/022944 A2 | 3/2006 |
| WO | WO 2006/053301 | 5/2006 |
| WO | WO 2006/076594 | 7/2006 |

OTHER PUBLICATIONS

Ahmed, Nuzhat et al., 2002, "$\alpha_v\beta_6$ Integrin-A Marker for the Malignant Potential of Epithelial Ovarian Cancer", The Journal of Histochemistry & Cytochemistry, 50(10):1371-1379.

Ames, Robert S., 1995, "Conversion of murine Fabs isolated from a combinatorial phage display library to full length immunoglobulins", Journal of Immunological Methods, 184:177-186.

Anderson, Stacie M., et al., 1996, "Intercellular transfer of a glycosylphosphatidylinositol (GIP)-linked protein: Release and uptake of CD4-GPI from recombinant adeno-associated virus-transduced HeLa cells", Proc. Natl. Acad. Sci. USA, 93: 5894-5898.

Armour, Kathryn L., et al., 1999, "Recombinant human IgG molecules lacking Fcγ receptor 1 bnding and monocyte triggering activities", eur. J. Immunol, 29:2613-2624.

Boder, Eric T. et al., 2000, "Yeast Surface Display for Directed Evolution of Protein Expression, Affinity, and Stability", 328:430-444.

Chesnut, Jonathan D. et al., 1996, "Selective isolation of transiently transfected cells from a mammalian cell population with vectors expressing a membrane anchored single-chain antibody", Journal of Immunological Methods 193:17-27.

Chou, Wan-Chih et al., 1999, "Expression of Chimeric Monomer and Dimer Proteins on the Plasma Membrane of Mammalian Cells", Biotechnology and Bioengineering, 65(2):161-169.

Griffin, Matthew D. et al., 2001, "Development and applications of surface-linked single chain antibodies against T-cell antigens", Journal of Immunological Methods, 248:77-90.

Higuchi, Kazuo et al., 1997, "Cell display library for gene cloning of variable regions of human antibodies to hepatitis B surface antigen", Journal of Immunological Methods, 202:193-204.

Lee, Chingwei V. et al., 2004, "Bivalent antibody phage display mimics natural immunoglobulin", Journal of Immunological Methods, 284:119-132.

Mielke, Christian et al., 2000, "Stabilized, long-term expression of heterodimeric proteins from tricistronic mRNA", Gene, 254:1-8.

Akamatsu, Yoshiko et al., 2007, "Whole IgG surface display on mammalian cells: Application to isolation of neutralizing chicken monoclonal anti-IL-12 antibodies", Journal of Immunological Methods, 327:40-52.

Beerli, Roger R. et al., 2008, "Isolation of human monoclonal antibodies by mammalian cell display", Proceedings of the National Acadamy of Sciences, 105(38):14336-14341.

Boder, Eric T. et al., 1997, "Y east Surface display for screening combinatorial polypeptide libraries", Nature Biotechnology, 15:553-557.

Chen, Liyan et al., 2003, "Expression of a prototypic anti-colorectal cancer polyclonal antibody library in mammalian cells", Immunology Letters, 88:135-140.

Hoogenboom, Hennie R., 2005, "Selecting and screening recombinant antibody libraries", Nature Biotechnology, 23(9):1105-1116.

Ho, Mitchell et al., 2006, "Isolation of anti-CD22 Fv with high affinity by Fv display on human cells", Proceedings of the National Acadamy of Sciences, 103(25):9637-9642.

Ho, Mitchell et al., 2007, Corrections and Retraction: "Isolation of anti-CD22 Fv with high affinity by Fv display on human cells", Proceedings of the National Acadamy of Sciences, 104(36):14543.

International Search Report corresponding PCT/US06/40366 dated May 24, 2007.

Koller, Daniel et al., 2001, "A high-throughput alphavirus-based expression cloning system for mammalian cells", Nature Biotechnology, 19:851-855.

Supplementary European Search Report for corresponding EP Application No. 06816992 dated Feb. 11, 2011.

Yau, Kerrm Y.F. et al., 2003, "Emerging trends in the synthesis and improvement of hapten-specific recombinant antibodies", Biotechnology Advances, 21:599-637.

Alegre, M. L., et al. "A Non-Activating "Humanized" Anti-CD3 Monoclonal Antibody Retains Immunosuppressive Properties in Vivo." *Transplantation* (1994) 57: 1537-43.

Armour, K. L., et al. "Recombinant Human IgG Molecules Lacking Fcgamma Receptor I Binding and Monocyte Triggering Activities." *Eur.J.Immunol.* (1999) 29: 2613-24.

Bastida-Corcuera et al., "Differential complement activation by bovine IgG2 allotypes." *Vet Immunol Immunopathol* (1999) 71:115-123.

Brekke et al., "Activation of complement by an IgG molecule without a genetic hinge." *Nature* (1993) 363:628-30.

Brekke et al., "The structural requirements for complement activation by IgG: does it hinge on the hinge?" *Immunol. Today* (1995) 16:85-90.

Bruggemann, M., et al. "Comparison of the Effector Functions of Human Immunoglobulins using a Matched Set of Chimeric Antibodies." *J.Exp.Med.* (1987) 166: 1351-61.

Clynes, R., et al. "Fc Receptors are Required in Passive and Active Immunity to Melanoma." *Proc.Natl.Acad.Sci.U.S.A.* (1998) 95: 652-6.

Coloma et al., "The Hinge as a Is Required for Spacer Contributes Function of IgG" *J. Immunol.* (1997)158:733-40.

Dall'Acqua, William, et al., 1998, "Contribution of domain interface residues to the stability of antibody CH3 domain homodimers", Biochemistry, 37(26):9266-73.

Dall'Acqua, W. F., et al. "Increasing the Affinity of a Human IgG1 for the Neonatal Fc Receptor: Biological Consequences." J. Immunol. (2002) 169:5171-80.

Dall'Acqua, W. F., et al. "Modulation of the Effector Functions of a Human IgG1 through Engineering of its Hinge Region." *J.Immunol.* (2006) 177: 1129-38.

Dall'Acqua, W.F., et al. "Properties of human IgG1s engineered for enhanced binding to the neonatal Fc Receptor (fcRn)." *JBC* (2006) 281:23514-23524.

Dangl et al., "Segmental flexibility and complement fixation of genetically engineered chimeric human, rabbit and mouse antibodies." *EMBO* (1988) 71989-94.

Duncan, A. R., et al. "Localization of the Binding Site for the Human High-Affinity Fc Receptor on IgG." *Nature* (1988) 332: 563-4.

Ghetie, V., et al. "Increasing the Serum Persistence of an IgG Fragment by Random Mutagenesis." *Nat.Biotechnol.* (1997) 15: 637-40.

Gillies and Wesolowsi, "Antigen binding and biological activities of engineered mutant chimeric antibodies with human tumor speciicities." *Hum. Antibod. Hybridomas* (1990) 1: 47-54.

Hutchins, J. T., et al. "Improved Biodistribution, Tumor Targeting, and Reduced Immunogenicity in Mice with a Gamma 4 Variant of Campath-1H." *Proc.Natl.Acad.Sci.U.S.A.* (1995) 92: 11980-4.

Idusogie, E. E., et al. "Engineered Antibodies with Increased Activity to Recruit Complement." *J.Immunol.* (2001) 166: 2571-5.

Idusogie, E. E., et al. "Mapping of the C1q Binding Site on Rituxan, a Chimeric Antibody with a Human IgG1 Fc." *J.Immunol.* (2000) 164: 4178-84.

Jefferis, R., et al. "Interaction Sites on Human IgG-Fc for FcgammaR: Current Models." *Immunol.Lett.* (2002) 82: 57-65.

Jefferis, R., et al. "Modulation of Fc(Gamma)R and Human Complement Activation by IgG3-Core Oligosaccharide Interactions." *Immunol.Lett.* (1996) 54: 101-4.

Jefferis, R., et al. "Recognition Sites on Human IgG for Fc Gamma Receptors: The Role of Glycosylation." *Immunol.Lett.* (1995) 44: 111-7.

Kim, J-K, et al. "Mapping the site on human IgG for binding of the MHC class I-related receptor, FcRn" *E. J of Immunol.* (1999) 26:2819-2825.

Klein et al., "Expression of biological effector functions by immunoglobulin G molecules lacking the hinge region." *Proc Natl Acad Sci USA* (1981) 78: 524-8.

Lund, J., et al. "Multiple Interactions of IgG with its Core Oligosaccharide can Modulate Recognition by Complement and Human Fc Gamma Receptor I and Influence the Synthesis of its Oligosaccharide Chains." *J.Immunol.* (1996) 157: 4963-9.

Lund, J., et al. "Oligosaccharide-Protein Interactions in IgG can Modulate Recognition by Fc Gamma Receptors." *FASEB J.* (1995) 9: 115-9.

Lund, J., et al. "Multiple Binding Sites on the CH2 Domain of IgG for Mouse Fc Gamma R11." *Mol.Immunol.* (1992) 29: 53-9.

Lund, J., et al. "Human Fc Gamma RI and Fc Gamma RII Interact with Distinct but Overlapping Sites on Human IgG." *J.Immunol.* (1991) 147: 2657-62.

Oi, T., et al. "Correlation between segmental flexibility and effector function of antibodies." *Nature* (1984) 307: 136-40.

Patel, A. K., et al. "An Improved Assay for Antibody Dependent Cellular Cytotoxicity Based on Time Resolved Fluorometry." *J.Immunol.Methods* (1995) 184: 29-38.

Stefka, P.B., et al. "Enhanced half-life of genetically engineered human IgG1 antibodies in a humanized FcRn mouse model: potential application in humorally mediated autoimmune disease." *Intern. Immunol.* (2006) 18:1759-69.

Presta, L. G., et al. "Engineering Therapeutic Antibodies for Improved Function." *Biochem.Soc.Trans.* (2002) 30: 487-90.

Radaev, S., et al. "Recognition of immunoglobulins by Fcγ receptors." *Mol. Immunol.* (2001) 38:1073-83.

Reddy, M. P., et al. "Elimination of Fc Receptor-Dependent Effector Functions of a Modified IgG4 Monoclonal Antibody to Human CD4." *J.Immunol.* (2000) 164: 1925-33.

Redpath, S., et al. "Activation of complement by human IgG1 and IgG3 antibodies against the human leucocyte antigen CD52." Immunology (1998) 93:595-600.

Redpath, S., et al. "The Influence of the Hinge Region Length in Binding of Human IgG to Human Fcγ Receptors." Human Immunol. (1998) 59:720-27.

Shields, R. L., et al. "Lack of Fucose on Human IgG1 N-Linked Oligosaccharide Improves Binding to Human Fcgamma RIII and Antibody-Dependent Cellular Toxicity." *J.Biol.Chem.* (2002) 277: 26733-40.

Shields, R. L., et al. "High Resolution Mapping of the Binding Site on Human IgG1 for Fc Gamma RI, Fc Gamma RII, Fc Gamma RIII, and FcRn and Design of IgG1 Variants with Improved Binding to the Fc Gamma R." *J.Biol.Chem.* (2001) 276: 6591-604.

Shopes, B., "A Genetically engineered human IgG with limited flexibility full initiates cytolysis via complement." *Mol. Immunol.* (1993) 30: 603-09.

Stevenson G., et al. "Conjugation of Human Fcγ in Closed-Hinge or Open Hinge Configuration to Fab' γ and Analogous Ligands." *J. Immunol.* (1997) 158:2242-50.

Tan, L., et al. "Influence of the hinge region on complement activation, C1q binding, and segmental flexibility in chimeric human immunoglobulins." *Proc.Natl.Acad.Sci.U.S.A.* (1990) 87:162-66.

Wilkinson, R. W., et al. "Antibody-Dependent Cell-Mediated Cytotoxicity: A Flow Cytometry-Based Assay using Fluorophores." *J.Immunol.Methods* (2001) 258: 183-91.

Wisecarver, J., et al. "A Method for Determination of Antibody-Dependent Cellular Cytotoxicity (ADCC) of Human Peripheral Mononuclear Cells." *J.Immunol.Methods* (1985) 79: 277-82.

Xu, D., et al. "In Vitro Characterization of Five Humanized OKT3 Effector Function Variant Antibodies." *Cell.Immunol.* (2000) 200: 16-26.

\* cited by examiner

MUTANT ANTIBODY FC DOMAINS AND FUSION PROTEINS THEREOF

1. CROSS REFERENCE TO RELATED APPLICATIONS

This application is a divisional of U.S. application Ser. No. 11/580,005 filed on Oct. 13, 2006, now U.S. Pat. No. 7,790,655, said application Ser. No. 11/580,005 claims the benefit under 35 U.S.C. §119(e) of U.S. Provisional Application No. 60/726,161, filed Oct. 14, 2005. Each of the above listed applications is incorporated by reference herein in its entirety for all purposes.

Reference to the Sequence Listing

This application incorporates by reference a Sequence Listing submitted with this application as text file entitled "AE710US.ST25.txt" created on Oct. 12, 2006 and having a size of 32 kilobytes.

2. FIELD OF THE INVENTION

The present invention provides a method for displaying antibodies or antibody fragments on the surface of a cell membrane; a method for producing a library of cells displaying antibodies or antibody fragments on the cell surface; cells expressing a library of antibodies or antibody fragments on the cell surface; viral vector libraries for expressing a library of antibodies or antibody fragments on a cell membrane; a method of screening for antibodies or antibody fragments that bind to a particular antigen; a method of screening for antibodies or antibody fragments with improved and/or altered binding characteristics; a method of screening cells expressing and displaying on their cell surface antibodies or antibody fragments that bind to a particular antigen; a method of screening cells expressing and displaying on their cell surface antibodies or antibody fragments with improved and/or altered binding characteristics; and related kits. The present invention also provides Fc variants with altered ligand binding (e.g., FcγR binding) and/or altered effector function (e.g., ADCC activity).

3. BACKGROUND OF THE INVENTION

Antibodies are immunological proteins that bind a specific antigen. In most mammals, including humans and mice, antibodies are constructed from paired heavy and light polypeptide chains. Each chain is made up of two distinct regions, referred to as the variable (Fv) and constant (Fc) regions. The light and heavy chain Fv regions contain the antigen binding determinants of the molecule and are responsible for binding the target antigen. The Fc regions define the class (or isotype) of antibody (IgG for example) and are responsible for binding a number of Fc receptors and other Fc ligands, imparting an array of important functional capabilities referred to as effector functions. Several key features of antibodies including but not limited to, specificity for target, ability to mediate immune effector mechanisms, and long half-life in serum, make antibodies powerful therapeutics. Recombinant screening methods for isolating antibodies with a desired binding specificity have been developed. For example, it is possible to generate large expression libraries of binding molecules using combinatorial recombinant DNA technologies. This is especially true in the field of antibody engineering, where recombinant antibody libraries routinely contain more then $10^9$ unique clones. The availability of large libraries of binding molecules has provided a source of binders to most any ligand.

Surface display libraries allow for the enrichment of specific binding clones by subjecting the organism displaying the binding molecule (e.g., phage and yeast) to successive rounds of selection (e.g., panning; for reviews see, Trends Biotechnol 9: 408-414; Coomber, et al., 2002, Methods Mol Biol 178: 133-45, Kretzschmar et al., 2002, Curr Opin Biotechol 13: 598-602; Fernandez-Gacio, et al., 2003, Bioorg Med Chem Lett. 13:213-216; Lee et al., 2003, Trends Biotechnol 21: 45-52; and Kondo, et al., 2004, Appl Microbiol Biotechnol 64: 28-40). In particular, advances in phage display antibody libraries have made them an attractive alternative to screening conventional hybridoma-derived monoclonal antibodies. Phage display library screening is advantageous over some other screening methods due to the vast number of different polypeptides (typically exceeding $10^9$) that can be contained in a single phage display library. This allows for the screening of a highly diverse library in a single screening step.

Display of small peptides or single chain proteins on phage can be advantageous as long as intracellular processing or post-translational modification (of which phage or prokaryotic hosts are not capable) is not necessary or desired. For example, effective display of a heterologous polypeptide may require various post-translational modifications, intracellular structures, and a compliment of specialized enzymes and chaperone proteins that are necessary to transport, to glycosylate, to conform, to assemble, and to anchor the display polypeptide properly on the surface of the host cell; however, none of these processes can be accomplished by bacteriophage or prokaryotic cell processes. Furthermore, prokaryotic cells do not always efficiently express functional eukaryotic proteins.

Bacterial and bacteriophage display systems are also limited by the small capacity of the display system, and as such, are more suited for the display of small peptides as are the recently developed methods for surface display of small peptides on mammalian cells (see, e.g., Wolkowicz, et al., 2005, J. Biol. Chem., 280: 15195-15201). As a result bacteriophage and mammalian antibody display libraries and methods require that only a fragment of an antibody be displayed on the surface. If the purpose is to discover "whole" antibodies then the antibody fragments must be cloned into a whole antibody. Not only does this add an extra step, but also many antibody fragments have decreased affinity for an antigen when converted to a whole antibody and such libraries. Furthermore, such methods cannot be used to examine the binding of other antibody domains such as the Fc region to antibody receptors (e.g., Fc receptors) or other Fc ligands.

Whole antibody cell surface display systems have been developed for some eukaryotic cells, such as yeast (see, e.g., Boder and Wittrup, 2000, Methods in Enzymology, 328:430-444), but the develop of whole antibody display on mammalian cells lags behind. Furthermore, the size of the libraries, which can be generated in these systems, is limited. Since the chance of isolating antibodies with the desired binding properties from an antibody library is proportional to the size and diversity of the library there is a need for methods to generate large and diverse libraries. This is particularly important if you want to build a naive antibody library for antibody discovery, for example from un-immunized donors. Currently, to build the library size larger than $10^8$ members is a challenge to any eukaryotic cell display technology by using conventional transfection tools such as transient transfection or electroporation. Thus, there is a need for antibody cell surface display libraries and library screening methods for eukaryotic cells, in particular mammalian cells, which maintain a large diversity, but eliminate any of the issues discussed supra. Such a system would be particularly useful for the identification of antibody variants in regions outside of the variable domain such as in the Fc region. Modifications, including amino acid deletions, substitutions and additions, of the Fc region have been demonstrated to alter the binding of the Fc region to its ligands and/or receptors resulting in a concomitant change in effector function (see, e.g., (Shields et al., 2001, *J Biol Chem* 276:6591-6604 and Presta et al., 2002, *Biochem Soc Trans* 30:487-490 and U.S. Patent Publication 2004/0132101). Thus, by modifying the Fc region the therapeutic effectiveness of Fc containing molecules can be improved. A system for whole antibody cell surface display on mammalian cells would facilitate the rapid identification of antibodies with modified Fc regions having altered effector function.

Citation or discussion of a reference herein shall not be construed as an admission that such is prior art to the present invention.

4. SUMMARY OF THE INVENTION

The present invention relates to a recombinant antibody or fragment thereof that is displayed on the extracellular surface of the cell membrane, referred to herein as an "antibody of the invention" and like terms. In certain embodiments, a recombinant antibody of the invention comprises a heavy chain or a fragment thereof and optionally a light chain or a fragment thereof, wherein either the heavy chain or light chain further comprises an amino acid sequence that targets the antibody or fragment thereof to the cell surface. In one embodiment, a recombinant antibody of the invention comprises a full length heavy chain having an amino acid sequence that targets the antibody to the cell surface wherein said amino acid sequence is fused to the C terminus of said heavy chain and may further comprise a full length light chain. In still another embodiment, a recombinant antibody of the invention comprises a portion of a heavy chain having an amino acid sequence that targets the antibody to the cell surface wherein said amino acid sequence is fused to the C terminus of said heavy chain portion and may further comprise a light chain or fragment thereof. In a specific embodiment, said amino acid sequence that targets the antibody to the cell surface is a transmembrane domain. In another embodiment, said amino acid sequence that targets the antibody to the cell surface is a GPI anchor signal sequence.

The present invention further relates to vectors comprising polynucleotides encoding a recombinant antibody or fragment thereof that is displayed on the extracellular surface of the cell membrane, referred to herein as a "vector of the invention". In one embodiment, a vector of the invention is a viral vector. In a specific embodiment, a vector of the invention is an adenoviral vector.

The present invention also relates to libraries comprising recombinant antibodies or fragments thereof that are displayed on the extracellular surface of the cell membrane, referred to herein as a "library of the invention". In one embodiment, a library of the invention comprises a library of heavy chain variable regions; it may further comprise a library of light chain variable regions; and it may further comprise a library of variant Fc regions. In one embodiment, a library of the present invention is a library of cells comprising polynucleotides encoding a recombinant antibody or fragment thereof that is displayed on the extracellular surface of the cell membrane.

The invention also provides methods of screening a library of the invention comprising recombinant antibodies or fragments thereof that are displayed on the extracellular surface of the cell membrane. In one embodiment, a method of screening a library allows the identification of an antibody or fragment thereof that binds a specific antigen. In one embodiment, a method of screening a library allows the identification of an antibody or fragment thereof having an altered binding to a specific antigen. In one embodiment, a method of screening a library allows the identification of an antibody or fragment having an altered binding to effector molecules (e.g., FcγRs and/or C1q).

The present invention provides variant Fc regions having altered binding to effector molecules (e.g., FcγRs and/or C1q). The present invention also provides variant Fc regions having an altered effector function. In one embodiment, a variant Fc region of the invention has a reduced antibody dependent cell-mediated cytotoxicity (ADCC).

5. BRIEF DESCRIPTION OF THE FIGURES

For the purpose of illustrating exemplary embodiments of the invention, drawings are provided herein.

Figure 1B:
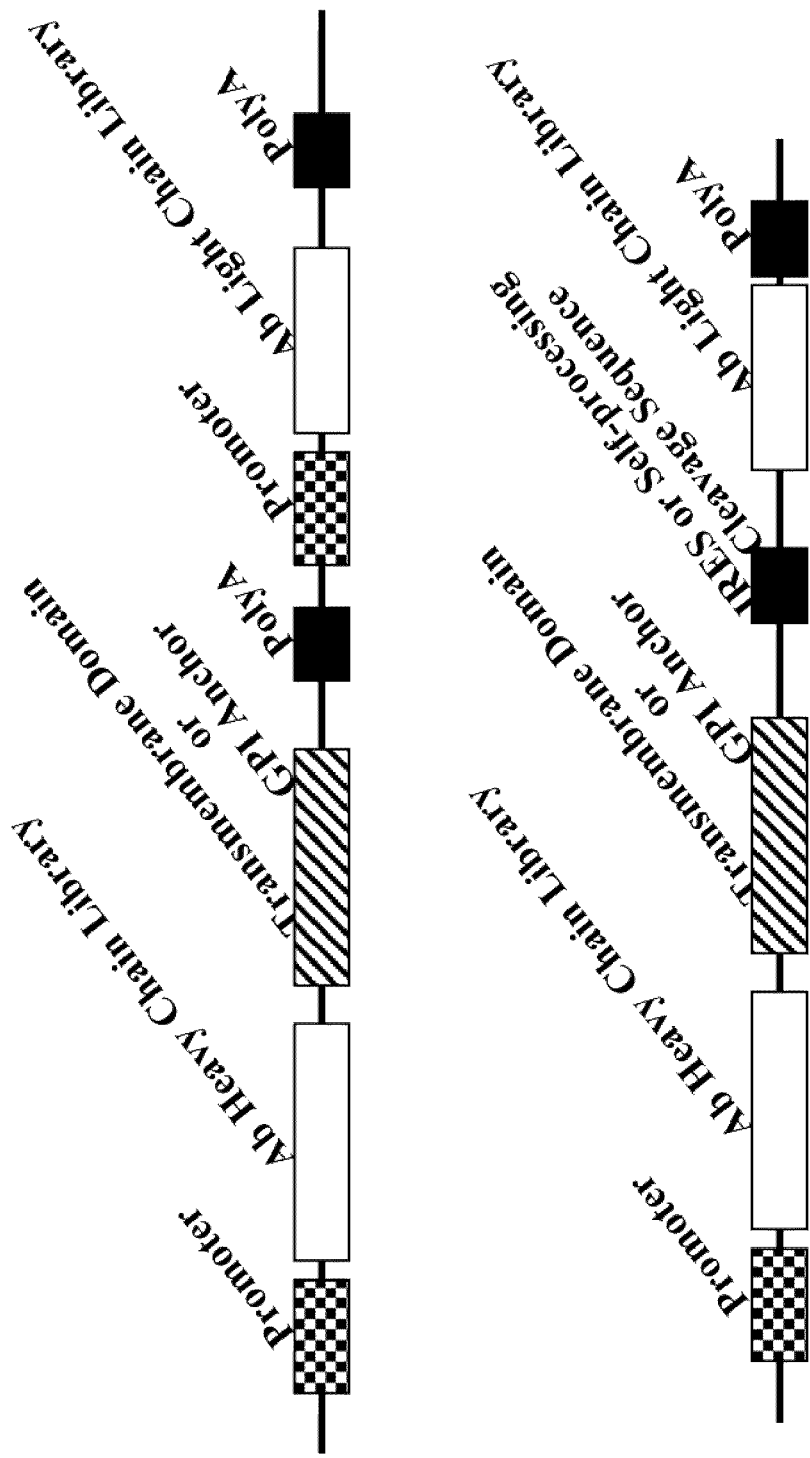
Figure 1C:
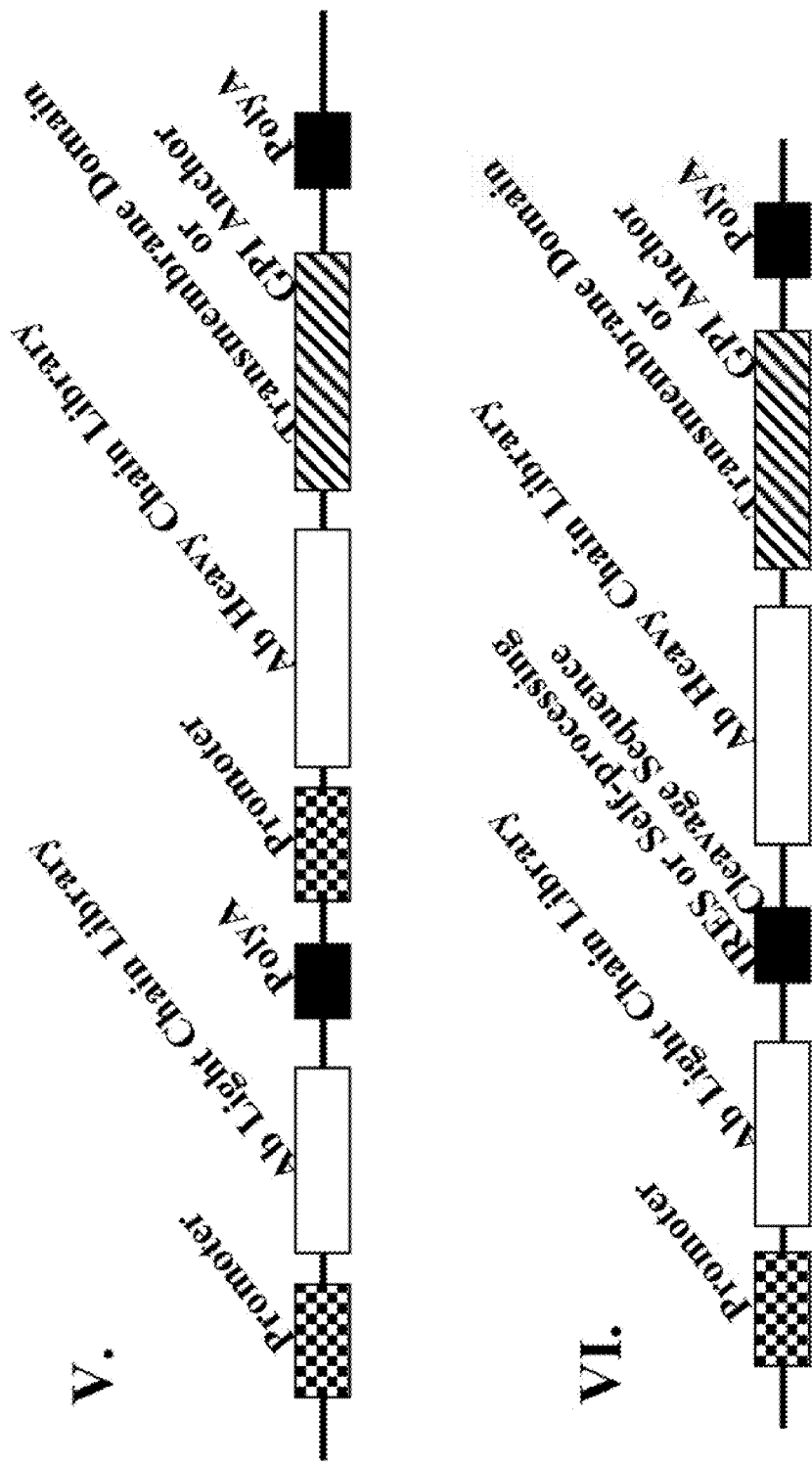

FIG. 1A-C. Schematic representation of non-limiting examples of expression cassettes (I-VI) that may be used for the cell surface display of an antibody or a fragment thereof.

Figure 2:
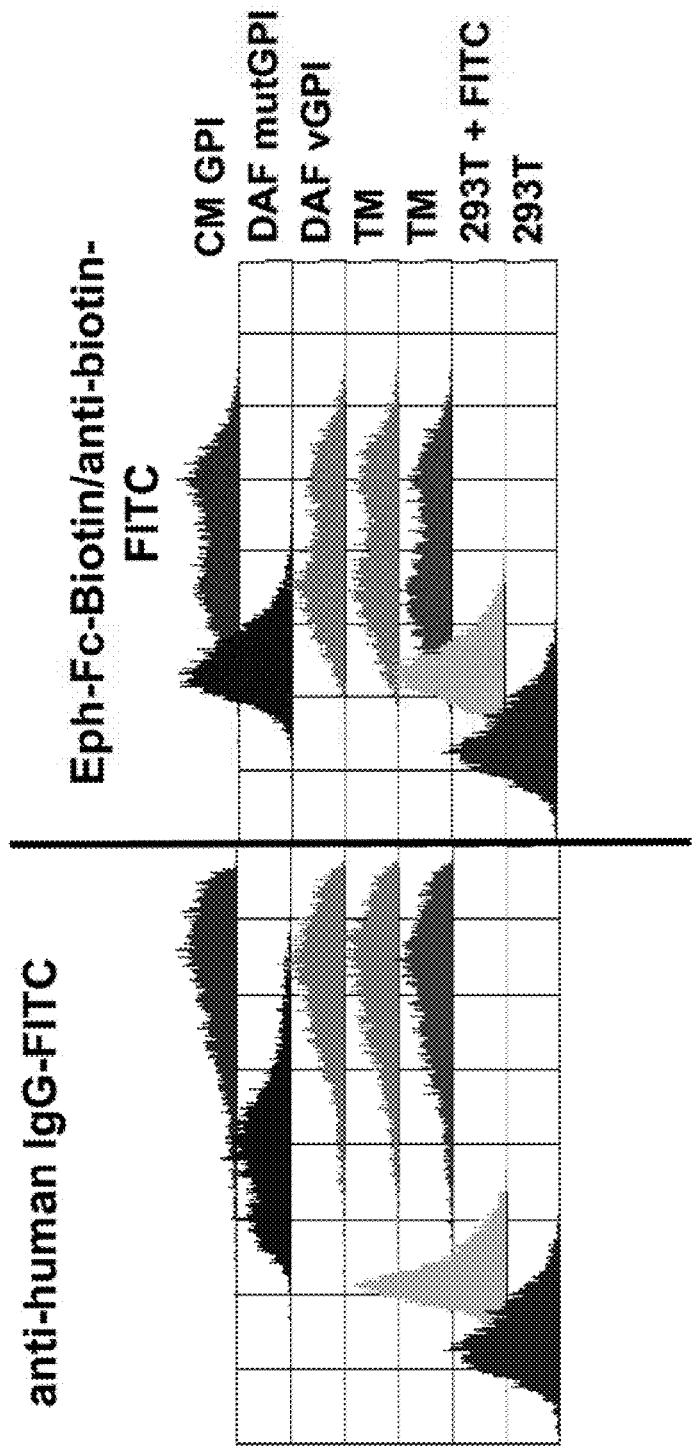

FIG. 2. Fluorescence intensity profile of stained HEK-293T cells expressing an antibody fusion polypeptide comprising a transmembrane domain or a GPI anchor signal. HEK-293T cells expressing an anti-EphA2 antibody comprising a heavy chain fused to i) the GPI anchor signal of carboxypeptidase M (CM GPI), ii) a frameshift mutant GPI anchoring signal of DAF (DAF mutGPI), iii) a variant GPI anchoring signal of DAF (DAF vGPI), or iv) the transmembrane domain of thrombomodulin (TM; two independently isolated clones analyzed) were stained with either FITC conjugated anti-human IgG or biotinylated EphA2-Fc fusion protein/FITC conjugated anti-biotin antibody and analyzed with a flow cytometer. Similarly stained (293T+FITC), as well as non-stained (293T), HEK-293T cells were included as negative control. Cells expressing CM GPI, DAF vGPI, or TM fused anti-EphA2 antibody displayed fluorescence intensity that was significantly higher than that of the control cells. Cells expressing a DAF mutGPI fused anti-EphA2 antibody displayed fluorescence intensity that was substantially the same as that of the control HEK-293T cells FIG. 3. Fluorescence intensity profile of affinity stained HEK-293T cells transfected with different amounts of plasmid DNA encoding an anti-EphA2 fusion antibody comprising a DAF vGPI. HEK-293T cells were transfected with different amounts (0.05, 0.1, 0.5, 1.0, 2.0, 4, and 10 μg) of plasmid DNA. Transfected cells were first contacted with an FcγRIIIA-streptavidin fusion protein and then stained with FITC conjugated anti-streptavidin antibody. The cells were subsequently analyzed on a flow cytometer. Non-transfected HEK-293T cells were included as negative control. The flow cytometry profiles of all the transfected cell populations show a significant shift in mean fluorescence intensity compared to the control cells.

Figure 4:
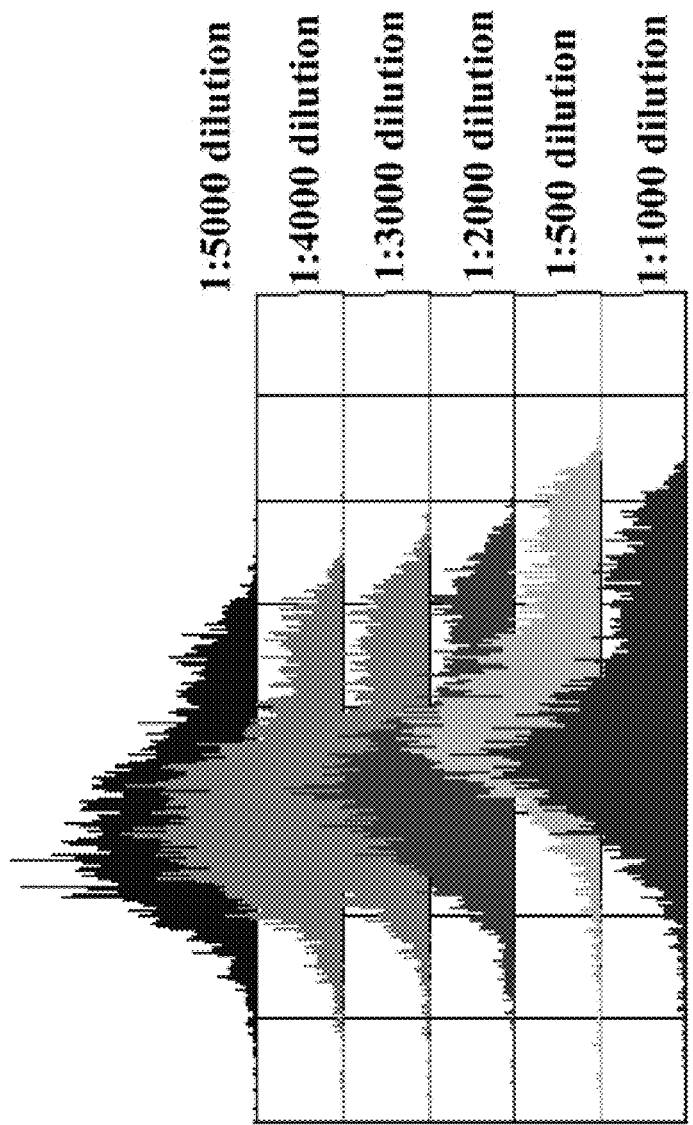

FIG. 4. Fluorescence intensity profile of affinity stained HEK-293T cells expressing an anti-EphA2 fusion antibody comprising a DAF vGPI. HEK-293T cells were transfected with 10 μg of plasmid DNA encoding an anti-EphA2 fusion antibody comprising a DAF vGPI. Transfected cells were divided into aliquots and incubated with different dilutions of FcγRIIIA-streptavidin fusion protein (1:500, 1:1000, 1:2000, 1:3000, 1:4000 and 1:5000). Cells were then stained with FITC conjugated anti-streptavidin antibody and analyzed by flow cytometry. Flow cytometry profiles show that the use of decreasing amounts of FcγRIIIA-streptavidin fusion protein resulted in decreasing staining intensity.

Figure 5:
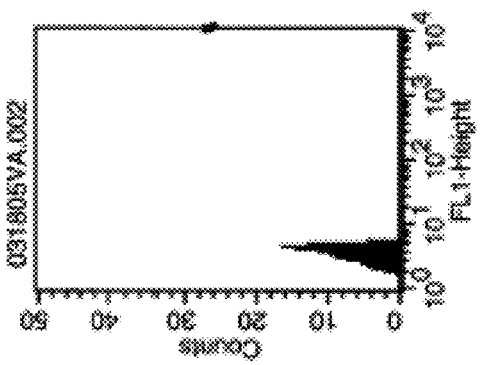
Figure 5:
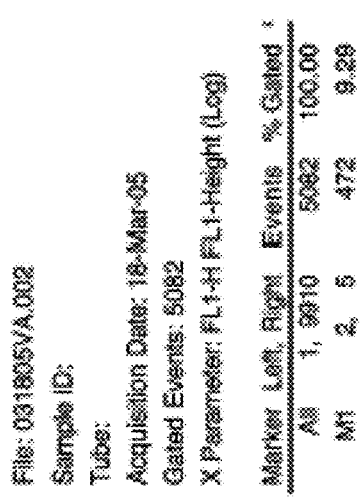
Figure 5:
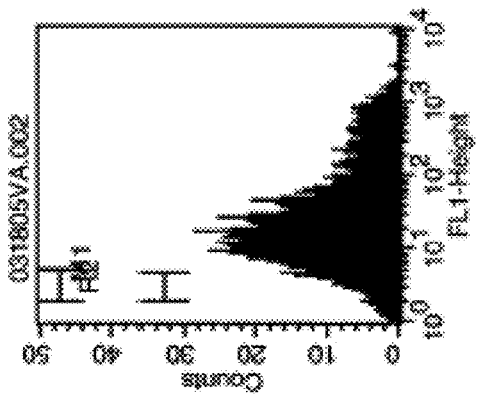

FIG. 5. Sort parameters used for the isolation of Fc variants with low binding affinity for FcγRIIIA HEK-293 cells were transiently transfected with an Fc variant Insertion Library (Fc-IL) and stained with FcγRIIIA-streptavidin fusion protein/FITC conjugated anti-streptavidin antibody. (A) Cells with low fluorescence intensity (approximately 10% of total according to M1 marker) were isolated using gate R2. (B) The isolated cell population displayed uniform low fluorescence intensity.

Figure 6:
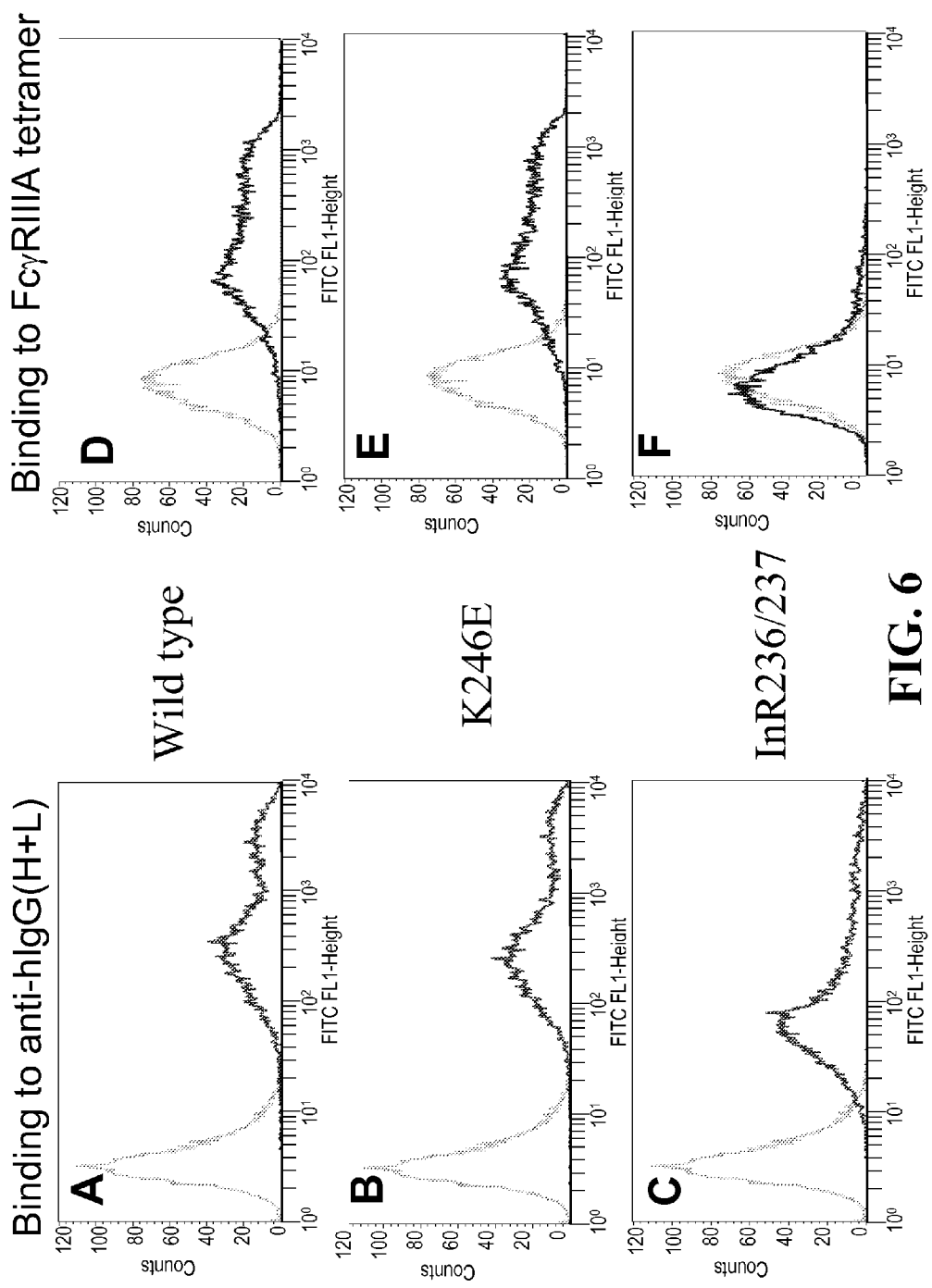

FIG. 6. Fluorescence intensity profile of stained HEK-293 cells expressing Fc variants of an anti-EphA2 fusion antibody comprising a DAF vGPI. HEK-293 cells expressing a wild type (A and D), K246E Fc variant (B and E) or InR236/237 Fc variant (C and F) of an anti-EphA2 fusion antibody comprising a DAF vGPI were analyzed by flow cytometry. Cells were stained either with FITC conjugated anti-human IgG antibody (A-C) or with FcγRIIIA-streptavidin fusion protein/FITC conjugated anti-streptavidin antibody. Each panel contains the flow cytometry profile of antibody expressing (black line) and control (grey line) HEK-293 cells. All three cell populations stained with FITC conjugated anti-human IgG antibody showed similar levels of fluorescence intensity that was significantly different from that of observed for the control cells. When stained with FcγRIIIA-streptavidin fusion protein/FITC conjugated anti-streptavidin antibody, only cells expressing wild type or K246E Fc variant antibodies displayed fluorescence intensity that was significantly higher than that of observed for the control HEK-293 cells.

Figure 7:
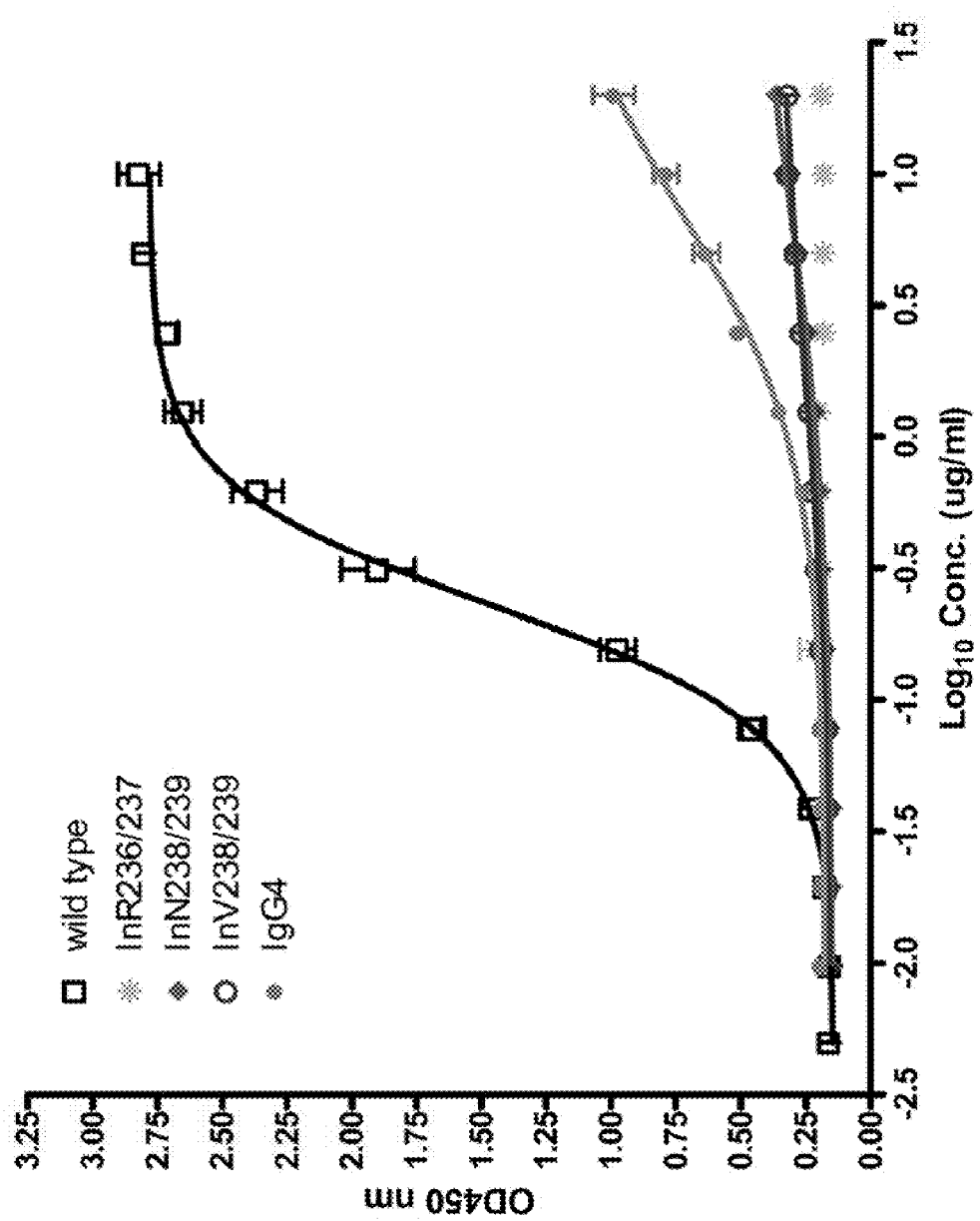

FIG. 7. ELISA based FcγRIIIA binding curve of Fc variants InR236/237, InN238/239, and InV238/239. Binding curves for FcγRIIIA interaction with wild type or Fc variants InR236/237, InN238/239, and InV238/239 anti-EphA2 antibodies were established using standard ELISA protocols. An IgG4 isotype antibody of the same antigen specificity was included as a negative control. The binding curves show that interaction between FcγRIIIA and the InR236/237, InN238/239, or InV238/239 Fc variant is weaker than that of between FcγRIIIA and the Fc region of the IgG4 negative control antibody. FcγRIIIA displayed robust binding to the positive control antibody comprising a wild type Fc region.

Figure 8:
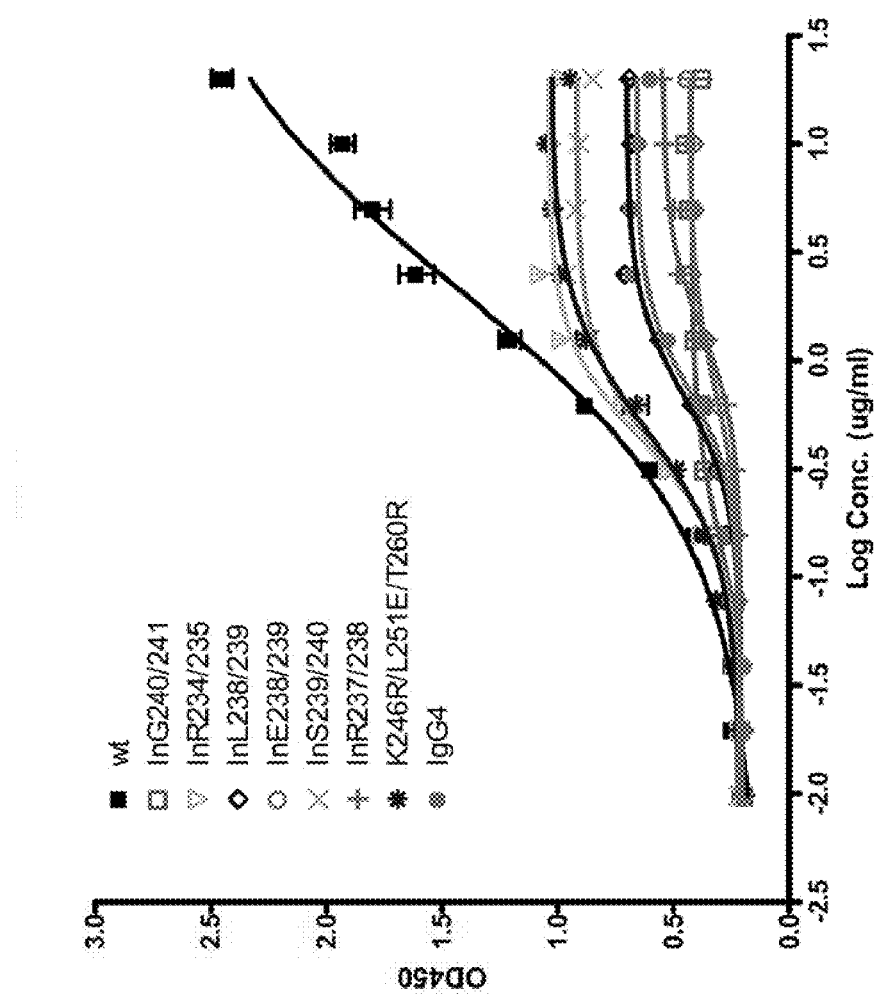

FIG. 8. ELISA based C1q binding curve of Fc variants InG240/241, InR234/235, InL238/239, InE238/239, InS239/240, InR237/238, and K246R/L251E/T260R. Binding curves for C1q interaction with wild type or Fc variants InG240/241, InR234/235, InL238/239, InE238/239, InS239/240, InR237/238, and K246R/L251E/T260R anti-EphA2 antibodies were established using standard ELISA protocols. An IgG4 isotype antibody of the same antigen specificity was included as a negative control. Each of the Fc variants shows reduced binding to C1q as compared to the wild type antibody.

Figure 9:
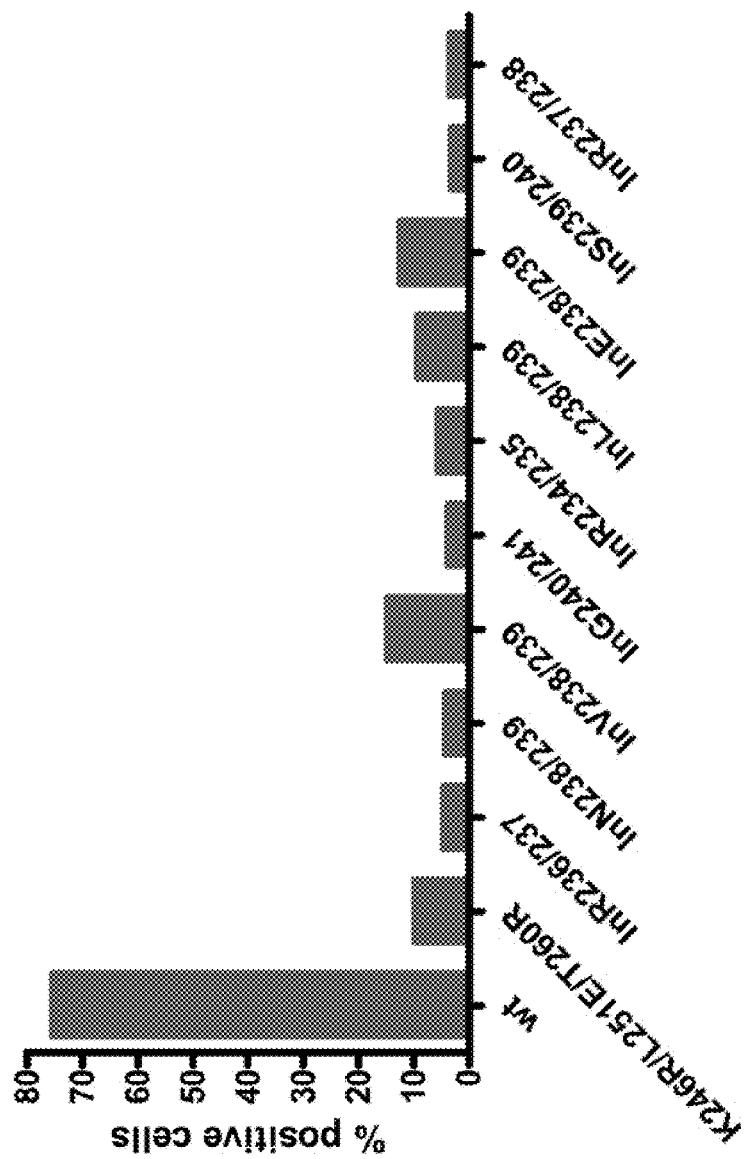

FIG. 9. Percent binding of Fc variants K246R/L251E/T260R, InR236/237, InN238/239, InV238/239, InG240/241, InR234/235, InL238/239, InE238/239, InS239/240 and InR237/238 to THP-1 cells. THP-1 monocytes expressing FcγRI and FcγRII, but not FcγRIIIA, were contacted with wild type or Fc variants K246R/L251E/T260R, InR236/237, InN238/239, InV238/239, InG240/241, InR234/235, InL238/239, InE238/239, InS239/240 and InR237/238 anti-EphA2 antibodies. The percentage of THP-1 monocytes bound by each antibody was determined by staining the cells with FITC conjugated anti-human IgG Fab and analyzing them on a flow cytometer. The obtained results show reduced binding of FcγRI and FcγRII by each of the Fc variants tested compared to the wild type antibody.

Figure 10:
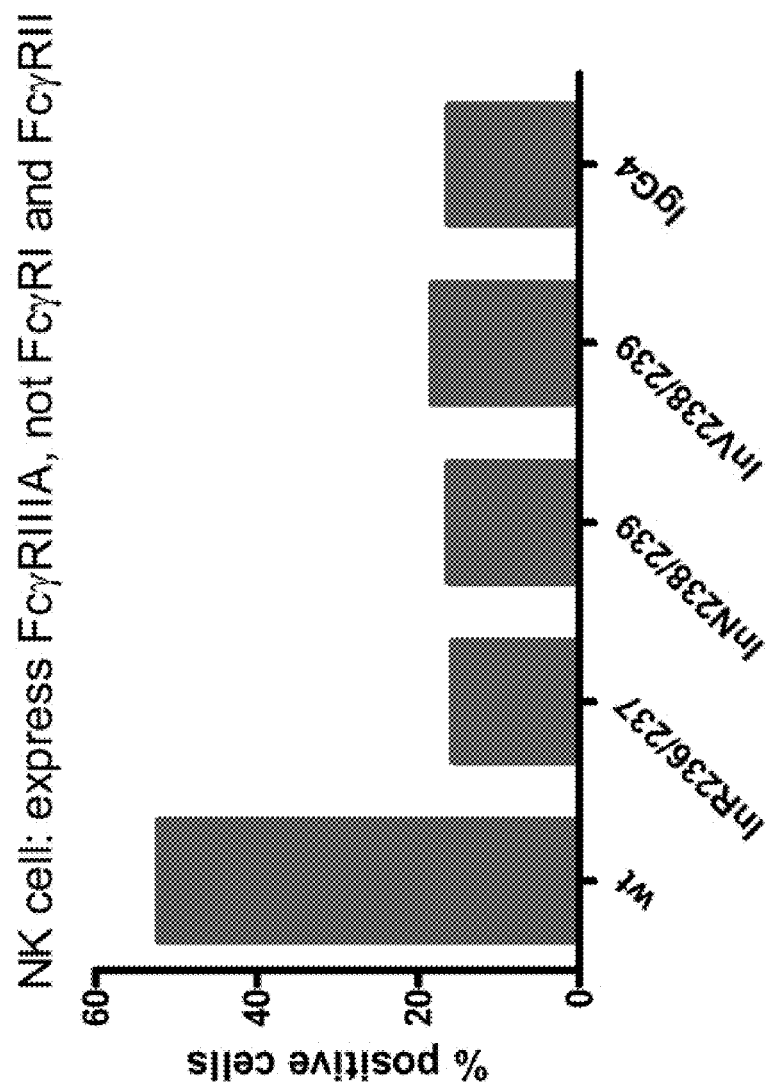

FIG. 10. Percent binding of Fc variants InR236/237, InN238/239, and InV238/239 to NK cells. NK cells expressing FcγRIIIA were contacted with wild type or Fc variants InR236/237, InN238/239, and InV238/239 anti-EphA2 antibodies. The percentage of NK cells bound by each antibody was determined by staining the cells with FITC conjugated anti-human IgG Fab and analyzing them on a flow cytometer. An IgG4 isotype antibody of the same antigen specificity was included as a negative control. The obtained results show reduced binding of FcγRIIIA by each of the Fc variants tested compared to the wild type antibody.

Figure 11:
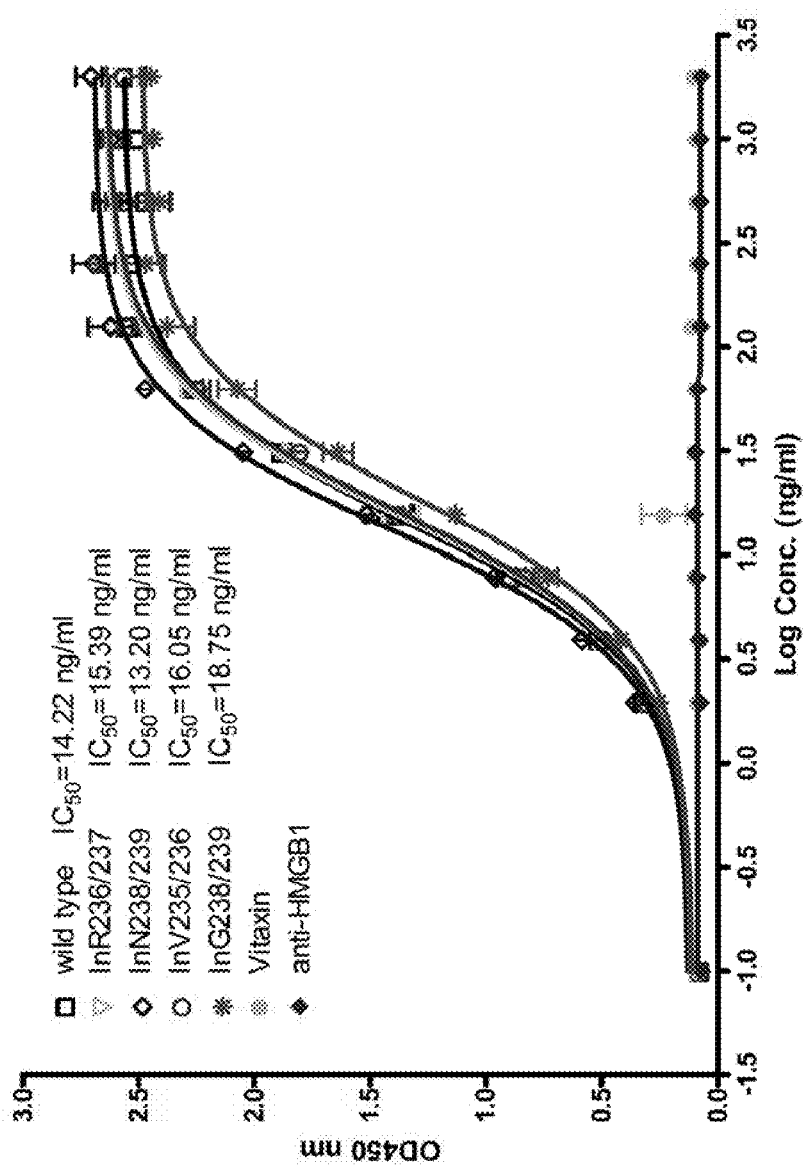

FIG. 11. ELISA based EphA2 binding curve of Fc variants InR236/237, InN238/239, InV235/236, and InG238/239. Human EphA2 binding of wild type and Fc variants InR236/237, InN238/239, InV235/236, and InG238/239 anti-EphA2 antibodies was determined using standard ELISA protocols. Vitaxin® (anti-$\alpha_v\beta_3$ integrin antibody) and an anti-HMGB1 antibody were included in the assay as negative controls. The results show that each of the Fc variants tested binds to human EphA2 with an affinity similar to that of the wild type antibody.

Figure 12:
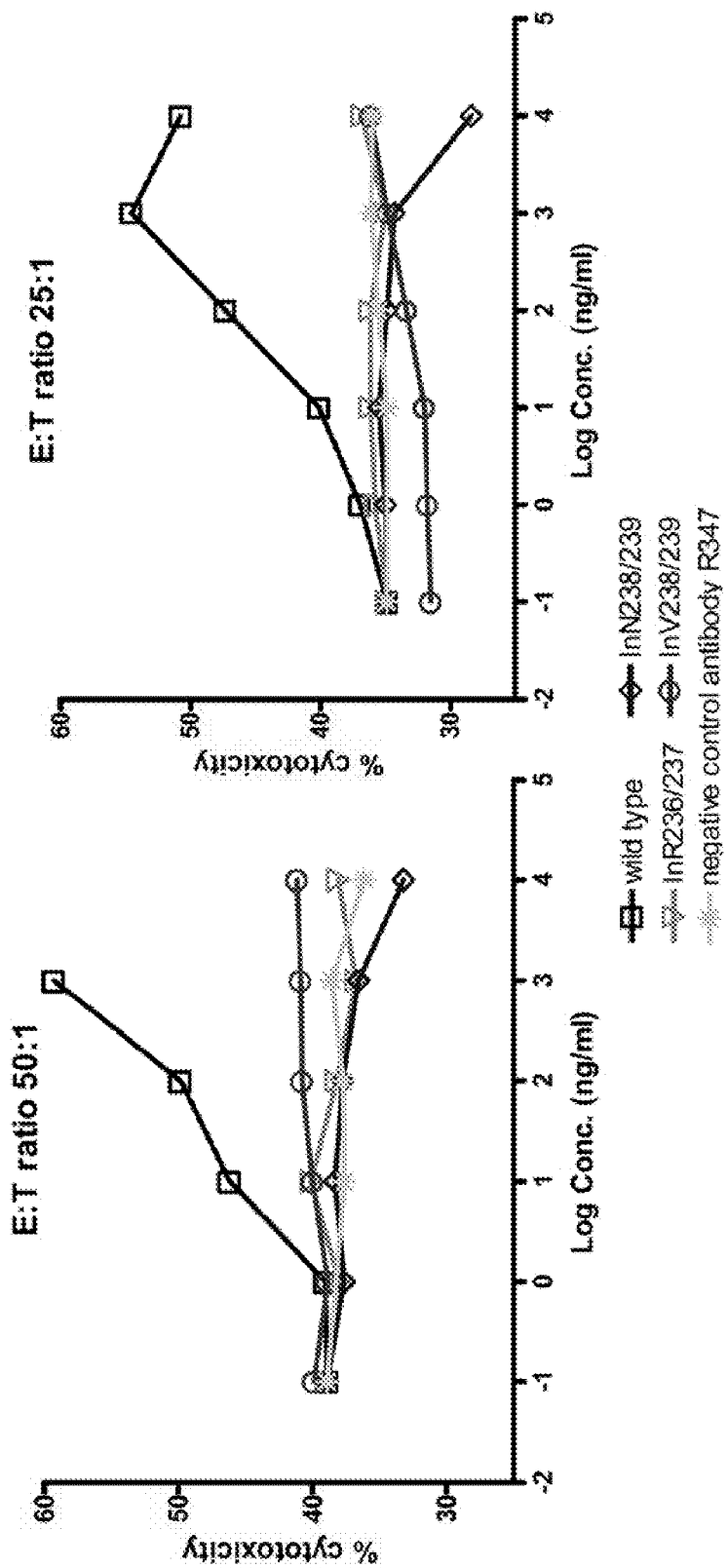

FIG. 12. In vitro ADCC activity of Fc variants InR236/237, InN238/239, InV238/239. ADCC activity of Fc variants InR236/237, InN238/239, InV238/239 was determined at 50:1 (left panel) or a 25:1 (right panel) effector to target cell ratios using standard protocols. Wild type anti-EphA2 antibody and an anti-CD4 antibody (R347) were included as positive and negative controls, respectively. EphA2 expressing A549 cells were used as targets. Purified human peripheral blood mononuclear cells were used as effectors. Cytotoxicity was determined at antibody concentrations between 0.1 and 10000 ng/ml. Each of the Fc variants tested shows ADCC activity similar to that of the negative control antibody. The wild type anti-EphA2 antibody displayed robust ADCC activity under the same conditions.

Figure 13:
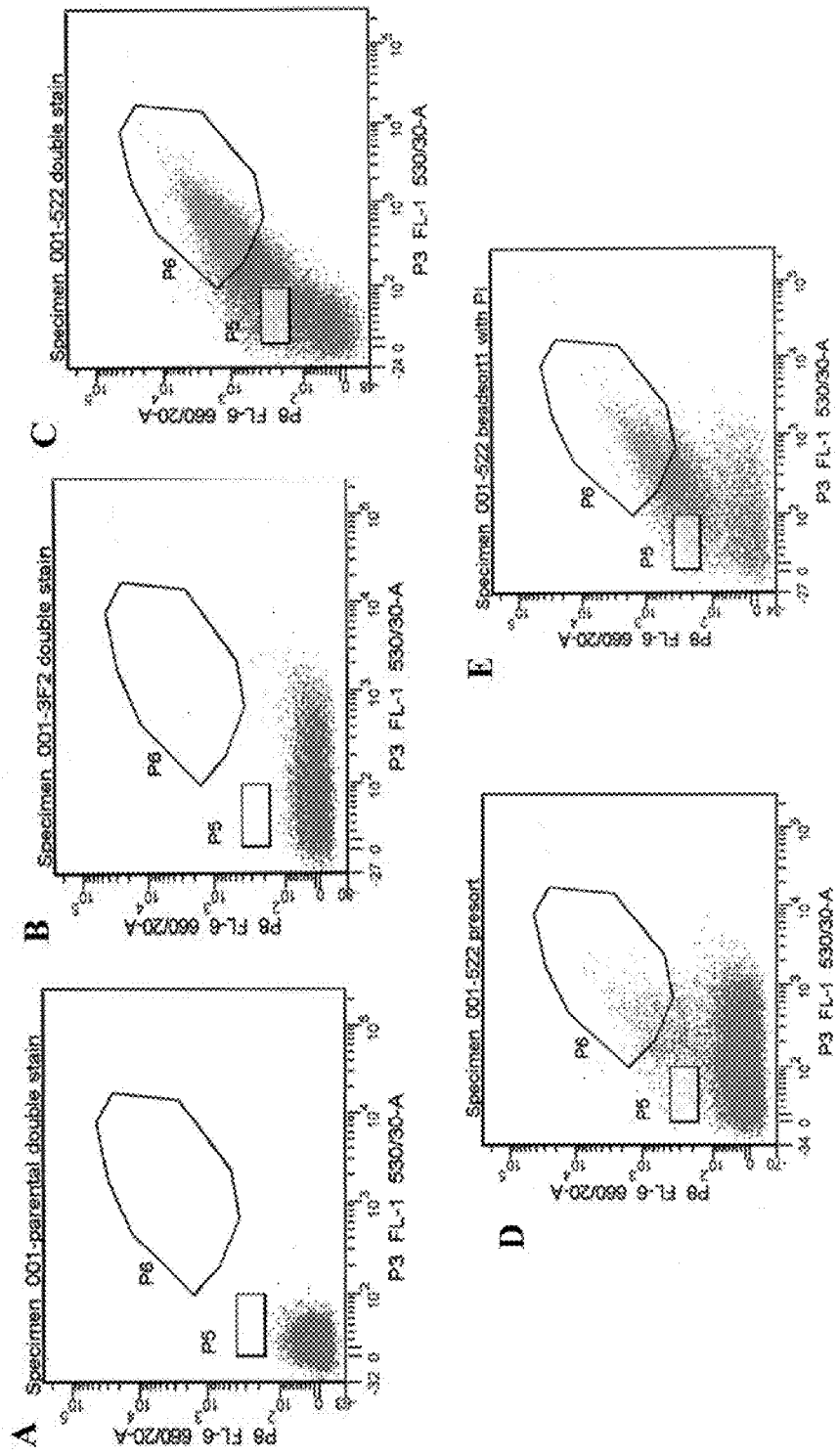

FIG. 13. Flow cytometry profiles from Proof of Principle Selection Experiment I. Cells were incubated with $\alpha V\beta 3$-biotin followed by staining with FITC conjugated anti-human IgG-Fc and APC-conjugated streptavidin. Samples displayed are as follows: (A) negative control 293A cells, (B) 293A cells infected with a cell surface displayed 3F2 anti-EphA2 antibody encoding ts369 mutant adenovirus, (C) 293A cells infected with a cell surface displayed Abegrin anti-$\alpha V\beta 3$ integrin ScFvFc encoding ts369 mutant adenovirus, (D) 293A cells infected with the artificial library before magnetic bead mediated selection, (E) 293A cells infected with the artificial library after magnetic bead mediated selection. Gate P6 was used to sort double positive cells.

Figure 14:
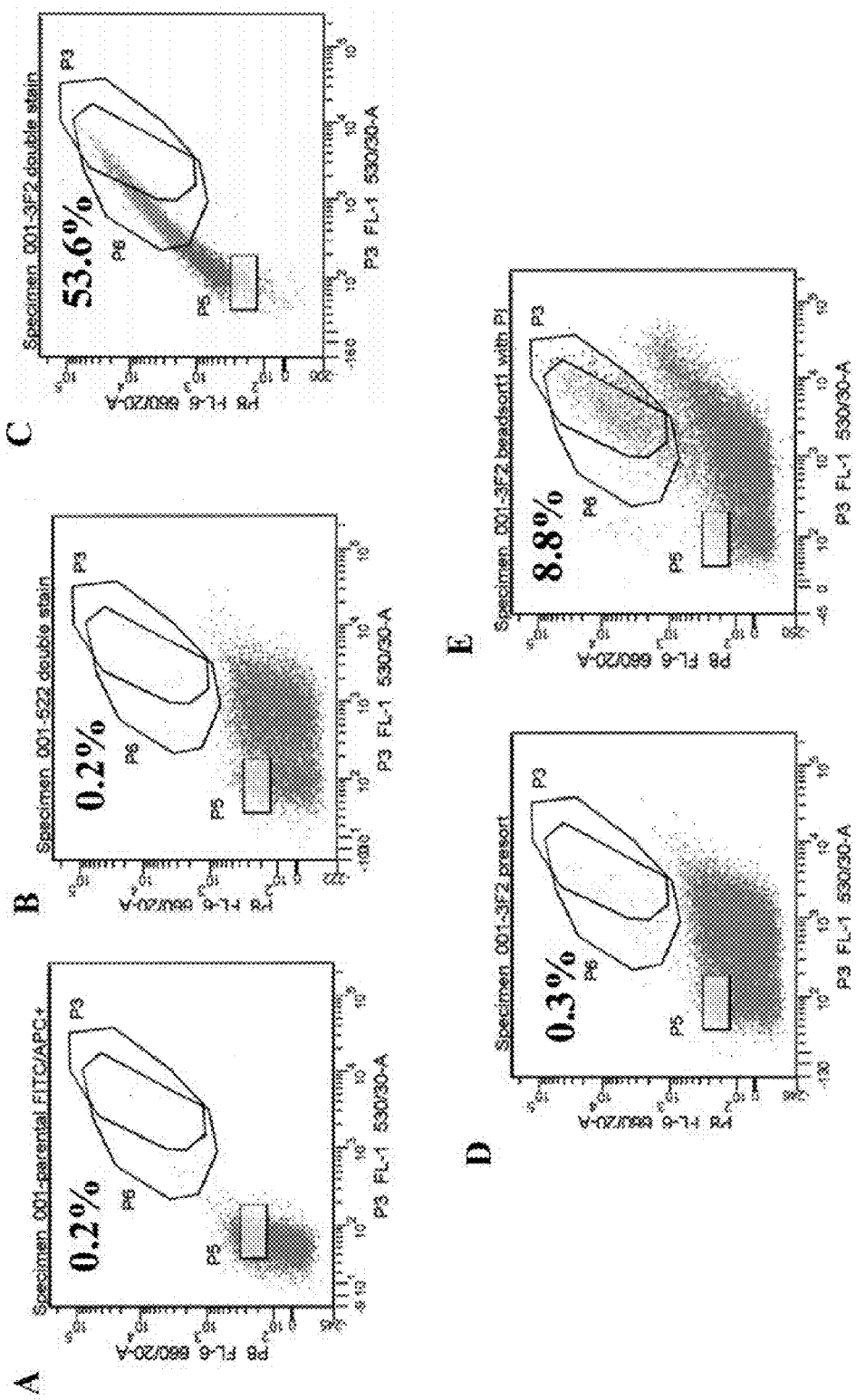

FIG. 14. Flow cytometry profiles from Proof of Principle Selection Experiment II. Cells were incubated with biotinylated EphA2 followed by staining with FITC conjugated anti-human IgG-Fc and APC-conjugated streptavidin. Samples displayed are as follows: (A) negative control 293A cells, (B) 293A cells infected with a cell surface displayed Abegrin anti-$\alpha V\beta 3$ integrin antibody encoding ts369 mutant adenovirus, (C) 293A cells infected with a cell surface displayed 3F2 anti-EphA2 ScFvFc encoding ts369 mutant adenovirus, (D) 293A cells infected with the artificial library before magnetic bead mediated selection, (E) 293A cells infected with the artificial library after magnetic bead mediated selection. Gate P6 was used to sort double positive cells. Percentage of cells covered by Gate P6 is displayed in the panels.

Figure 15:
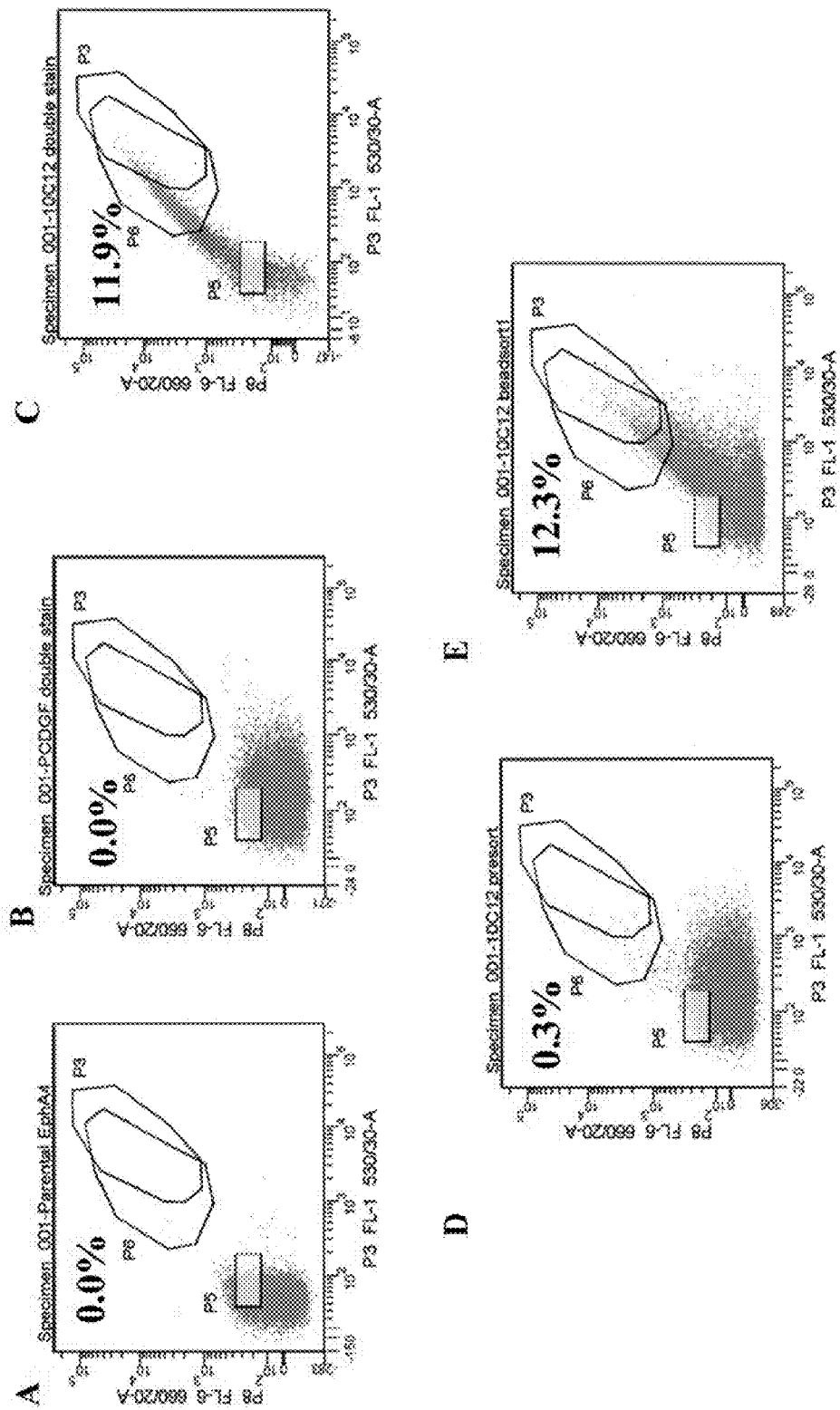

FIG. 15. Flow cytometry profiles from Proof of Principle Selection Experiment III. Cells were incubated with biotinylated EphA2 followed by staining with FITC conjugated anti-human IgG-Fc and APC-conjugated streptavidin. Samples displayed are as follows: (A) negative control 293A cells, (B) 293A cells infected with a cell surface displayed anti-PCDGF antibody encoding ts369 mutant adenovirus, (C) 293A cells infected with a cell surface displayed 10C12 anti-EphA2 ScFvFc encoding ts369 mutant adenovirus, (D) 293A cells infected with the artificial library before magnetic bead mediated selection, (E) 293A cells infected with the artificial library after magnetic bead mediated selection. Gate P6 was used to sort double positive cells. Percentage of cells covered by Gate P6 is displayed in the panels.

6. DEFINITIONS

As used herein, the terms "antibody" and "antibodies" refer to monoclonal antibodies, multispecific antibodies, human antibodies, humanized antibodies, camelised antibodies, chimeric antibodies, single-chain Fvs (scFv), disulfide-linked Fvs (sdFv), Fab fragments, F (ab') fragments, and anti-idiotypic (anti-Id) antibodies (including, e.g., anti-Id antibodies to antibodies of the invention), and epitope-binding fragments of any of the above. In particular, antibodies include immunoglobulin molecules and immunologically active fragments of immunoglobulin molecules, i.e., molecules that contain an antigen binding site, these fragments may or may not be fused to another immunoglobulin domain including but not limited to, an Fc region or fragment thereof. As used herein, the terms "antibody" and "antibodies" also include the Fc variants, full-length antibodies and Fc variant-fusions comprising Fc regions, or fragments thereof. Fc variant-fusions include but are not limited to, scFv-Fc fusions, variable region (e.g., VL and VH)-Fc fusions, scFv-scFv-Fc fusions. Antibodies can be of any type (e.g., IgG, IgE, IgM, IgD, IgA and IgY), class (e.g., IgG1, IgG2, IgG3, IgG4, IgA1 and IgA2) or subclass.

The complementarity determining regions (CDRs) residue numbers referred to herein are those of Kabat et al. (1991, NIH Publication 91-3242, National Technical Information Service, Springfield, Va.). Specifically, residues 24-34 (CDR1), 50-56 (CDR2) and 89-97 (CDR3) in the light chain variable domain and 31-35 (CDR1), 50-65 (CDR2) and 95-102 (CDR3) in the heavy chain variable domain. Note that CDRs vary considerably from antibody to antibody (and by definition will not exhibit homology with the Kabat consensus sequences). Maximal alignment of framework residues frequently requires the insertion of "spacer" residues in the numbering system, to be used for the Fv region. It will be understood that the CDRs referred to herein are those of Kabat et al. supra. In addition, the identity of certain individual residues at any given Kabat site number may vary from antibody chain to antibody chain due to interspecies or allelic divergence.

As used herein "Fc region" includes the polypeptides comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, Fc comprises immunoglobulin domains Cgamma2 and Cgamma3 (Cγ2 and Cγ3) and the hinge between Cgamma1 (Cγ1) and Cgamma2 (Cγ2). Although the boundaries of the Fc region may vary, the human IgG heavy chain Fc region is usually defined to comprise residues C226 or P230 to its carboxyl-terminus, wherein the numbering is according to the EU index as in Kabat et al. (1991, NIH Publication 91-3242, National Technical Information Service, Springfield, Va.). The "EU index as set forth in Kabat" refers to the residue numbering of the human IgG1 EU antibody as described in Kabat et al. supra. Fc may refer to this region in isolation, or this region in the context of an antibody, antibody fragment, or Fc fusion protein. An Fc variant protein may be an antibody, Fc fusion, or any protein or protein domain that comprises an Fc region. Particularly preferred are proteins comprising variant Fc regions, which are non-naturally occurring variants of an Fc region. The amino acid sequence of a non-naturally occurring Fc region (also referred to herein as a "variant Fc region") comprises a substitution, insertion and/or deletion of at least one amino acid residue compared to the wild type amino acid sequence. Any new amino acid residue appearing in the sequence of a variant Fc region as a result of an insertion or substitution may be referred to as a non-naturally occurring amino acid residue. Note: Polymorphisms have been observed at a number of Fc positions, including but not limited to Kabat 270, 272, 312, 315, 356, and 358, and thus slight differences between the presented sequence and sequences in the prior art may exist.

As used herein, the term "transmembrane domain" refers to the domain of a peptide, polypeptide or protein that is capable of spanning the plasma membrane of a cell. These domains can be used to anchor an antibody on the cell membrane.

A "chimeric antibody" is a molecule in which different portions of the antibody are derived from different immunoglobulin molecules such as antibodies having a variable region derived from a non-human antibody and a human immunoglobulin constant region. Methods for producing chimeric antibodies are known in the art. See e.g., Morrison, 1985, *Science* 229:1202; Oi et al., 1986, *BioTechniques* 4:214; Gillies et al., 1989, *J. Immunol. Methods* 125:191-202; and U.S. Pat. Nos. 5,807,715, 4,816,567, and 4,816,397, CDR-grafting (EP 239,400; PCT Publication No. WO 91/09967; and U.S. Pat. Nos. 5,225,539, 5,530,101, and 5,585,089), veneering or resurfacing (EP 592,106; EP 519,596; Padlan, 1991, *Molecular Immunology* 28(4/5): 489-498; Studnicka et al., 1994, *Protein Engineering* 7:805; and Roguska et al., 1994, PNAS 91:969), and chain shuffling (U.S. Pat. No. 5,565,332).

A "humanized antibody" is an antibody or its variant or fragment thereof which is capable of binding to a predetermined antigen and which comprises a framework region having substantially the amino acid sequence of a human immunoglobulin and a CDR having substantially the amino acid sequence of a non-human immunoglobulin. A humanized antibody comprises substantially all of at least one, and typically two, variable domains (Fab, Fab', F(ab')2, Fabc, Fv) in which all or substantially all of the CDR regions correspond to those of a non-human immunoglobulin (i.e., donor antibody) and all or substantially all of the framework regions are those of a human immunoglobulin consensus sequence. In one embodiment, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain. The humanized antibody can be selected from any class of immunoglobulins, including, but not limited to, IgM, IgG, IgD, IgA and IgE, and any isotype, including, but not limited to, IgG1, IgG2, IgG3 and IgG4. In another embodiment, the constant domain is a complement fixing constant domain where it is desired that the humanized antibody exhibit cytotoxic activity, and the class is typically IgG1. Where such cytotoxic activity is not desirable, the constant domain may be of the IgG 2 class. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. In one embodiment, at least 75%, at least 90%, and or at least 95% of the humanized antibody residues will correspond to those of the parental framework region (FR) and CDR sequences. Humanized antibody can be produced using variety of techniques known in the art, including but not limited to, CDR-grafting (European Patent No. EP 239,400; PCT Publication No. WO 91/09967; and U.S. Pat. Nos. 5,225, 539, 5,530,101, and 5,585,089), veneering or resurfacing (European Patent Nos. EP 592,106 and EP 519,596; Padlan, 1991, Molecular Immunology 28(4/5): 489-498; Studnicka et al., 1994, *Protein Engineering* 7(6): 805-814; and Roguska et al., 1994, *PNAS* 91:969-973), chain shuffling (U.S. Pat. No. 5,565,332), and techniques disclosed in, e.g., U.S. Pat. No. 6,407,213, U.S. Pat. No. 5,766,886, PCT Patent Publication WO 93/17105, Tan et al., 2002, *J. Immunol.* 169:1119-25, Caldas et al., 2000, *Protein Eng.* 13: 353-60, Morea et al., 2000, *Methods* 20: 267-79, Baca et al., 1997, *J. Biol. Chem.* 272: 10678-84, Roguska et al., 1996, *Protein Eng.* 9: 895-904, Couto et al., 1995, *Cancer Res.* 55 (23 Supp): 5973s-5977s, Couto et al., 1995, *Cancer Res.* 55: 1717-22, Sandhu JS, 1994, *Gene* 150: 409-10, and Pedersen et al., 1994, *J. Mol. Biol.* 235: 959-73). Often, framework residues in the framework regions will be substituted with the corresponding residue from the CDR donor antibody to alter and/or improve antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, *Nature* 332:323).

As used herein the term "multiplicity of infection" (MOI) means the number of infectious virus particles per cell.

The term "ADCC" (antibody-dependent cell-mediated cytotoxicity) refers to a cell-mediated reaction in which non-specific cytotoxic cells that express Fc receptors (FcR) (e.g. natural killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. To assess ADCC activity of a molecule of interest, an in vitro ADCC assay (e.g. such as that described in U.S. Pat. No. 5,500,362 and U.S. Pat. No. 5,821,337) may be performed. Useful effector cells for such assays include peripheral blood mononuclear cells (PBMC) and natural killer (NK) cells.

"Complement dependent cytotoxicity" and "CDC" refer to the lysing of a target cell in the presence of complement. The complement activation pathway is initiated by the binding of the first component of the complement system (C1q) to a molecule, an antibody for example, complexed with a cognate antigen. To assess complement activation, a CDC assay, e.g. as described in Gazzano-Santoro et al., 1996, *J. Immunol. Methods*, 202:163, may be performed.

7. DETAILED DESCRIPTION

The present invention relates to a recombinant antibody or fragment thereof that is displayed on the extracellular surface of the cell membrane, referred to herein as an "antibody of the invention" and like terms.

In one embodiment, an antibody of the invention is a murine antibody, a chimeric antibody, a humanized antibody or human antibody. In one embodiment, an antibody of the invention is a human antibody.

In one embodiment, an antibody of the invention is of an immunoglobulin type selected from the group consisting of IgA, IgE, IgM, IgD, IgY and IgG.

In one embodiment, a recombinant antibody of the invention comprises a heavy chain or fragment thereof having an amino acid sequence that targets the antibody to the cell surface. In one embodiment, a recombinant antibody of the invention comprises a heavy chain or fragment thereof having an amino acid sequence that targets the antibody to the cell surface fused to the C terminal end of said heavy chain or fragment thereof.

In another embodiment, a recombinant antibody of the invention comprises a light chain or fragment thereof having an amino acid sequence that targets the antibody to the cell surface. In a specific embodiment, a recombinant antibody of the invention comprises a light chain or fragment thereof having an amino acid sequence that targets the antibody to the cell surface fused to the C terminal end of said light chain or fragment thereof.

In one embodiment, a recombinant antibody of the invention comprises a full length heavy chain having an amino acid sequence that targets the antibody to the cell surface wherein said amino acid sequence is fused to the C terminus of said heavy chain and may further comprise a full length light chain or a fragment thereof. In still another embodiment, a recombinant antibody of the invention comprises a portion of a heavy chain having an amino acid sequence that targets the antibody to the cell surface wherein said amino acid sequence is fused to the C terminus of said heavy chain portion and may further comprise a light chain or fragment thereof.

In a specific embodiment, said amino acid sequence that targets the antibody to the cell surface is a transmembrane domain. In another embodiment, said amino acid sequence that targets the antibody to the cell surface is a GPI anchor signal sequence.

The present invention further relates to vectors comprising polynucleotides encoding a recombinant antibody or fragment thereof that is displayed on the extracellular surface of the cell membrane, referred to herein as a "vector of the invention". In one embodiment, a vector of the invention is capable of replication. In one embodiment, a vector of the invention is a viral vector. In one embodiment, a vector of the invention is an adenoviral vector, a baculoviral vector, an adeno associated viral vector, a herpes viral vector or a lentiviral vector. In a specific embodiment, a vector of the invention is an adenoviral vector.

The present invention also relates to libraries comprising recombinant antibodies or fragments thereof that are displayed on the extracellular surface of the cell membrane, referred to herein as a "library of the invention". The present invention provides antibody or antibody fragment libraries and methods of screening cells displaying the library of antibodies and/or antibody fragment on the cell surface. These methods involve using vectors including, but not limited to, viral vectors to deliver an antibody library to cells, wherein expression of the library results in the display of the antibodies on the cell surface. Also, provided are viral vectors and cells encoding and/or displaying an antibody and/or antibody fragment library.

In one embodiment, a library of the invention may comprise a library of heavy chain variable regions; it may further comprise a library of light chain variable regions; and it may further comprise a library of variant Fc regions.

In one embodiment, a library of the present invention is a library of cells comprising polynucleotides encoding a recombinant antibody or fragment thereof that is displayed on the extracellular surface of the cell membrane. In one embodiment, mammalian cells comprise a library of the invention. In a specific embodiment, a library of the invention is comprised by cells selected from the group consisting of NS0 cells, CHO cells, Vero cells, Sf-9 cells, COS7 cells, and 293 cells.

The invention also provides methods of screening a library of the invention comprising recombinant antibodies or fragments thereof that are displayed on the extracellular surface of the cell membrane. In one embodiment, a method of screening a library allows the identification of an antibody or fragment thereof that binds a specific antigen. In one embodiment, a method of screening a library allows the identification of an antibody or fragment thereof having an altered binding for a specific antigen. In one embodiment, a method of screening a library allows the identification of an antibody or fragment having an altered binding for effector molecules (e.g., FcγRs and/or C1q).

The present invention provides variant Fc regions having altered binding to effector molecules (e.g., FcγRs and/or C1q). The present invention also provides variant Fc regions having an altered effector function. In one embodiment, a variant Fc region of the invention has a reduced antibody dependent cell-mediated cytotoxicity (ADCC).

The present invention provides a method for selecting mammalian cells that express at least one antibody or a fragment thereof with desirable binding characteristics wherein said method comprises: a) introduction into mammalian cells a library of nucleic acids in an expression vector, wherein said nucleic acid encodes an antibody, or an antibody fragment that is displayed on the cell surface; b) culturing the mammalian cells comprising the library to allow expression and cell surface presentation of each vector encoded polypeptides; c) contacting the cells with an antigen; and d) isolating the cells that comprise at least one cell surface displayed polypeptide that binds to the antigen. The present invention further provides 1) recovering nucleic acids from the isolated mammalian cells; 2) amplifying nucleic acids encoding at least one antibody variable region from the nucleic acids; 3) inserting the amplified nucleic acids into a second vector, wherein the second vector, with the inserted nucleic acids, encodes a secreted soluble antibody and 4) transforming a host cell with the second vector.

In certain embodiments the antibody or fragment thereof comprises an amino acid sequence that can target the polypeptide for cell surface display (examples include, but are not limited to, transmembrane domain sequences and GPI anchor signal sequences). In one embodiment, the heavy chain of the antibody or fragment thereof comprises the amino acid sequence that can target the polypeptide for cell surface display. In another embodiment, the light chain of the antibody or fragment thereof comprises the amino acid sequence that can target the polypeptide for cell surface display.

In one embodiment, most or all cells in a library of cells express only one clonal antibody. In another embodiment, most or all cells in a library of cells express at least two different antibodies. In one embodiment, a vector of the invention codes for an antibody heavy chain or fragment thereof. In another embodiment, a vector of the invention additionally codes for an antibody or antibody fragment light chain, wherein both the heavy chain and light chain are expressed in transduced cells. In certain embodiments, a vector of the invention is a viral vector.

The invention further provides viral vectors encoding a library of antibodies or antibody fragments that are displayed on the cell membrane when expressed in a cell. The present invention provides cells comprising a viral vector nucleic acid and methods of screening the libraries for antibodies or antibody fragments with desired characteristics.

The present invention also provides methods for screening antibodies based on antibody dependent cell-mediated cytotoxicity (ADCC) effect. In one embodiment, a viral vector encodes a library of antibody Fc variants.

7.1 Viral Vectors

Viral vectors of the present invention comprise nucleic acids that code for a library of heavy chain sequences for an antibody or antibody fragment that when expressed in a cell, the antibody or antibody fragment is bound to the cell surface. In one embodiment, when bound to the cell surface, the library of antibodies or antibody fragments is on the extracellular side of the cell membrane. In one embodiment, the viral vector library further encodes a library of light chain sequences of antibodies or antibody fragments (See examples I-VI in FIG. 1A-C).

Viral vectors offer several advantages for delivering an antibody or antibody fragment library. The diversity of the library is one consideration when preparing and screening the antibody library. Phage display antibody libraries can typically have a diversity of about $10^9$ unique antibodies. In the case of cell display antibody libraries, if each cell expresses only one unique antibody one would need to utilize at least $10^9$ and generally $10^{10}$ or more cells to achieve an equivalent diversity. This is a large number of cells to handle for screening and it would be preferable to work with a smaller number of cells, while maintaining diversity. In the present invention, viral vectors are utilized to deliver the antibody or antibody fragment libraries. This allows one to infect at chosen multiplicities of infection (MOI). The MOI can be adjusted to display a certain average number of unique antibodies per cell. For example, an MOI of 50 may be used which will allow the expression of an average of 50 unique antibodies per cell. As with other library screening methods, the methods of the present invention may include a first round of screening/enrichment. In some embodiments of the invention, the cells are infected with an MOI of at most: $10^{-2}$, $10^{-1}$, 1, 2, 3, 4, 5, 6, 7, 8, 9, 10, 15, 20, 50, 100, 200, 500, $10^3$, $10^4$, or $10^5$. Optionally, further rounds of screening may be performed by screening the viral vectors coding for the selected antibodies. In one embodiment, the secondary rounds of selection utilize a lower MOI than in the first round of selection.

Any viral vector may be utilized in accordance with the present invention. Viral vectors include, but are not limited to, retroviral vectors, vaccinia vectors, lentiviral vectors, herpes virus vectors (e.g., HSV), baculoviral vectors, cytomegalovirus (CMV) vectors, papillomavirus vectors, simian virus (SV40) vectors, Sindbis vectors, semliki forest virus vectors, adenoviral vectors, and adeno-associated viral (AAV) vectors. In one embodiment, the viral vector is a high titer viral vector. A high titer viral vector is one that can be isolated and/or concentrated to a titer of at least $10^9$ viral particles per milliliter. In one embodiment, the viral vector antibody library is a high titer viral vector. In one embodiment, the viral vector of the invention is an adenovirus, baculovirus, AAV or herpes virus vector. In one embodiment, the viral vector is not a vaccinia vector.

In one embodiment, the viral vector is an AAV vector. In one embodiment, the AAV vectors encode both an antibody heavy and light chain library. For examples and further description of AAV vectors encoding antibodies see US2005003482, US20040265955 and Fang et al. *Nat. Biotechnol.* 2005 May; 23(5):584-90. These vectors can be utilized in the present invention by cloning a GPI anchor or transmembrane coding sequence in-frame with the antibody heavy chain as described herein.

In one embodiment, the viral vector is an adenoviral vector. An adenoviral vector may be any vector derived from an adenovirus wherein the nucleic acid of the viral vector can be packaged into adenoviral capsid proteins. The adenoviral vector may be derived from any adenoviral serotype or may even be a chimeric adenoviral vector with different portions derived from at least 2 different adenoviral serotypes. The adenoviral vector may be derived from a human or another animal adenovirus. In one embodiment, the adenoviral vector is derived from human adenovirus serotype 2, 3, 5, 12, 35 or 40. The adenoviral vectors may be replication competent or incompetent in relation to the cell being infected. In one embodiment, the adenoviral vector is replication competent in relation to the cell being infected. For example, the adenoviral vector may comprise a deletion of the E1 region and this vector is used to infect a 293 cell that expresses the E1 genes in trans, thus allowing the adenoviral vector to replicate. Many other adenoviral vector gene deletions and corresponding complementing cell line combinations are known in the art. In one embodiment, the adenoviral vector may be replication incompetent in relation to the cell being infected. For example, an E1 deleted adenoviral vector used to infect A549 cell. In one embodiment, the replication incompetent adenoviral vector is rescued with a helper virus (e.g., expressing E1 proteins). In one embodiment, 1) cells are infected with a replication incompetent adenoviral virus coding for an antibody that will be displayed on the cell surface; 2) cells are screened and sorted for those displaying antibodies with desired binding properties; 3) infecting the positive sorted cells with a helper virus to rescue the viral vectors. The helper virus can be any virus that expresses at least one complementing gene product for the adenoviral vector (e.g. E1 proteins for an E1 deleted adenovirus). In one embodiment, the helper virus is an adenovirus. In one embodiment, the adenoviral vector may be replication incompetent as a result of harboring a temperature sensitive mutation. For example, an adenoviral vector comprising the ts369 mutation (Hasson, T. B. et al., *J Virol* 63(9):3612-21 (1989)) is replication compromised when cultured at 40° C. but can be rescued by culturing at lower temperatures. In one embodiment, 1) cells are infected at the non-permissive temperature with a temperature sensitive adenoviral vector coding for an antibody that will be displayed on the cell surface; 2) cells displaying antibodies with desired binding properties are selected; 3) virus is rescued from the selected cells by culturing said cells at a temperature permissive for viral replication.

In one embodiment, the viral vector encodes the heavy chain of an antibody or a fragment thereof. In another embodiment, the viral vector additionally encodes a light chain of an antibody or a fragment thereof, and is therefore capable of expressing, both heavy and light chain antibody polypeptides. In this embodiment, both the heavy and light chains are displayed together on the cell surface. In one embodiment, the heavy and light chains are displayed as a whole antibody on the cell surface. In another embodiment, the heavy and light chains are displayed as an antibody fragment on the cell surface. In one embodiment, the light chain is placed 5' (upstream) of the heavy chain coding sequence. Not wishing to be bound by theory, this may avoid an excess of toxic free heavy chain (Proudfoot, 1986, *Nature,* 322:562-565; and Kohler, 1980, *Proc. Natl. Acad. Sci. USA,* 77:2 197). The coding sequences for the heavy and light chains may comprise cDNA or genomic DNA.

In one embodiment, the nucleic acid of the viral vector further comprises a coding region for a selectable marker. A number of selection systems/markers may be used, including but not limited to, the herpes simplex virus thymidine kinase (Wigler et al, *Cell* 11:223 (1977)), hypoxanthineguanine phosphoribosyltransferase (Szybalski & Szybalski, *Proc. Natl. Acad. Sci. USA* 48:202 (1992)), and adenine phosphoribosyltransferase (Lowy et al, *Cell* 22:8 17 (1980)) genes can be employed in tk-, hgprt- or aprt-cells, respectively. Also, antimetabolite resistance can be used as the basis of selection for the following genes: dhfr, which confers resistance to methotrexate (Wigler et al, *Natl. Acad. Sci. USA* 77:357 (1980); OHare et al, Proc. Natl. Acad. Sci. USA 78:1527 (1981)); gpt, which confers resistance to mycophenolic acid (Mulligan & Berg, *Proc. Natl. Acad. Sci. USA* 78:2072 (1981)); neo, which confers resistance to the aminoglycoside G-418 (*Clinical Pharmacy* 12:488-505; Wu and Wu, *Biotherapy* 3:87-95 (1991); Tolstoshev, *Ann. Rev. Pharmacol. Toxicol.* 32:573-596 (1993); Mulligan, *Science* 260:926-932 (1993); and Morgan and Anderson, *Ann. Rev. Biochem.* 62: 191-217 (1993); *TIB TECH* 11:155-215 (May 1993)); and hygro, which confers resistance to hygromycin (Santerre et al., *Gene* 30:147 (1984)). Methods commonly known in the art of recombinant DNA technology may be routinely applied to select the desired recombinant clone, and such methods are described, for example, in Sambrook et al., (eds.), Molecular Cloning: A Laboratory Manual, Cold Spring Harbor Laboratory Press, NY, (2001); Ausubel et al. (eds.), Current Protocols in Molecular Biology, John Wiley & Sons, NY (1998); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1999); Colberre-Garapin et al, 1981, *J. Mol. Biol.* 150:1.

As described herein, in one embodiment, the whole recombinant antibody molecule, is expressed. In another embodiment, fragments (e.g., Fab fragments, F(ab') fragments, and epitope-binding fragments) of the immunoglobulin molecule are expressed.

7.2 Nucleic Acids

When the library of sequences coding for an antibody or antibody fragment is expressed, the antibody or antibody fragment is the bound to the cell surface. To accomplish this the nucleic acids of the viral vector library comprises at least two operatively linked coding regions see, e.g., FIG. 1. The first coding region codes for the an antibody chain (e.g., the heavy chain) library. The second coding region codes for an amino acid sequence that anchors and/or binds to cell membrane. The first and second coding regions are in-frame and operatively linked so as one polypeptide is formed during translation. This results in a fusion protein comprising the heavy chain of an antibody or antibody fragment and an amino acid sequence that anchors and/or binds to the cell membrane. In one embodiment, the first and second coding regions may be directly linked/adjacent to one another. In another embodiment, at least one codon is between or separates the first and second coding regions. In one embodiment, the at least one codon provides a linker or spacer sequence between the antibody chain (e.g., heavy chain) and the membrane anchoring/binding domain. In one embodiment, the second coding region codes for an amino acid sequence that anchors and/or binds to cell membrane, or codes for a transmembrane domain or a GPI-anchor.

With respect to the viral vector library, said first coding region of the library will be a genetically diverse repertoire of nucleic acid sequences which each encode a heavy chain of an antibody or antibody fragment. In one embodiment, the second coding region is the same throughout the library (e.g., a GPI-anchor domain from decay accelerating factor (DAF).

In one embodiment, the first coding region is operatively linked to a promoter. In one embodiment, the promoter is heterologous in relation to the viral vector. For example, the heterologous promoter is not derived from the same virus that the viral vector is derived from. In another embodiment, the promoter is not heterologous. For example, the promoter is derived from the same virus as the viral vector is derived from.

The promoter can essentially be any promoter that is active or can be induced to be active in the chosen cell. Although, the type of viral vector may influence the selection of promoters. For example, it is desirable to avoid promoters that may interfere with the particular viral vector. For example, copies of the same promoter in an adenoviral vector may lead to homologous recombination during replication of the vector (e.g., see Stecher et al., 2003, Methods Mol Med. 76:135-52; Carlson et al., 2002, Methods Enzymol. 346:277-92) Conversely, it is desirable to avoid promoters, where a particular viral vector may interfere with the promoter (e.g., see Grave et al., 2000, J Gene Med. 2:433-43).

Promoters which may be used to control the expression of the first coding region encoding an antibody heavy chain or fragment include, but are not limited to, the SV40 early promoter region (Bernoist and Chambon, 1981, Nature 290:304-310), a CMV promoter, the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42), the tetracycline (Tet) promoter (Gossen et al., 1995, Proc. Nat. Acad. Sci. USA 89:5547-5551); the ADC (alcohol dehydrogenase) promoter, PGK (phosphoglycerol kinase) promoter, alkaline phosphatase promoter, the immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286); neuronal-specific enolase (NSE) which is active in neuronal cells (Morelli et al., 1999, Gen. Virol. 80:571-83); brain-derived neurotrophic factor (BDNF) gene control region which is active in neuronal cells (Tabuchi et al., 1998, Biochem. Biophysic. Res. Corn. 253:818-823); glial fibrillary acidic protein (GFAP) promoter which is active in astrocytes (Gomes et al., 1999, Braz J Med Biol Res 32(5): 619-631; Morelli et al., 1999, Gen. Virol. 80:571-83) and gonadotropic releasing hormone gene control region which is active in the hypothalamus (Mason et al., 1986, Science 234:1372-1378).

In one embodiment, a polyadenylation signal is located 3' to and operatively linked to the second coding region. Essentially any polyadenylation signal that is active in the particular cell type containing the nucleic acid may be utilized. Although, the type of viral vector may influence the selection of polyadenylation signal. Polyadenylation signals that may find use with the present invention include, but are not limited to, those from SV40 and the bovine growth hormone gene.

In one embodiment, the nucleic acid also comprises a coding region for an amino terminus signal peptide sequence located upstream (5') of and operatively linked to the first coding region. Without wishing to be limited by theoretical considerations, the signal peptide directs the protein for initial transfer into the endoplasmic reticulum (ER). In one embodiment, the signal sequence at the amino terminus of the protein is cleaved during post-translational processing of the protein. In one embodiment, a native signal sequence is retained. In another embodiment, the native signal sequence is deleted and replaced with a heterologous signal sequence. The heterologous signal sequence selected should be one that is recognized and optionally processed (i.e. cleaved by a signal peptidase) by the particular host cell.

In one embodiment, the viral vector nucleic acid further comprises a coding sequence for an antibody light chain or fragment of an antibody light chain. As shown in FIGS. 1C and 1E, the light chain coding sequence can be operatively linked to a promoter different from the promoter operative linked to the heavy chain coding sequence. In other words, the expression of the light chain is not directly linked to the expression of the heavy chain. In another embodiment, as shown in Examples IV and VI of FIG. 1, the light chain coding sequence is operatively linked to the same promoter as the heavy chain coding sequence by either an internal ribosome entry site (IRES) or a self-processing cleavage sequence.

The vectors depicted in examples I-VI of FIG. 1A-C depict nonlimiting examples of viral vector constructs of the invention.

7.3 Viral Vector Library Construction

Viral vector libraries of the present invention can be constructed by any number of methods know to those skilled in the art. Essentially any antibody library can be cloned into a viral vector and be utilized in accordance with the present invention. Briefly, a library of nucleic acids coding for a diverse repertoire of nucleic acid sequences which each encode a heavy chain of an antibody or antibody fragment are isolated. For example, the repertoire of nucleic acid sequences coding for an antibody heavy chain can be isolated from, but not limited to, an antibody cDNA library, a cDNA library generated from nucleic acids, e.g., poly A+ RNA, isolated from any tissue or cells expressing antibodies. The repertoire of coding sequences can then be amplified, for example by PCR, and cloned into viral vectors (e.g. replicable viral vectors) using standard methods known in the art. Libraries of antibody coding sequences are also commercially available. In one embodiment, the library is constructed using coding regions from human antibodies. In some embodiments, the library expresses at least 100, $10^3$, $10^4$, $10^5$, $10^6$, $5\times10^6$, $10^7$, $5\times10^7$, $10^8$, $5\times10^8$, $10^9$, $5\times10^9$, $10^{10}$, $5\times10^{10}$, $10^{11}$, $5\times10^{11}$ or $10^{12}$ different antibodies.

Once a library of nucleic acids coding for an antibody heavy chain is obtained, it is cloned into a viral vector. Essentially any methods known for cloning nucleic acids into a viral vector can be utilized. These methods include, but are not limited to, restriction enzyme digestion and ligation, per SOEing (Horton, et al., 1989, *Gene*, 77, 61-68) or recombination. In one embodiment, the viral vector is an adenoviral vector and the cloning method is recombination. Recombination can be performed by any method known in the art. In one embodiment, the BJ5183 recombination method/system is utilized (for examples see PCT Patent Publication Nos. WO 02/067861 and WO 96/17070). Briefly, the library of coding regions is cloned into a plasmid resulting in the coding regions being flanked by sequences homologous to the region of insertion into the adenoviral vector. The plasmid library is co-transformed into BJ5183 cells with a compatible adenoviral vector plasmid. Full-length adenoviral vector plasmids containing the insertion are isolated and transfected into mammalian cells to produce the adenoviral vector library.

Another recombination method for constructing an adenoviral vector library utilizes the Gateway® system from Invitrogen (Carlsbad, Calif.), for example using the ViraPower™ Adenoviral Gateway® Vectors. This system uses a plasmid that contains the complete DNA sequence of an adenoviral vector. The adenoviral vector contains deletions in the E1 and E3 coding regions. The adenoviral vector can be propagated in 293A cells (Invitrogen, CA) that express the E1 proteins. E3 is a nonessential region for adenovirus replication in vitro.

Protocols for cloning nucleic acids into this system are available from Invitrogen. Briefly and by way of example, a method for constructing an adenoviral vector library using this system is described as follows. The library of nucleic acids is cloned into an entry vector creating an entry clone. Entry vectors include, but are not limited to, pENTR™/D-TOPO®; pENTR™/SD/D-TOPO®; pENTR™/TEV/D-TOPO®; pENTR™1A; pENTR™2B; pENTR™3C; pENTR™4; and pENTR™11 (all available from Invitrogen, CA). These vectors contain a multiple cloning site (MCS) flanked by recombination sites (e.g., attR1 and attR2). The library of nucleic acids is cloned into the MCS, which results in the individual library sequences being flanked by the recombination sites. The next step is to clone the library from the entry vector into an adenoviral vector plasmid (e.g., pAd/PL-DEST™ or pAd/CMV/V5-PL-DEST™ (both available from Invitrogen)). This cloning step utilizes recombination between the recombination sites in the entry vector and those in the adenoviral vector plasmid to create an adenoviral vector plasmid library. To produce the viral vector particles the recombined adenoviral vector plasmid library is digested with PacI and transfected into the 293A cells. The virus is then amplified and optionally purified, creating a stock of an adenoviral vector library. For further details see the following Invitrogen™ instruction manuals: pAd/CMV/V5-PL-DEST™ and pAd/PL-DEST™ Gateway® Vectors, Version D, Sep. 28, 2005; ViraPower™ Adenoviral Expression System, Version B, Jul. 11, 2005.

The methods of screening cells displaying antibodies as described herein, can be utilized in combination with other antibody screening methods and/or systems. For example, one embodiment of the invention utilizes mammalian cells expressing a library of antibodies on the cell surface. This library can be from any source. It can be a large library isolated from human cells and essentially represent a complete human repertoire of antibodies variable regions from a subject or subjects. In another embodiment, the library may be isolated from a mouse (e.g. a mouse expressing human antibodies) that has been immunized with the antigen of interest. Therefore, the library is enriched for antibodies that bind the antigen of interest. In another embodiment, a phage display antibody library is screened against the antigen of interest. The antibody library for the present invention is then created from those phage that express an antibody that binds the antigen of interest. Again, the library is enriched for antibodies that bind the antigen of interest. In still another embodiment, an antibody library for the present invention is generated from a library of humanized antibody fragments. Humanized antibody fragments may be generated by any method known to one of skill in the art including, but not limited to, framework shuffling (e.g., PCT Publication WO 05/042743) and low homology humanization (e.g., PCT Publication WO 05/035575). In another embodiment, the library is a mutant CDR library derived from an antibody that binds the antigen of interest. A mutant CDR library is a library coding for antibodies that are CDR mutations of a parent antibody's CDR sequences. Mutant CDR include, but are not limited to, libraries created by mutating CDR amino acids that are determined to be contact residues by crystallographic studies (e.g., Dall'Acqua et al. 1996 *Biochemistry* 35:9667-76); libraries created by retaining one native CDR (e.g. the one believed to have the highest binding efficiency) and combining with a library of CDRs in place of the other 5 CDRs (e.g., Rader et al., 1998, *PNAS* 95:8910-15); a library created by "CDR walking" (e.g., Yang et al., 1995, *J Mol Biol* 254: 392-403; and a library created by a method of separately mutating each CDR of a parental antibody (e.g., Wu et al., 1998, *PNAS* 95:6037-42). Therefore, any library of antibodies may be used in accordance with the present invention to express the library on the cell membrane. In one embodiment, the library is an affinity maturation library derived from a parental antibody.

In one embodiment, a phage display antibody library is screened against the antigen of interest. The antibody library for the present invention is then created from those phage that express an antibody that binds the antigen of interest. In one embodiment, both the heavy chain and light chain variable regions from each selected phage are cloned into a viral vector (e.g. adenoviral vector), wherein each viral vector encodes a heavy and light chain. Therefore, the same heavy and light chain combinations are maintained. In another embodiment, the heavy chain and light chain variable regions are isolated and combined in a random matter. Therefore, theoretically the library comprises every combination of each preselected heavy chain variable sequence with each preselected light chain sequence. For example, if the initial phage screen resulted in 1,000 unique phage and antibody sequences, a library comprised of every combination of each preselected heavy chain variable sequence with each preselected light chain sequence would now account for $10^6$ possible unique antibody sequences that would be cloned into a viral vector of the invention. This method creates an even more diverse repertoire than the initial phage library. Additionally, the phage display method is limited to certain antibody fragments, whereas this method allows an initially selected screen in phage of antibody fragments and a subsequent screen of, for example, whole antibodies created from the variable region sequences isolated from the phage selection step. Examples of phage display methods that can be used to make the antibody libraries of the present invention include those disclosed in Brinkman et al., 1995, *J. Immunol. Methods* 182:41-50; Ames et al., 1995, *J. Immunol. Methods* 184:177-186; Kettleborough et al., 1994, *Eur. J. Immunol.* 24:952-958; Persic et al., 1997, *Gene* 187:9-18; Burton et al., 1994, *Advances in Immunology* 57:191-280; PCT Publication Nos. WO 90/02809, WO 91/10737, WO 92/01047, WO 92/18619, WO 93/11236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108.

For further details and methods for cloning antibody libraries see e.g., PCT Patent Publication WO 2005/063817; WO 95/15393; and Higuchi et al. 1997 *J Immunological Methods* 202:193-204.

7.4 Selection Strategies & Methods

Once a viral vector antibody library is constructed, it can be screened against at least one antigen of interest. It will be appreciated by those skilled in the art that numerous variations for screening may be made without departing from the invention as described herein.

Generally, cells are infected with the viral vector antibody library. An appropriate MOI will be used based on several factors including, but not limited to, the number of cells available; the number of cells that can or are desired to be screened; titer of the viral vector, the infectivity of the cells by the viral vector; and the toxicity of viral vector infection on the cells. Generally, the infection procedure, including the MOI, will be optimized prior to the screening of the library.

After infection cells are cultured to allow expression of the antibody library, which is displayed on the cell surface. The cells are then screened for those expressing an antibody that binds the antigen of interest or has desired characteristics (e.g., binding to Fc receptors). The cells can be screened by methods described herein and those known to one skilled in the art. Cells expressing antibodies with the desired properties are separated from the other cells.

At this point the nucleic acids encoding the positive antibodies may be isolated and used to express the corresponding antibodies for further characterization. Alternatively, the viral vectors expressing the desired antibodies can be isolated and put through another round of screening. In this second round of screening, the same or a different MOI may be utilized. In one embodiment, the second and subsequent rounds of screening utilize MOIs lower that the initial infection. In one embodiment, in each subsequent round of screening the MOI is decreased. Although applicants do no wish to be bound by mechanistic speculation, only a small percentage of unique individual members of the initial library will be selected in the initial screening method. The higher the initial MOI of the initial infection, may lead to a larger number of irrelevant antibodies being selected. This is because the initial infection with a high MOI will likely result in multiple viral vectors infecting and expressing an antibody in each cell. Therefore, the selected cell would only have to express one antibody that binds the antigen to be selected, but any other viral vectors expressing irrelevant antibodies in the same cell would also be selected. Therefore in most cases, it is desirable to perform at least a second round of selection using a lower MOI. In some embodiments of the invention, a second selection step utilizes an MOI of at most: $10^{-6}$, $10^{-5}$, $10^{-4}$, $10^{-3}$, 0.01, 0.05, 0.1, 0.2, 0.3, 0.4, 0.5, 0.6, 0.7, 0.8, 0.9, 1 or 10. Lower MOIs can be used to virtually guarantee that each cell is infected by 1 or less viral vectors. This eliminates "carry-over" sequences or viral vectors.

Once viral vectors encoding antibodies with the desired characteristics are identified, the coding regions for these antibodies can be cloned into other expression vectors/systems for further evaluation and/or the production of the antibodies. Selected antibodies can also be modified by methods known in the art and those described herein.

Once a library of cells expressing antibodies on the cell surface is constructed, the next step is to screen and select for the cells expressing an antibody that binds a desired antigen or to select for antibodies with a desired characteristic (e.g., altered binding affinity for an Fc receptor). This screening and selection step can be accomplished using any of a variety of techniques known in the art including those described herein. For example, the antigen of interest may be tagged (e.g. fluorescent marker) and used to bind to antibodies on the cell surface; thus labeling the cells expressing antibodies that bind to the antigen. Numerous fluorescent labels are known in the art and commercially available (see, e.g., *Molecular Probes Handbook of Fluorescent Probes and Research Chemicals*, R. P. Haugland, 9th ed., Molecular Probes, (OR, 2004)).

In one embodiment, the antigen is biotin-labeled. The cells bind the antigen and a label conjugated to streptavidin is used to label cells bound to the antigen. In one embodiment, PE-conjugated streptavidin is used. In one embodiment, the antigen comprises streptavidin and labeled biotin is used as the detection reagent. These labeled cells can be identified and isolated using techniques known in the art. For example in the case of a fluorescently tagged antigen, the cells can be separated/sorted, for example, by a flow cytometer and sorted based on fluorescence. For examples, see PCT Publication Nos. WO 04/014292, WO 03/094859, WO 04/069264, WO 04/028551, WO 03/004057, WO 03/040304, WO 00/78815, WO 02/070007 and WO 03/075957, U.S. Pat. Nos. 5,795,734, 6,248,326 and 6,472,403, Pecheur et al., 2002, *FASEB J.* 16: 1266-1268; Almed et al., 2002, *J. Histochemistry & Cytochemistry* 50:1371-1379. In another embodiment, fluorescent cells are observed using a fluorescent microscope and may be isolated directly using standard micromanipulation techniques such as a fine glass pipette, micropipettor or a micromanipulator. In another embodiment, the cells can be sorted/separated using beads (e.g., magnetic beads; see Chestnut et al., 1996, *J Immunological Methods* 193:17-27). For example, an antigen can be biotinylated, and cells expressing antibodies that bind to the antigen can be isolated using streptavidin-coated beads.

In one embodiment, the antigen is fluorescently labeled. In one embodiment the fluorescent label is selected from the group consisting of Aqua, Texas-Red, FITC, rhodamine, rhodamine derivatives, fluorescein, fluorescein derivatives, cascade blue, Cy5, phycoertythrin, GFP or a GFP derivative e.g., EGFP.

In one embodiment, the antigen is recombinantly produced and incorporates a peptide tag, e.g., FLAG, HIS tag, Antibodies to the peptide tag can be used to detect and sort/select for or exclude cells that bind the particular antigen.

More than one antigen may be utilized in the selection step, for example, if screening for antibodies that bind a first antigen but not a second antigen. In this case, a negative selection step could be carried out by sorting for cells expressing antibodies that do not bind the second antigen, followed by a positive selection step that sorts for antibodies that bind the first antigen. In one embodiment, the positive selection step is carried out prior to the negative selection step. In one embodiment, the positive and negative selection step is carried out essentially simultaneously. For example, first and second antigen is labeled with different fluorescent molecules. Both antigens are incubated together with the cells displaying the antibodies. The concentration of the antibodies may be optimized for this embodiment. The cells are then simultaneously sorted for those that bind the first, but not the second antigen (e.g., two-color FACS analysis). One skilled in the art, based on the teachings herein, can negatively and/or positively screen for binding to a multitude of antigens by employing consecutive screening/selection steps and by multi-color FACS analysis.

In some embodiments antibodies that bind to a particular cell type (target cell) can be selected. Such selections in relation to phage-displayed antibodies are described in e.g. Huts et al., 2001, *Cancer Immunol. Immunother.* 50:163-171. The target cells can be fixed or unfixed, which may for example, offer an opportunity to select antibodies that bind to cell surface antigens that are altered by fixation. A particular cell type can be selected with reference to the biological function to be screened/selected for in the process. An appropriate cell type would be one that antibodies with the desired biological function would be expected to bind. For example, if it is desired to isolate antibodies capable of inhibiting the proliferation of cancer cells, it would be expected that such antibodies could bind to cancer cells. Thus, it would be appropriate to initially select for antibodies that can bind to cancer cells. To select for antibodies that bind to cells, the cells displaying antibodies can be screened for binding to the target cell using conditions conducive to binding. For example, a biotin-conjugated antibody that binds to the target cells, but not to the cells expressing the antibodies, can be bound to streptavidin-coated magnetic beads. These beads are then used to immobilize the target cells. The antibody-expressing cells can be combined with the immobilized cells, and those that bind to the magnetic beads can be isolated. Selection for antibodies that bind to cells, rather than specific, known antigens, has the advantage that there is a possibility of selecting for antibodies that bind to previously unknown antigens displayed on a cell surface. Such an antigen need not be a protein and may comprise more than one cell surface molecule. A selection step for binding to a chosen kind of cells or a particular molecule can be repeated once or multiple times, for example, at least about 2, 3, 4, 5, 6, or 7 times. If desired, two or more different pre-selection steps can be performed either simultaneously or in succession. For example, antibodies that bind to two different kinds of cancer cells can be selected.

Optionally, further refinement can be achieved by one or more negative selection steps, which can be performed either before or after the positive selection step. For example, if selecting for antibodies that bind to cancer cells, the cells displaying antibodies can be allowed to bind non-cancerous cells (e.g. as described above), and antibodies that do not bind to these cells can be retained for further testing. Such a negative selection can eliminate at least some of the antibodies that bind nonspecifically to non-target cells. Alternatively, the non-target protein(s) (e.g. unrelated or similar antigen as compared to the target antigen) is affixed to a solid support and utilized in a negative selection step to eliminate antibody expressing cells that bind to the non-target protein(s). In another example, it may be desired to isolate antibodies to a certain receptor, wherein this receptor is part of a family of receptors that have closely related structures. To increase the probability of isolating an antibody specific to this particular receptor, a negative selection step may be performed using one, some or all of the other receptors from the family. In a negative selection step, cells expressing antibodies that do not bind the non-target antigen can be retained for further testing. This selection can eliminate at least some of the antibodies that bind nonspecifically to the solid support or to a non-target protein(s). Similarly, if selecting for cells displaying antibodies that bind to a particular protein, the cells can be mixed with an unrelated or similar protein to compete for binding with the target protein.

Screening methods of the present invention may employ 1, 2, 3, 4, 5, 6, 7, 8 or more selection steps. The method used to perform secondary screens may depend on the viral vector being employed. Using an adenoviral vector for example, the viral vector can be directly isolated for subsequent rounds of screening/selection. For example, the cells (e.g. 293 based cells) are initially infected with the viral vector library followed by selection of cells that express antibodies that bind the antigen of interest. The cells are then lysed to release the packaged viral vectors. The cells can be lysed by any number of methods (e.g. freeze thawing the cells once or multiple times) that do not eliminate the infectivity of the viral vector. The cell lysate can be used directly for the infection in the next round of screening/selection or the viral vectors can be purified first.

In the case of adenoviral vectors, the MOI of infection, time of screening/sorting and time of isolating the viral vectors may need to be considered. For example, if the MOI is too high, the cells may lyse before the screening/sorting method. Additionally, if the screening/sorting step is performed to soon after the infection, the antibody may not yet be displayed on the cell surface or in sufficient quantity. If the screening step is performed too late, the cells may lyse from viral vector toxicity (e.g. replication). If the isolation of the vector is attempted too early, there may not be enough viral vector packaged. Adenoviral vectors have been used for decades for gene expression and optimizing these parameters are well within the skill of those in the art.

One skilled in the art can readily identify cells that could be used in accordance with the present invention. Cells that can be used for expressing the cell displayed antibodies include, but are not limited to, CHO, BHK, HeLa, COS, COST, MDCK, TM4, CV1, VERO, BRL 3A, Hep G2; MMT 060562; TRI; MRCS; FS4; NIH 3T3, W138, NS0, SP/20 and other lymphocytic cells, and human cells such as PERC6, HEK 293, 293A, breast cancer cell lines such as, for example, BT483, Hs578T, HTB2, BT20 and T47D, and normal mammary gland cell line such as, for example, CRL7030 and HsS78Bst. In one embodiment the cells are a 293 derivative. In one embodiment, the cells express at least one E1 adenoviral protein and the E1 coding region is integrated into the cellular genome.

When cells and/or viral vectors expressing antibodies with the desired properties are identified in the preceding steps, nucleic acids encoding them can be isolated and retested to ensure that they encode antibodies with the desired biological properties. If individual transformants or pools of transformants are isolated, recombinant nucleic acids can be obtained from these for retesting. For example, if individual transformants have been isolated, nucleic acids encoding the antibodies can be purified and used to transfect mammalian cells, which can then be characterized with regards to their binding properties for the antigen. If pools of transformants have been isolated, nucleic acids encoding the antibodies from pools testing positive can be used to transform cells to generate individual transformants expressing one antibody.

Nucleic acids encoding the antibodies from these individual transformants can be used to transfect cells and antibodies can be expressed, isolated and tested for function, thereby identifying proteins or antibodies having the desired function. If individual transformants or pools of transformants have not been isolated, nucleic acids encoding the protein or at least the antibody variable regions can be obtained from the transfectants or pools of transfectants that have tested positive, for example, by amplifying the expressed antibody variable region-encoding sequences by PCR. These sequences, which may be amplified by PCR, can also then be re-inserted into a suitable vector and used to generate individual transformants. Recombinant DNA from these transformants can be used to transfect mammalian cells in order express the antibodies and to retest for function.

7.5 Screening Based on Characteristics of Fc Receptor/Ligand Binding and/or Antibody Dependent Cell-Mediated Cytotoxicity (ADCC) and/or Complement Dependent Cytotoxicity (CDC)

The Fc region of an antibody interacts with a number of ligands including Fc receptors and other ligands, imparting an array of important functional capabilities referred to as effector functions. An important family of Fc receptors for the IgG class is the Fc gamma receptors (FcγRs). These receptors mediate communication between antibodies and the cellular arm of the immune system (Raghavan et al., 1996, Annu Rev Cell Dev Biol 12:181-220; Ravetch et al., 2001, Annu Rev Immunol 19:275-290). In humans this protein family includes FcγRI (CID64), including isoforms FcγRIA, FcγRIB, and FcγRIC; FcγRII (CD32), including isoforms FcγRIIA, FcγRIIB, and FcγRIIC; and FcγRIII (CID16), including isoforms FcγRIIIA and FcγRIIIB (Jefferis et al., 2002, Immunol Lett 82:57-65). These receptors typically have an extracellular domain that mediates binding to Fc, a membrane spanning region, and an intracellular domain that may mediate signaling events within the cell. Different FcγR subtypes are expressed on different cell types (reviewed in Ravetch et al., 1991, Annu Rev Immunol 9:457-492). For example, in humans, FcγRIIIB is found only on neutrophils, whereas FcγRIIIA is found on macrophages, monocytes, natural killer (NK) cells, and a subpopulation of T-cells.

Formation of the Fc/FcγR complex recruits effector cells to sites of bound antigen, typically resulting in signaling events within the cells and important subsequent immune responses such as release of inflammation mediators, B cell activation, endocytosis, phagocytosis, and cytotoxic attack. The ability to mediate cytotoxic and phagocytic effector functions is a potential mechanism by which antibodies destroy targeted cells. The cell-mediated reaction wherein nonspecific cytotoxic cells that express FcγRs recognize bound antibody on a target cell and subsequently cause lysis of the target cell is referred to as antibody dependent cell-mediated cytotoxicity (ADCC) (Raghavan et al., 1996, Annu Rev Cell Dev Biol 12:181-220; Ghetie et al., 2000, Annu Rev Immunol 18:739-766; Ravetch et al., 2001, Annu Rev Immunol 19:275-290). Notably, the primary cells for mediating ADCC, NK cells, express only FcγRIIIA only, whereas monocytes express FcγRI, FcγRII and FcγRIII (Ravetch et al., 1991, ibid).

Another important Fc ligand is the complement protein C1q. Fc binding to C1q mediates a process called complement dependent cytotoxicity (CDC) (reviewed in Ward et al., 1995, Ther Immunol 2:77-94). C1q is capable of binding six antibodies, although binding to two IgGs is sufficient to activate the complement cascade. C1q forms a complex with the C1r and C1s serine proteases to form the C1 complex of the complement pathway.

All FcγRs bind the same region on the Fc of the IgG subclass, but with different affinities (e.g., FcγRI is a high affinity while FcγRII and FcγRIII are low affinity binders). Other differences between the FcγRs are mechanistic. For example, FcγRI, FcγRIIA/C, and FcγRIIIA are positive regulators of immune complex triggered activation, characterized by having an immunoreceptor tyrosine-based activation motif (ITAM) while FcγRIIB has an immunoreceptor tyrosine-based inhibition motif (ITIM) and is therefore inhibitory. Thus, the balance between activating and inhibiting receptors is an important consideration. For example, enhancing Fc binding to the positive regulators (e.g., FcγRIIIA) while leaving unchanged or even reducing Fc binding to the negative regulator FcγRIIB could result in optimized effector function such as enhanced ADCC mediated destruction of tumor cells. Another consideration is that Fc variants should be engineered such that the binding to FcγRs and/or C1q is modulated in the desired manner but so that they maintain their stability, solubility, structural integrity as well as their ability to interact with other important Fc ligands such as FcRn and proteins A and G.

Antibodies find utility in a number of applications including therapeutic uses. Depending on the application, the desired ADCC and/or CDC characteristics of the antibody may vary. For example, in diagnostic application (e.g. ELISA, Western Blot, etc.,) the ADCC and/or CDC activity of the antibody is usually irrelevant and has little effect upon the diagnostic application. In the case of using anti-tumor antigen antibodies, increased ADCC and/or CDC may be desired to increase the in vivo or even in vitro cytotoxicity and therefore increase the potency of the antibody in relation to killing the tumor cells. In applications, for example, where the antibody is used in vivo to as an antagonist or agonist, it may be desired to use antibodies with decreased, low or no CDC and/or ADCC activity. This is particularly true for those antibodies designed to deliver a drug (e.g., toxins and isotopes) to the target cell where the Fc/FcγR mediated effector functions bring healthy immune cells into the proximity of the deadly payload, resulting in depletion of normal lymphoid tissue along with the target cells (Hutchins et al., 1995, PNAS USA 92:11980-11984; White et al., 2001, Annu Rev Med 52:125-145). In these cases the use of Fc variants that poorly recruit complement or effector cells would be of tremendous benefit (see for example, Wu et al., 2000, Cell Immunol 200:16-26; Shields et al., 2001, J. Biol Chem 276:6591-6604; U.S. Pat. No. 6,194,551; U.S. Pat. No. 5,885,573 and PCT Patent Publication WO 04/029207). Accordingly, the present invention additionally provides methods of screening antibody libraries based on Fc receptor (e.g., FcγR) and/or Fc ligand (e.g., C1q) binding and/or effector function (e.g., ADCC activity). The present invention can be utilized to screen for antibodies and/or antibody variants with any of these characteristics or combinations thereof.

Various mutagenesis studies have been carried out on the Fc domain (See for example, Duncan et al., 1988, Nature 332:563-564; Lund et al., 1995, Faseb J 9:115-119; Lund et al., 1996, J Immunol 157:4963-4969; Armour et al., 1999, Eur J Immunol 29:2613-2624; Shields et al., 2001, J Biol Chem 276:6591-6604; Jefferis et al., 2002, Immunol Lett 82:57-65; Presta et al., 2002, Biochem Soc Trans 30:487-490; U.S. Pat. Nos. 5,624,821, 5,885,573 and PCT Patent Publication Nos. WO 00/42072, WO 99/58572 and WO 04/029207). While the vast majority of amino acid substitutions in the Fc domain reduce or ablate FcγR binding, some have resulted in higher affinity for FcγR. For examples of specific modifications/substitutions and/or novel amino acids within the Fc domains see: Ghetie et al., 1997, Nat Biotech. 15:637-40; Duncan et al, 1988, Nature 332:563-564; Lund et al., 1991, J. Immunol 147:2657-2662; Lund et al, 1992, Mol Immunol 29:53-59; Alegre et al, 1994, Transplantation 57:1537-1543; Hutchins et al., 1995, Proc Natl. Acad Sci USA 92:11980-11984; Jefferis et al, 1995, Immunol Lett. 44:111-117; Lund et al., 1995, Faseb J 9:115-119; Jefferis et al, 1996, Immunol Lett 54:101-104; Lund et al, 1996, J Immunol 157:4963-4969; Armour et al., 1999, Eur J Immunol 29:2613-2624; Idusogie et al, 2000, J Immunol 164:4178-4184; Reddy et al, 2000, J Immunol 164:1925-1933; Xu et al., 2000, *Cell Immunol* 200:16-26; Idusogie et al, 2001, *J Immunol* 166:2571-2575; Shields et al., 2001, *J Biol Chem* 276: 6591-6604; Jefferis et al, 2002, *Immunol Lett* 82:57-65; Presta et al., 2002, *Biochem Soc Trans* 30:487-490); U.S. Pat. Nos. 5,624,821; 5,885,573; 5,677,425; 6,165,745; 6,277,375; 5,869,046; 6,121,022; 5,624,821; 5,648,260; 6,194,551; 6,737,056; 6,821,505; 6,277,375; U.S. patent application Ser. Nos. 10/370,749; 11/203,253; 11/203,251 and PCT Publications WO 94/2935; WO 99/58572; WO 00/42072; WO 01/58957; WO 02/060919, WO 04/016750; WO 04/029207; WO 04/035752 and WO 05/040217.

Fc regions comprising at least one amino acid substitution (i.e., a non naturally occurring amino acid residue), deletion or insertion introduced at any position within the Fc region are referred to herein as "variant Fc regions". Polypeptides comprising variant Fc regions (e.g., antibodies or Fc fusion proteins) are referred to herein generally as "Fc variants" or more specifically as "Fc variant antibodies" and "Fc variant fusion proteins." It is contemplated that the cell surface display methods disclosed herein may be utilized for expressing and screening a library of antibodies with variant Fc regions.

Libraries comprising antibodies with variant Fc regions (also referred to herein as "Fc variant libraries") may be screened for the desired Fc related function or lack thereof in accordance with the present invention. In one embodiment, the library of Fc variants comprises antibodies containing the same variable regions or Fab regions. In some embodiments, the library contains variants of the hinge domain, CH3 domain, CH2 domain or any combination thereof.

Methods for constructing Fc variants and Fc variant antibody libraries are know in the art. For examples, see Patent Publication Nos. WO 05/0037000; WO 06/023420; and WO 06/023403. It is contemplated that an Fc variant library comprises Fc regions with at least one amino acid substitution, deletion or insertion introduced at any position within the Fc region. It is also contemplated that an Fc variant library may further comprise additional amino acid residue substitutions (i.e., a non naturally occurring amino acid residue), deletions or insertions at one or more positions outside of the Fc region. In certain embodiments, an Fc variant library comprises Fc regions with at least one non-naturally occurring amino acid residue at any position within the Fc region. In specific embodiments, an Fc variant library comprises Fc regions that comprise at one or more position within the Fc region each of the 19 non-naturally occurring amino acid residues. In other specific embodiments, the Fc variant library comprises Fc regions that comprise at one or more position within the Fc region a subset of non-naturally occurring amino acid residues. In still other embodiment, the Fc variant library comprises Fc region that comprise the insertion of one or more amino acid residue at one or more position.

Without wishing to be bound by any particular theory, the amino acid substitutions (i.e., a non naturally occurring amino acid residue), deletions and/or insertions of the invention modulate the ADCC and/or CDC activity of an antibody by altering one or more of the factors that influence downstream effector function, including but not limited to, the affinity of the antibody for its FcγRs and/or to C1q, ability to mediate cytotoxic effector and/or complement cascade functions, protein stability, antibody half life and recruitment of effector cells and/or molecules.

In one embodiment, the library comprises Fc variants with at least one amino acid residue substitution (i.e., a non naturally occurring amino acid residue), deletion or insertion at a position selected from the group consisting of amino acid residues: 230, 231, 232, 233, 234, 235, 236, 237, 238, 239, 240, 242, 246, 250, 251, 256, 257, 259, 260, 261, 265, 266, 269, 273, 274, 275, 277, 281, 282, 298, 327, 328, 329, 330, 332, 346, 347 and 348, wherein the numbering system is that of the EU index as set forth in Kabat et al. (1991, NIH Publication 91-3242, National Technical Information Service, Springfield, Va.).

In another embodiment of the invention, the Fc variant library comprises, Fc variants having each of the non naturally occurring amino acid residues, at one or more of the amino acid residues at: 230, 231, 232, 233, 234, 235, 236, 237, 238, 239, 240, 242, 246, 250, 251, 256, 257, 259, 260, 261, 265, 266, 269, 273, 274, 275, 277, 281, 282, 298, 327, 328, 329, 330, 332, 346 and 348, wherein the numbering system is that of the EU index as set forth in Kabat.

In one embodiment, the Fc variants of the library comprise at least one amino acid substitution (i.e., a non naturally occurring amino acid residue), deletion or insertion at a position selected from the group consisting of: 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 239, 240, 242, 246, 250, 251, 257, 259, 260, 261, 265, 269, 273, 274, 275, 277, 281, 282, 284, 287, 291, 298, 300, 302, 304, 306, 308, 310, 314, 316, 318, 319, 321, 323, 327, 328, 329, 330, 332 and 336, wherein the numbering of the residues in the Fc region is that of the EU index as set forth in Kabat. In one embodiment, the library comprises Fc variants comprising at least 2, or at least 3, or at least 4, or at least 5, or at least 6, or at least 7, or at least 8, or at least 9, or at least 10, or at least 20, or at least 30, or at least 40, or at least 50, or at least 60, or at least 70, or at least 80, or at least 90, or at least 100, or at least 200 amino acid residues in the Fc region.

In one embodiment, the Fc variants of the library comprise at least one insertion after a position selected from the group consisting of amino acid residues: 230, 231, 232, 233, 234, 235, 236, 237, 238, 239, 240, 242, 246, 250, 251, 256, 257, 259, 260, 261, 265, 266, 269, 273, 274, 275, 277, 281, 282, 298, 327, 328, 329, 330, 332, 346 and 348, wherein the numbering system is that of the EU index as set forth in Kabat. The insertion may be any amino acid residue. In certain embodiments an Fc variant of the invention may comprises the insertion of more than one amino acid residue after a selected position. In certain other embodiments, an Fc variant of the invention may comprises the insertion of one or more amino acid residues after multiple positions.

In a specific embodiment, the Fc variants of the library comprise at least one insertion after a position selected from the group consisting of amino acid residues: 230, 231, 232, 233, 234, 235, 236, 237, 238, 239 and 240, wherein the numbering system is that of the EU index as set forth in Kabat. The insertion may be any amino acid residue. In certain embodiments an Fc variant of the invention may comprises the insertion of more than one amino acid residue after a selected position. In certain other embodiments, an Fc variant of the invention may comprises the insertion of one or more amino acid residues after multiple positions.

In other embodiments, the Fc variants of the library comprise a combination of a substitution and an insertion. In other embodiments, the Fc variants of the library comprise a combination of one or more of the substitutions and one or more of the insertions.

The present invention also provides Fc variants comprising at least one amino acid residue substitution (i.e., a non naturally occurring amino acid residue), deletion or insertion at a position selected from the group consisting of amino acid residues: 230, 231, 232, 233, 234, 235, 236, 237, 238, 239, 240, 242, 246, 250, 251, 256, 257, 259, 260, 261, 265, 266, 269, 273, 274, 275, 277, 281, 282, 298, 327, 328, 329, 330, 332, 346 and 348, wherein the numbering system is that of the EU index as set forth in Kabat.

In certain embodiments, an Fc variant of the present invention comprises at least one non naturally occurring amino acid residue selected from the group consisting of: 231L, 231I, 231V, 231N, 231Q, 231T, 231S, 232K, 232R, 234K, 234R, 235V, 235I, 235A, 235G, 236K, 236R, 236L, 236I, 236V, 236A, 237R, 237K, 238N, 238Q, 238V, 238L, 238I, 238E, 238D, 238A, 238G, 238M, 238C, 239D, 240G, 240A, 240H, 240D, 240E, 246R, 246E, 246D, 246W, 246F, 246M, 246C, 250S, 250V, 250I, 250L, 251A, 251G, 251E, 251D, 251V, 251I, 256R, 256K, 260R, 260K, 260E, 260D, 261S, 261T, 266A, 266G, 274R, 277V, 277I, 277L, 277S, 277T, 281S, 281T, 282F, 282W, 346R, 346K, 348G and 348A, wherein the numbering system is that of the EU index as set forth in Kabat.

In a specific embodiment, an Fc variant of the present invention comprises at least one non naturally occurring amino acid residues selected from the group consisting of: 231L, 231N, 231T, 232K, 234R, 235V, 235A, 235I, 236R, 236V, 236A, 237R, 237G 238N, 238V, 238E, 238L, 238G, 238M, 238Q, 239D, 240G, 240H, 240E, 246R, 246E, 246W, 246M, 250S, 250V, 251A, 251E, 251I, 256R, 260R, 260E, 261S, 265, 266A, 274R, 277V, 277T, 281S, 282F, 346R and 348A, wherein the numbering system is that of the EU index as set forth in Kabat.

In another specific embodiment, an Fc variant of the present invention comprises at least one non naturally occurring amino acid residues selected from the group consisting of: 198T, 234R, 236R, 236A, 237R, 238L, 238E, 238N, 238V, 238Q, 240E, 240G, 248E, 251A, 251E, 266A, 277T. In yet another specific embodiment, an Fc variant of the present invention comprises at least one combination of non naturally occurring amino acid residues selected from the group consisting of: 246R/251E/260R, 240G/198T, 237R/236A.

In certain embodiments, an Fc variant of the present invention comprises at least one insertion after a position selected from the group consisting of amino acid residues: 230, 231, 232, 233, 234, 235, 236, 237, 238, 239, 240, 242, 246, 250, 251, 256, 257, 259, 260, 261, 265, 266, 269, 273, 274, 275, 277, 281, 282, 298, 327, 328, 329, 330, 332, 346 and 348, wherein the numbering system is that of the EU index as set forth in Kabat. The insertion may be any amino acid residue. Specific insertions may be identified herein as "In" followed by the one letter code of the inserted amino acid residue and the position of the residues immediately flanking the insertion. For example "InG231/232" denotes a variant Fc comprising an insertion of a glycine between residues 231 and 232. In certain embodiments an Fc variant of the invention may comprises the insertion of more than one amino acid residue after a selected position. In certain other embodiments, an Fc variant of the invention may comprises the insertion of one or more amino acid residues after multiple positions.

In a specific embodiment, an Fc variant of the present invention comprises an insertion after a position selected from the group consisting of amino acid residues: 230, 231, 232, 233, 234, 235, 236, 237, 238, 239 and 240, wherein the numbering system is that of the EU index as set forth in Kabat. The insertion may be any amino acid residue. In certain embodiments an Fc variant of the invention may comprises the insertion of more than one amino acid residue after a selected position. In certain other embodiments, an Fc variant of the invention may comprises the insertion of one or more amino acid residues after multiple positions.

In another specific embodiment, an Fc variant of the present invention comprises at least one of the following insertions: InR234/235; InV235/236; InR236/237; InR237/238; InV238/239; InN238/239; InL238/239; InE238/239; InG238/239; InS239/240; InG240/241 and InE240/241.

In certain embodiments, an Fc variant of the present invention may comprise a combination of a substitution and an insertion. In other embodiments, an Fc variant of the present invention may comprise a combination of one or more of the substitutions and one or more of the insertions disclosed herein. In a specific embodiment, an Fc variant of the present invention comprises at least one of the following combinations of insertions and substitutions: InG240/241/I198T, InL238/239/P238Q, InE238/239/V348A, InS239/240/V266A, and InR237/238/G236A.

In one embodiment, the Fc variants of the present invention may be combined with other known Fc variants such as those disclosed in U.S. Pat. Nos. 5,624,821; 5,885,573; 5,677,425; 6,165,745; 6,277,375; 5,869,046; 6,121,022; 5,624,821; 5,648,260; 6,194,551; 6,737,056; 6,821,505; 6,277,375; U.S. patent application Ser. Nos. 10/370,749; 11/203,253; 11/203, 251 and PCT Publications WO 94/2935; WO 99/58572; WO 00/42072; WO 01/58957; WO 02/060919, WO 04/016750; WO 04/029207; WO 04/035752 and WO 05/040217.

It will be apparent to one skilled in the art that in addition to the specific amino acid residues described above, a number of additional amino acid residues may be inserted, deleted and/or substituted in the hinge to change the characteristics of the hinge. Families of amino acid residues having similar properties have been defined in the art and several examples are shown in Table 1.

TABLE 1

Properties of Amino Acid Residues.

| Family | Amino Acids |
| --- | --- |
| non-polar (hydrophobic) | Trp, Phe, Met, Leu, Ile, Val, Ala, Pro, Gly, |
| uncharged polar (hydrophilic) | Ser, Thr, Asn, Gln, Tyr, Cys |
| acidic/negatively charged | Asp, Glu |
| basic/positively charged | Arg, Lys, His |
| Beta-branched | Thr, Val, Ile |
| residues that influence chain orientation | Gly, Pro |
| aromatic | Trp, Tyr, Phe, His |

It is specifically contemplated that conservative amino acid substitutions may be made for said modifications of the hinge, described supra. It is well known in the art that "conservative amino acid substitution" refers to amino acid substitutions that substitute functionally equivalent amino acids. Conservative amino acid changes result in silent changes in the amino acid sequence of the resulting peptide. For example, one or more amino acids of a similar polarity act as functional equivalents and result in a silent alteration within the amino acid sequence of the peptide. Substitutions that are charge neutral and which replace a residue with a smaller residue may also be considered "conservative substitutions" even if the residues are in different groups (e.g., replacement of phenylalanine with the smaller isoleucine). Families of amino acid residues having similar side chains have been defined in the art. Several families of conservative amino acid substitutions are shown in Table 1. (supra).

The term "conservative amino acid substitution" also refers to the use of amino acid analogs or variants. Guidance concerning how to make phenotypically silent amino acid substitutions is provided in Bowie et al., "Deciphering the Message in Protein Sequences: Tolerance to Amino Acid Substitutions," (1990, Science 247:1306-1310).

The invention further encompasses incorporation of unnatural amino acids in the modification of the hinge to generate the Fc variants of the invention. Such methods are known to those skilled in the art such as those using the natural biosynthetic machinery to allow incorporation of unnatural amino acids into proteins, see, e.g., Wang et al., 2002 Chem. Comm. 1:1-11; Wang et al., 2001, Science, 292: 498-500; van Hest et al., 2001. Chem. Comm. 19: 1897-1904. Alternative strategies focus on the enzymes responsible for the biosynthesis of amino acyl-tRNA, see, e.g., Tang et al., 2001, J. Am. Chem. 123(44): 11089-11090; Kiick et al., 2001, FEBS Lett. 505(3): 465.

One skilled in the art will understand that that the Fc variant library may be screened for those Fc variants having altered FcγR and/or C1q binding properties (examples of binding properties include but are not limited to, binding specificity, equilibrium dissociation constant ($K_D$), dissociation and association rates ($K_{off}$ and $K_{on}$ respectively), binding affinity and/or avidity) and that certain alterations are more or less desirable, relevant to the application for the antibodies. It is well known in the art that the equilibrium dissociation constant ($K_D$) is defined as $k_{off}/k_{on}$. It is generally understood that a binding molecule (e.g., an antibody) with a low $K_D$ is preferable to a binding molecule (e.g., an antibody) with a high $K_D$. However, in some instances the value of the $k_{on}$ or $k_{off}$ may be more relevant than the value of the $K_D$. One skilled in the art can determine which kinetic parameter is most important for a given antibody application. For example a modification that enhances Fc binding to one or more positive regulators (e.g., FcγRIIIA) while leaving unchanged or even reducing Fc binding to the negative regulator FcγRIIB should correlate with enhanced ADCC activity. Alternatively, a modification that reduced binding to one or more positive regulator and/or enhanced binding to FcγRIIB should correlate with reduced ADCC activity. Accordingly, the ratio of binding affinities (e.g., equilibrium dissociation constants ($K_D$)) can indicate if the ADCC activity of an Fc variant is enhanced or decreased. For example a decrease in the ratio of FcγRIIIA/FcγRIIB equilibrium dissociation constants ($K_D$), should correlate with improved ADCC activity, while an increase in the ratio should correlate with a decrease in ADCC activity. Additionally, modifications that enhance binding to C1q should correlate with enhanced CDC activity, while modifications that reduce binding to C1q should correlate with reduced or eliminated CDC activity.

In one embodiment of the invention, the cell displayed Fc variant library is screened for altered binding affinity for at least one Fc receptor/ligand (e.g., FcγRIIIA, FcγRIIB, C1q, etc.) relative to a polypeptide having the same amino acid sequence as the Fc variant except comprising an unmodified Fc region (referred to herein as a "comparable molecule"). Accordingly, the present invention also provides Fc variants (also referred to herein as "Fc variants of the invention") having an altered binding affinity for at least one Fc receptor/ligand (e.g., FcγRIIIA, FcγRIIB, C1q, etc.) relative to a comparable molecule.

There are various methods known in the art that could be used to screen for altered FcγR and/or C1q binding properties. In one embodiment, the FcγR (e.g. FcγRIIIA and/or FcγRIIB) and/or C1q to be used for screening is fluorescently labeled, for example using techniques well known in the art including but not limited to those described herein (see e.g., section entitled "Examples" infra). In one embodiment, the FcγR (e.g. FcγRIIIA and/or FcγRIIB) and/or C1q to be used for screening are a fusion with streptavidin and labeled biotin is used for labeling cells expressing Fc. The labels can be detected as described herein. In one embodiment, flow cytometry is used to sort/select antibody Fc regions with the desired characteristics. For example, fluorescently labeled FcγRIIIA can be used to screen for Fc regions of antibodies with altered binding affinities. For example, the cells can be sorted based on mean fluorescent, with cells with high or increased mean fluorescent being sorted as possible increased binding affinity or with cells with low or decreased mean fluorescent being sorted as possible decreased binding affinity. In one embodiment, another labeled antibody that binds all of the variant Fc antibodies (e.g., an anti-human IgG antibody) can also be used to normalize for total antibody Fc displayed on the cell surface. For example, the cells can first be sorted for cells bound by an anti-human IgG antibody and then sorted for cells that bind (positive selection) or those that do not bind (negative selection) FcγRIIIA In one embodiment, the cells can first be sorted for cells that bind (positive selection) or those that do not bind (negative selection) FcγRIIIA and then sorted for cells that bind an anti-human IgG antibody. In another embodiment, the cells that bind FcγRIIIA are labeled with a first fluorescent molecule and the cells that bind an anti-human IgG antibody are labeled with a second fluorescent antibody, wherein the cells are simultaneously sorted for those positive for binding both FcγRIIIA and the anti-human IgG antibody. In an alternative embodiment, the cells are simultaneously sorted for those negative (or with low binding affinity) for binding FcγRIIIA and positive for binding the anti-human IgG antibody.

In one embodiment of the invention, the cell displayed Fc variant library is screened for increased or high binding to FcγRIIIA In one embodiment of the invention, the cell displayed Fc variant library is screened for decreased or low binding affinity to FcγRIIIA In one embodiment, an Fc variant library of the invention is screened for an increased or high affinity for FcγRIIIA and an affinity for FcγRIIB that is unchanged, reduced or enhanced. In one embodiment, an Fc variant library of the invention is screened for 1) an increased or high affinity for FcγRIIIA; 2) an affinity for FcγRIIB that is unchanged, reduced, or increased and 3) an affinity for C1q that is unchanged, reduced, or increased. In another embodiment, an Fc variant library of the invention is screened for 1) a decreased affinity for FcγRIIIA; and 2) an affinity for FcγRIIB that is increased.

In one embodiment, an Fc variant library of the invention is screened for a ratio of FcγRIIIA/FcγRIIB equilibrium dissociation constants (KD) that is increased or high. In another embodiment, an Fc variant library of the invention is screened for ratio of FcγRIIIA/FcγRIIB equilibrium dissociation constants (KD), is decreased or low. In one embodiment of the invention, the cell displayed Fc variant library is screened for increased or high binding for FcγRIIB. In one embodiment of the invention, the cell displayed Fc variant library is screened for decreased or low binding for FcγRIIB. In one embodiment of the invention, the cell displayed Fc variant library is screened for decreased or low binding affinity for C1q. In one embodiment of the invention, the cell displayed Fc variant library is screened for increased or high binding affinity for C1q.

In one embodiment, an Fc variant of the invention has increased or high binding affinity to FcγRIIIA. In another embodiment of the invention, an Fc variant of the invention has decreased or low binding affinity to FcγRIIIA. In still another embodiment, an Fc variant of the invention has increased or high affinity for FcγRIIIA and an affinity for FcγRIIB that is unchanged, reduced or enhanced. In yet another embodiment, an Fc variant of the invention has 1) an increased or high affinity for FcγRIIIA; 2) an affinity for FcγRIIB that is unchanged, reduced, or increased and 3) an affinity for C1q that is unchanged, reduced, or increased. In another embodiments, an Fc variant of the invention has 1) a decreased affinity for FcγRIIIA; and 2) an affinity for FcγRIIB that is increased. In certain embodiments, the binding affinity of an Fc variant of the invention to FcγRIIIA and/or FcγRIIB and/or C1q is increased or decreased relative to a comparable molecule.

In one embodiment, an Fc variant of the invention has a ratio of FcγRIIIA/FcγRIIB equilibrium dissociation constants (KD) that is increased or high. In another embodiment, an Fc variant of the invention has ratio of FcγRIIIA/FcγRIIB equilibrium dissociation constants (KD), is decreased or low. In still another embodiment of the invention, an Fc variant of the invention has increased or high binding for FcγRIIB. In one embodiment of the invention, the Fc variant of the invention has decreased or low binding for FcγRIIB. In other embodiments of the invention, an Fc variant of the invention has decreased or low binding affinity for C1q. In still other embodiments of the invention, an Fc variant of the invention has increased or high binding affinity for C1q. In certain embodiments, the binding affinity of an Fc variant of the invention to FcγRIIIA and/or FcγRIIB and/or C1q is increased or decreased relative to a comparable molecule.

In a specific embodiment, an Fc variant of the invention has an affinity for an Fc receptor and/or ligand (e.g., FcγRIIIA, C1q) that is at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold greater than that of a comparable molecule. In other embodiments, an Fc variant of the invention has an affinity for an Fc receptor and/or ligand (e.g., FcγRIIIA, C1q) that is increased by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule.

In a specific embodiment, an Fc variant of the invention has an equilibrium dissociation constant ($K_D$) for an Fc receptor and/or ligand (e.g., FcγRIIIA, C1q) that is reduced by at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold, or at least 400 fold, or at least 600 fold, relative to a comparable molecule. In another specific embodiment, an Fc variant of the invention has an equilibrium dissociation constant ($K_D$) for an Fc receptor and/or ligand (e.g., FcγRIIIA, C1q) that is reduced by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule.

In a specific embodiment, an Fc variant of the invention has an affinity for an Fc receptor and/or ligand (e.g., FcγRIIIA, C1q) that is reduced by at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold, relative to a comparable molecule. In other embodiments, an Fc variant of the invention has an affinity for an Fc receptor and/or ligand (e.g., FcγRIIIA, C1q) that is decreased by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule.

In a specific embodiment, an Fc variant of the invention has an equilibrium dissociation constant ($K_D$) for an Fc receptor and/or ligand (e.g., FcγRIIIA, C1q) that is increased by at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold, or at least 400 fold, or at least 600 fold, relative to a comparable molecule. In another specific embodiment, an Fc variant of the invention has an equilibrium dissociation constant ($K_D$) for an Fc receptor and/or ligand (e.g., FcγRIIIA, C1q) that is increased by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule.

In some embodiments, the Fc variant antibody library is screened for increased or decreased ADCC and/or CDC relative to a comparable molecule. Accordingly, the present invention also provides Fc variants having increased or decreased ADCC and/or CDC relative to a comparable molecule.

In one embodiment of the invention, the cell displayed Fc variant library is screened for high, low, increase, decreased or essentially unchanged ADCC activity. In a specific embodiment, the cell displayed Fc variant library is screened for high or increased ADCC activity. In another specific embodiment, the cell displayed Fc variant library is screened for low or decreased ADCC activity. In still another specific embodiment, the cell displayed Fc variant library is screened for unchanged ADCC activity. In one embodiment of the invention, the cell displayed Fc variant library is screened for high, low, increase, decreased or essentially unchanged CDC activity. In a specific embodiment, the cell displayed Fc variant library is screened for high or increased CDC activity. In another specific embodiment, the cell displayed Fc variant library is screened for low or decreased CDC activity. In still another specific embodiment, the cell displayed Fc variant library is screened for unchanged CDC activity.

In one embodiment, an Fc variant of the invention has high or increased ADCC activity. In another embodiment, an Fc variant of the invention has low or decreased ADCC activity. In still another embodiment, an Fc variant of the invention has unchanged ADCC activity. In other embodiments, an Fc variant of the invention has high or increased CDC activity. In still other embodiments, an Fc variant of the invention has low or decreased CDC activity. In yet other embodiments, an Fc variant of the invention has unchanged CDC activity. In certain embodiments, ADCC and/or CDC of an Fc variant of the invention is increased, decreased or unchanged relative to a comparable molecule.

In a specific embodiment, an Fc variant of the invention has ADCC and/or CDC activity that is at least 2 fold, or at least 3 fold, or at least 5 fold, or at least 10 fold, or at least 50 fold, or at least 100 fold greater than that of a comparable molecule. In yet another embodiment, an Fc variant of the invention has ADCC and/or CDC activity that is increased by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule.

In another specific embodiment, an Fc variant of the invention has ADCC and/or CDC activity that is reduced by at least 2 fold, or at least 3 fold, or at least 5 fold, or at least 10 fold, or at least 50 fold, or at least 100 fold, relative to a comparable molecule. In yet another embodiment, an Fc variant of the invention has ADCC and/or CDC activity that is decreased by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule.

An Fc variant of the invention comprises an Fc region with at least one amino acid substitution, deletion or insertion, referred to herein as a "variant Fc region of the invention". It is contemplated that a variant Fc region of the invention can be incorporated into additional molecules, such as Fc fusion proteins or other antibodies, to modulate Fc receptor (e.g., FcγR) and/or Fc ligand (e.g., C1q) binding and/or effector function (e.g., ADCC activity). This may be accomplished "de novo" by combining a heterologous molecule with the variant Fc region of the invention. Alternatively, or optionally, this may be accomplished by modifying the Fc region of an Fc region-containing polypeptide to comprises the same amino acid substitution, deletion or insertion present in the variant Fc region of the invention. Accordingly, the present invention provides methods to modulate Fc receptor (e.g., FcγR) and/or Fc ligand (e.g., C1q) binding and/or effector function (e.g., ADCC activity) comprising introducing a variant Fc region of the invention into an Fc containing polypeptide. Methods for generating fusion proteins and introducing amino acid substitutions, deletions or insertions are well known in the art and include chemical synthesis and recombinant expression techniques. (see, e.g., *Current Protocols in Molecular Biology*, F. M. Ausubel et al., eds., John Wiley & Sons (NY, 1998); *Molecular Cloning: A Laboratory Manual*, 3nd Edition, J. Sambrook et al., eds., Cold Spring Harbor Laboratory Press (NY, 2001)).

In one embodiment, the present invention provides a method of generating an Fc variant with altered Fc receptor (e.g., FcγR) and/or Fc ligand (e.g., C1q) binding and/or effector function (e.g., ADCC activity) comprising introducing at least one amino acid residue substitution (i.e., a non naturally occurring amino acid residue), deletion or insertion at a position selected from the group consisting of amino acid residues: 230, 231, 232, 233, 234, 235, 236, 237, 238, 239, 240, 242, 246, 250, 251, 256, 257, 259, 260, 261, 265, 266, 269, 273, 274, 275, 277, 281, 282, 298, 327, 328, 329, 330, 332, 346, 347 and 348, wherein the numbering system is that of the EU index as set forth in Kabat.

In one embodiment, the present invention provides a method of generating an Fc variant with altered Fc receptor (e.g., FcγR) and/or Fc ligand (e.g., C1q) binding and/or effector function (e.g., ADCC activity) comprising introducing at least one amino acid residue substitution (i.e., a non naturally occurring amino acid residue), deletion or insertion at a position selected from the group consisting of amino acid residues: 230, 231, 232, 233, 234, 235, 236, 237, 238, 239, 240, 242, 246, 250, 251, 256, 257, 259, 260, 261, 265, 266, 269, 273, 274, 275, 277, 281, 282, 298, 327, 328, 329, 330, 332, 346 and 348, wherein the numbering system is that of the EU index as set forth in Kabat.

In another embodiment, the present invention provides a method of generating an Fc variant with altered Fc receptor and/or Fc ligand binding and/or effector function comprising introducing at least one non naturally occurring amino acid residue selected from the group consisting of: 231L, 231I, 231V, 231N, 231Q, 231T, 231S, 232K, 232R, 234K, 234R, 235V, 235I, 235A, 235G, 236K, 236R, 236L, 236I, 236V, 236A, 237R, 237K, 238N, 238Q, 238V, 238L, 238I, 238E, 238D, 238A, 238G, 238M, 238C, 239D, 240G, 240A, 240H, 240D, 240E, 246R, 246E, 246D, 246W, 246F, 246M, 246C, 250S, 250V, 250I, 250L, 251A, 251G, 251E, 251D, 251V, 251I, 256R, 256K, 260R, 260K, 260E, 260D, 261S, 261T, 266A, 266G, 274R, 277V, 277I, 277L, 277S, 277T, 281S, 281T, 282F, 282W, 346R, 346K, 348G and 348A, wherein the numbering system is that of the EU index as set forth in Kabat.

In a specific embodiment, the present invention provides a method of generating an Fc variant with altered Fc receptor and/or Fc ligand binding and/or effector function comprising introducing at least one non naturally occurring amino acid residues selected from the group consisting of: 231L, 231N, 231T, 232K, 234R, 235V, 235A, 235I, 236R, 236V, 236A, 237R, 237G 238N, 238V, 238E, 238L, 238G, 238M, 238Q, 239D, 240G, 240H, 240E, 246R, 246E, 246W, 246M, 250S, 250V, 251A, 251E, 251I, 256R, 260R, 260E, 261S, 265, 266A, 274R, 277V, 277T, 281S, 282F, 346R and 348A, wherein the numbering system is that of the EU index as set forth in Kabat.

In another specific embodiment, the present invention provides a method of generating an Fc variant with altered Fc receptor and/or Fc ligand binding and/or effector function comprising introducing at least one non naturally occurring amino acid residues selected from the group consisting of: 198T, 234R, 236R, 236A, 237R, 238L, 238E, 238N, 238V, 238Q, 240E, 240G, 248E, 251A, 251E, 266A, 277T. In yet another specific embodiment, an Fc variant of the present invention comprises at least one combination of non naturally occurring amino acid residues selected from the group consisting of: 246R/251E/260R, 240G/198T, 237R/236A.

In certain embodiments, the present invention provides a method of generating an Fc variant with altered Fc receptor and/or Fc ligand binding and/or effector function comprising introducing at least one insertion after a position selected from the group consisting of amino acid residues: 230, 231, 232, 233, 234, 235, 236, 237, 238, 239, 240, 242, 246, 250, 251, 256, 257, 259, 260, 261, 265, 266, 269, 273, 274, 275, 277, 281, 282, 298, 327, 328, 329, 330, 332, 346 and 348, wherein the numbering system is that of the EU index as set forth in Kabat. The insertion may be any amino acid residue. Specific insertions may be identified herein as "In" followed by the one letter code of the inserted amino acid residue and the position of the residues immediately flanking the insertion. For example "InG231/232" denotes a variant Fc comprising an insertion of a glycine between residues 231 and 232. In certain embodiments an Fc variant of the invention may comprises the insertion of more than one amino acid residue after a selected position. In certain other embodiments, an Fc variant of the invention may comprises the insertion of one or more amino acid residues after multiple positions.

In a specific embodiment, the present invention provides a method of generating an Fc variant with altered Fc receptor and/or Fc ligand binding and/or effector function comprising introducing at least one insertion after a position selected from the group consisting of amino acid residues: 230, 231, 232, 233, 234, 235, 236, 237, 238, 239 and 240, wherein the numbering system is that of the EU index as set forth in Kabat. The insertion may be any amino acid residue. In certain embodiments an Fc variant of the invention may comprises the insertion of more than one amino acid residue after a selected position. In certain other embodiments, an Fc variant of the invention may comprises the insertion of one or more amino acid residues after multiple positions.

In another specific embodiment, the present invention provides a method of generating an Fc variant with altered Fc receptor and/or Fc ligand binding and/or effector function comprising introducing at least one insertion selected from the group consisting of: InR234/235; InV235/236; InR236/237; InR237/238; InV238/239; InN238/239; InL238/239; InE238/239; InG238/239; InS239/240; InG240/241 and InE240/241.

In certain embodiments, the present invention provides a method of generating an Fc variant with altered Fc receptor and/or Fc ligand binding and/or effector function comprising introducing a combination a substitution and an insertion. In other embodiments, the present invention provides a method of generating an Fc variant with altered Fc receptor and/or Fc ligand binding and/or effector function comprising introducing combination of one or more of the substitutions and one or more of the insertions disclosed herein. In a specific embodiment, the present invention provides a method of generating an Fc variant with altered Fc receptor and/or Fc ligand binding and/or effector function comprising introducing at least one combinations of insertions and substitutions selected from the group consisting of: InG240/241/I198T, InL238/239/P238Q, InE238/239N348A, InS239/240N266A, and InR237/238/G236A.

7.6 Antibodies

Essentially all types of antibodies may be utilized in accordance with the invention. These include, but are not limited to, synthetic antibodies, monoclonal antibodies, recombinantly produced antibodies, intrabodies, multispecific antibodies, diabodies, bispecific antibodies, human antibodies, humanized antibodies, chimeric antibodies, synthetic antibodies, single-chain Fvs (scFv), Fab fragments, F(ab') fragments, disulfide-linked Fvs (sdFv), and anti-idiotypic (anti-Id) antibodies, and epitope-binding fragments of any of the above. Antibodies used in the methods of the present invention include immunoglobulin molecules and immunologically active portions of immunoglobulin molecules. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Antibodies or antibody fragments may be from any animal origin including birds and mammals (e.g., human, murine, donkey, sheep, rabbit, goat, guinea pig, camel, horse, or chicken). In one embodiment, the antibodies are human or humanized monoclonal antibodies. As used herein, "human" antibodies include antibodies having the amino acid sequence of a human immunoglobulin and include antibodies isolated from human immunoglobulin libraries or from mice that express antibodies from human genes. Antibodies or antibody fragments used in accordance with the present invention may be monospecific, bispecific, trispecific or of greater multi-specificity. Multispecific antibodies may specifically bind to different epitopes of desired target molecule or may specifically bind to both the target molecule as well as a heterologous epitope, such as a heterologous polypeptide or solid support material. See, e.g., PCT Publication Nos. WO 93/17715, WO 92/08802, WO 91/00360, and WO 92/05793; Tutt, et al., 1991, J. Immunol. 147:60-69; U.S. Pat. Nos. 4,474,893, 4,714,681, 4,925,648, 5,573,920, and 5,601,819; and Kostelny et al., 1992, J. Immunol. 148:1547-1553. The present invention may also be practiced with single domain antibodies, including camelized single domain antibodies (see e.g., Muyldermans et al., 2001, Trends Biochem. Sci. 26:230; Nuttall et al., 2000, Cur. Pharm. Biotech. 1:253; Reichmann and Muyldermans, 1999, J. Immunol. Meth. 231: 25; PCT Publication Nos. WO 94/04678 and WO 94/25591; U.S. Pat. No. 6,005,079).

Embodiments of the invention include antibodies that bind to any target. Antibodies may be from any species, be chimeric antibodies or humanized antibodies. In one embodiment, the antibodies are human antibodies. In one embodiment, the antibodies are humanized antibodies.

It is also contemplated that an Fc variant library may be generated from, or a variant Fc region of the invention may be introduced into an antibody already described in the art including but not limited to anti-fluorescein monoclonal antibody, 4-4-20 (Kranz et al., 1982 *J. Biol. Chem.* 257(12): 6987-6995), a humanized anti-TAG72 antibody (CC49) (Sha et al., 1994 *Cancer Biother.* 9(4): 341-9), an antibody that specifically bind an Eph Receptor including, but not limited to those disclosed in PCT Publication Nos. WO 04/014292, WO 03/094859 and U.S. patent application Ser. No. 10/863,729, antibodies that specifically bind Integrin $\alpha_v\beta_3$ including, but not limited to, LM609 (Scripps), the murine monoclonal LM609 (PCT Publication WO 89/015155 and U.S. Pat. No. 5,753,230); the humanized monoclonal antibody MEDI-522 (a.k.a. VITAXIN®, MedImmune, Inc., Gaithersburg, Md.; Wu et al., 1998, *PNAS USA* 95(11): 6037-6042; PCT Publications WO 90/33919 and WO 00/78815), an antibody against interferon alpha as disclosed in WO/2005/05059106, an antibody against the interferon receptor 1 as disclosed in WO/2006/059106, Erbitux™ (also known as IMC-C225) (ImClone Systems Inc.), a chimerized monoclonal antibody against EGFR; HERCEPTIN® (Trastuzumab) (Genentech, CA) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection. Other examples are a humanized anti-CD18 F(ab')$_2$ (Genentech); CDP860 which is a humanized anti-CD18 F(ab')$_2$ (Celltech, UK); PRO542 which is an anti-HIV gp120 antibody fused with CD4 (Progenics/Genzyme Transgenics); C14 which is an anti-CD14 antibody (ICOS Pharm); a humanized anti-VEGF IgG1 antibody (Genentech); OVAREX™ which is a murine anti-CA 125 antibody (Altarex); PANOREX™ which is a murine anti-17-IA cell surface antigen IgG2a antibody (Glaxo Wellcome/Centocor); IMC-C225 which is a chimeric anti-EGFR IgG antibody (ImClone System); VITAXIN™ which is a humanized anti-$\alpha V\beta 3$ integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); Smart ID10 which is a humanized anti-HLA antibody (Protein Design Lab); ONCOLYM™ (Lym-1) is a radiolabelled murine anti-HLA DR antibody (Techniclone); anti-CD11a is a humanized IgG1 antibody (Genetech/Xoma); ICM3 is a humanized anti-ICAM3 antibody (ICOS Pharm); IDEC-114 is a primatized anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-$\alpha$ IgG4 antibody (Celltech); LDP-02 is a humanized anti-$\alpha 4\beta 7$ antibody (LeukoSite/Genentech); Ortho-Clone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); MDX-33 is a human anti-CD64 (FcγR) antibody (Medarex/Centeon); rhuMab-E25 is a humanized anti-IgE IgG1 antibody (Genentech/Norvartis/Tanox Biosystems); IDEC-152 is a primatized anti-CD23 antibody (IDEC Pharm); ABX-CBL is a murine anti CD-147 IgM antibody (Abgenix); BTI-322 is a rat anti-CD2 IgG antibody (Medimmune/Bio Transplant); Orthoclone/OKT3 is a murine anti-CD3 IgG2a antibody (ortho Biotech); SIMULECT™ is a chimeric anti-CD25 IgG1 antibody (Novartis Pharm); LDP-01 is a humanized anti-$β_2$-integrin IgG antibody (LeukoSite); Anti-LFA-1 is a murine anti CD18 $F(ab')_2$ (Pasteur-Merieux/Immunotech); CAT-152 is a human anti-TGF-$β_2$ antibody (Cambridge Ab Tech); and Corsevin M is a chimeric anti-Factor VII antibody (Centocor).

Additional antibodies which may be utilized in accordance with the present invention may specifically bind a cancer or tumor antigen for example, including, but not limited to, KS ¼ pan-carcinoma antigen (Perez and Walker, 1990, *J. Immunol.* 142: 3662-3667; Bumal, 1988, *Hybridoma* 7(4): 407-415), ovarian carcinoma antigen (CA125) (Yu et al., 1991, *Cancer Res.* 51(2): 468-475), prostatic acid phosphate (Tailor et al., 1990, *Nucl. Acids Res.* 18(16): 4928), prostate specific antigen (Henttu and Vihko, 1989, Biochem. Biophys. Res. Comm. 160(2): 903-910; Israeli et al., 1993, Cancer Res. 53: 227-230), melanoma-associated antigen p97 (Estin et al., 1989, *J. Natl. Cancer Instit.* 81(6): 445-446), melanoma antigen gp75 (Vijayasardahl et al., 1990, *J. Exp. Med.* 171(4): 1375-1380), high molecular weight melanoma antigen (HMW-MAA) (Natali et al., 1987, *Cancer* 59: 55-63; Mittelman et al., 1990, *J. Clin. Invest.* 86: 2136-2144), prostate specific membrane antigen, carcinoembryonic antigen (CEA) (Foon et al., 1994, *Proc. Am. Soc. Clin. Oncol.* 13: 294), polymorphic epithelial mucin antigen, human milk fat globule antigen, colorectal tumor-associated antigens such as: CEA, TAG-72 (Yokata et al., 1992, *Cancer Res.* 52: 3402-3408), CO17-1A (Ragnhammar et al., 1993, *Int. J. Cancer* 53: 751-758); GICA 19-9 (Herlyn et al., 1982, *J. Clin. Immunol.* 2: 135), CTA-1 and LEA, Burkitt's lymphoma antigen-38.13, CD19 (Ghetie et al., 1994, *Blood* 83: 1329-1336), human B-lymphoma antigen-CD20 (Reff et al., 1994, *Blood* 83:435-445), CD33 (Sgouros et al., 1993, *J. Nucl. Med.* 34:422-430), melanoma specific antigens such as ganglioside GD2 (Saleh et al., 1993, *J. Immunol.*, 151, 3390-3398), ganglioside GD3 (Shitara et al., 1993, *Cancer Immunol. Immunother.* 36:373-380), ganglioside GM2 (Livingston et al., 1994, *J. Clin. Oncol.* 12: 1036-1044), ganglioside GM3 (Hoon et al., 1993, *Cancer Res.* 53: 5244-5250), tumor-specific transplantation type of cell-surface antigen (TSTA) such as virally-induced tumor antigens including T-antigen DNA tumor viruses and Envelope antigens of RNA tumor viruses, oncofetal antigen-alpha-fetoprotein such as CEA of colon, bladder tumor oncofetal antigen (Hellstrom et al., 1985, *Cancer. Res.* 45:2210-2188), differentiation antigen such as human lung carcinoma antigen L6, L20 (Hellstrom et al., 1986, *Cancer Res.* 46: 3917-3923), antigens of fibrosarcoma, human leukemia T cell antigen-Gp37 (Bhattacharya-Chatterjee et al., 1988, *J. of Immun.* 141:1398-1403), neoglycoprotein, sphingolipids, breast cancer antigen such as EGFR (Epidermal growth factor receptor), HER2 antigen ($p185^{HER2}$), polymorphic epithelial mucin (PEM) (Hilkens et al., 1992, *Trends in Bio. Chem. Sci.* 17:359), malignant human lymphocyte antigen-APO-1 (Bernhard et al., 1989, Science 245: 301-304), differentiation antigen (Feizi, 1985, Nature 314: 53-57) such as I antigen found in fetal erythrocytes, primary endoderm I antigen found in adult erythrocytes, preimplantation embryos, I(Ma) found in gastric adenocarcinomas, M18, M39 found in breast epithelium, SSEA-1 found in myeloid cells, VEP8, VEP9, Myl, VIM-D5, $D_1$56-22 found in colorectal cancer, TRA-1-85 (blood group H), C14 found in colonic adenocarcinoma, F3 found in lung adenocarcinoma, AH6 found in gastric cancer, Y hapten, Le found in embryonal carcinoma cells, TL5 (blood group A), EGF receptor found in A431 cells, $E_1$ series (blood group B) found in pancreatic cancer, FC10.2 found in embryonal carcinoma cells, gastric adenocarcinoma antigen, CO-514 (blood group $Le^a$) found in Adenocarcinoma, NS-10 found in adenocarcinomas, CO-43 (blood group $Le^b$), G49 found in EGF receptor of A431 cells, MH2 (blood group $ALe^b/Le^y$) found in colonic adenocarcinoma, 19.9 found in colon cancer, gastric cancer mucins, $T_5A_7$ found in myeloid cells, $R_{24}$ found in melanoma, 4.2, $G_{D3}$, D1.1, OFA-1, $G_{M2}$, OFA-2, $G_{D2}$, and M1:22:25:8 found in embryonal carcinoma cells, and SSEA-3 and SSEA-4 found in 4 to 8-cell stage embryos. In one embodiment, the antigen is a T cell receptor derived peptide from a Cutaneous Tcell Lymphoma (see, Edelson, 1998, *The Cancer Journal* 4:62).

7.7 Specific Antigens and Fusion Partners of the Invention

As described above, the methods of the present invention may be applied to any antibody. For example an Fc variant library may be generated from, or a variant Fc region of the invention may be introduced into any antibody. Furthermore, an variant Fc region of the invention may be utilized to generate an Fc fusion protein. Accordingly, virtually any molecule may be targeted by and/or incorporated into an antibody and/or Fc fusion protein which may be utilized in accordance with the present invention including, but not limited to, the following list of proteins, as well as subunits, domains, motifs and epitopes belonging to the following list of proteins: renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VII, factor VIIIC, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors such as, for example, EGFR, VEGFR; interferons such as alpha interferon (α-IFN), beta interferon (β-IFN) and gamma interferon (γ-IFN); interferon receptor components such as interferon receptor 1; protein A or D; rheumatoid factors; a neurotrophic factor such as bone-derived neurotrophic factor (BDNF), neurotrophin-3,-4,-5, or -6 (NT-3, NT-4, NT-5, or NT-6), or a nerve growth factor; platelet-derived growth factor (PDGF); fibroblast growth factor such as αFGF and βFGF; epidermal growth factor (EGF); transforming growth factor (TGF) such as TGF-alpha and TGF-beta, including TGF-1, TGF-2, TGF-3, TGF-4, or TGF-5; insulin-like growth factor-I and -II (IGF-I and IGF-II); des (1-3)-IGF-I (brain IGF-I), insulin-like growth factor binding proteins; CD proteins such as CD2, CD3, CD4, CD 8, CD11a, CD14, CD18, CD19, CD20, CD22, CD23, CD25, CD33, CD34, CD40, CD40L, CD52, CD63, CD64, CD80 and CD147; erythropoietin; osteoinductive factors; immunotoxins; a bone morphogenetic protein (BMP); an interferon such as interferon-alpha, -beta, and -gamma; colony stimulating factors (CSFs), such as M-CSF, GM-CSF, and G-CSF; interleukins (ILs), e.g., IL-1 to IL-13; TNFα, HMGB1; HMGB2; superoxide dismutase; T-cell receptors; surface membrane proteins; decay accelerating factor; viral antigen such as, for example, a portion of the AIDS envelope, e.g., gp120; transport proteins; homing receptors; addressins; regulatory proteins; cell adhesion molecules such as LFA-1, Mac 1, p150.95, VLA-4, ICAM-1, ICAM-3 and VCAM, a4/p7 integrin, and (Xv/p3 integrin including either a or subunits thereof, integrin alpha subunits such as CD49a, CD49b, CD49c, CD49d, CD49e, CD49f, alpha7, alpha8, alpha9, alphaD, CD11a, CD11b, CD51, CD11c, CD41, alpha11b, alphaIELb; integrin beta subunits such as, CD29, CD 18, CD61, CD104, beta5, beta6, beta7 and beta8; Integrin subunit combinations including but not limited to, αVβ3, αVβ5 and α4β7; a member of an apoptosis pathway; IgE; blood group antigens; flk2/flt3 receptor; obesity (OB) receptor; mpl receptor; CTLA-4; protein C; a chitinase or chitinase-like molecule such as YKL-40 and AMCase; an Eph receptor such as EphA2, EphA4, EphB2, etc.; a Human Leukocyte Antigen (HLA) such as HLA-DR; complement proteins such as complement receptor CR1, C1Rq and other complement factors such as C3, and C5; a glycoprotein receptor such as GpIbα, GPIIb/IIIa and CD200;

Additional, molecules which may be utilized in accordance with the present invention are those that specifically bind cancer antigens including, but not limited to, ALK receptor (pleiotrophin receptor), pleiotrophin, KS ¼ pan-carcinoma antigen; ovarian carcinoma antigen (CA125); prostatic acid phosphate; prostate specific antigen (PSA); melanoma-associated antigen p97; melanoma antigen gp75; high molecular weight melanoma antigen (HMW-MAA); prostate specific membrane antigen; carcinoembryonic antigen (CEA); polymorphic epithelial mucin antigen; human milk fat globule antigen; colorectal tumor-associated antigens such as: CEA, TAG-72, CO17-1A, GICA 19-9, CTA-1 and LEA; Burkitt's lymphoma antigen-38.13; CD19; human B-lymphoma antigen-CD20; CD33; melanoma specific antigens such as ganglioside GD2, ganglioside GD3, ganglioside GM2 and ganglioside GM3; tumor-specific transplantation type cell-surface antigen (TSTA); virally-induced tumor antigens including T-antigen, DNA tumor viruses and Envelope antigens of RNA tumor viruses; oncofetal antigen-alpha-fetoprotein such as CEA of colon, 5T4 oncofetal trophoblast glycoprotein and bladder tumor oncofetal antigen; differentiation antigen such as human lung carcinoma antigens L6 and L20; antigens of fibrosarcoma; human leukemia T cell antigen-Gp37; neoglycoprotein; sphingolipids; breast cancer antigens such as EGFR (Epidermal growth factor receptor); NY-BR-16; NY-BR-16 and HER2 antigen (p185$^{HER2}$); polymorphic epithelial mucin (PEM); malignant human lymphocyte antigen-APO-1; differentiation antigen such as I antigen found in fetal erythrocytes; primary endoderm I antigen found in adult erythrocytes; preimplantation embryos; I(Ma) found in gastric adenocarcinomas; M18, M39 found in breast epithelium; SSEA-1 found in myeloid cells; VEP8; VEP9; Myl; VIM-D5; $D_1$56-22 found in colorectal cancer; TRA-1-85 (blood group H); SCP-1 found in testis and ovarian cancer; C14 found in colonic adenocarcinoma; F3 found in lung adenocarcinoma; AH6 found in gastric cancer; Y hapten; Le$^y$ found in embryonal carcinoma cells; TL5 (blood group A); EGF receptor found in A431 cells; $E_1$ series (blood group B) found in pancreatic cancer; FC10.2 found in embryonal carcinoma cells; gastric adenocarcinoma antigen; CO-514 (blood group Le$^a$) found in Adenocarcinoma; NS-10 found in adenocarcinomas; CO-43 (blood group Le$^b$); G49 found in EGF receptor of A431 cells; MH2 (blood group ALe$^b$/Le$^y$) found in colonic adenocarcinoma; 19.9 found in colon cancer; gastric cancer mucins; $T_5A_7$ found in myeloid cells; $R_{24}$ found in melanoma; 4.2, $G_{D3}$, D1.1, OFA-1, $G_{M2}$, OFA-2, $G_{D2}$, and M1:22:25:8 found in embryonal carcinoma cells and SSEA-3 and SSEA-4 found in 4 to 8-cell stage embryos; Cutaneous T cell Lymphoma antigen; MART-1 antigen; Sialy Tn (STn) antigen; Colon cancer antigen NY-CO-45; Lung cancer antigen NY-LU-12 variant A; Adenocarcinoma antigen ART1; Paraneoplastic associated brain-testis-cancer antigen (onconeuronal antigen MA2; paraneoplastic neuronal antigen); Neuro-oncological ventral antigen 2 (NOVA2); Hepatocellular carcinoma antigen gene 520; TUMOR-ASSOCIATED ANTIGEN CO-029; Tumor-associated antigens MAGE-C1 (cancer/testis antigen CT7), MAGE-B1 (MAGE-XP antigen), MAGE-B2 (DAM6), MAGE-2, MAGE-4-a, MAGE-4-b and MAGE-X2; Cancer-Testis Antigen (NY-EOS-1); YKL-40 and fragments of any of the above-listed polypeptides.

7.8 Downstream Engineering

It is contemplated that one or more of the polypeptides isolated using the screening methods of the present invention may be further modified. For example, an antibody isolated in accordance with the present invention may be modified (i.e., by the covalent attachment of any type of molecule to the antibody such that covalent attachment). For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, etc. In certain embodiments antibodies, or fragments thereof, isolated in accordance with the present invention are fused to a bioactive molecule including, but not limited to, peptides, polypeptides, proteins, small molecules, mimetic agents, synthetic drugs, inorganic molecules, and organic molecules. In other embodiments antibodies, or fragments thereof, isolated in accordance with the present invention are conjugated to a diagnostic, detectable or therapeutic agent. Such agents and method for conjugation are well known to one of skill in the art and are disclosed in numerous sources (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, *Immunol. Rev.* 62:119; International Publication Nos. WO 93/15199; WO 93/15200; WO 97/33899; WO 97/34911; WO 01/77137; WO 03/075957; U.S. Patent Publications 2006/0040325). Alternatively or optionally, the antibody, or a fragment thereof, isolated in accordance with the present invention may be fused to a polypeptide moiety. Methods for fusing or conjugating antibodies to polypeptide moieties are known in the art. See, e.g., U.S. Pat. Nos. 5,336,603; 5,622,929; 5,359,046; 5,349,053; 5,447,851, and 5,112,946; EP 307,434; EP 367,166; PCT Publications WO 96/04388 and WO 91/06570; Ashkenazi et al., 1991, PNAS USA 88:10535; Zheng et al., 1995, J Immunol 154:5590; and Vil et al., 1992, PNAS USA 89:11337; each incorporated by reference in their entireties. The fusion of an antibody, or fragment thereof, to a moiety does not necessarily need to be direct, but may occur through linker sequences. Such linker molecules are commonly known in the art and described in Denardo et al., 1998, Clin Cancer Res 4:2483; Peterson et al., 1999, Bioconjug Chem 10:553; Zimmerman et al., 1999, Nucl Med Biol 26:943; Garnett, 2002, Adv Drug Deliv Rev 53:171.

In one embodiment, antibodies, or fragments thereof, isolated in accordance with the present invention are recombinantly fused or chemically conjugated (including both covalent and non-covalent conjugations) to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. Alternatively, or optionally, antibodies, or fragments thereof, may be used to target heterologous polypeptides to particular cell types, either in vitro or in vivo, by fusing or conjugating the antibodies to antibodies specific for particular cell surface receptors. Alternatively, an antibody can be conjugated to a second antibody to form an antibody heteroconjugate as described by Segal in U.S. Pat. No. 4,676,980.

7.9 Transmembrane Domains

In the present invention, a coding sequence for a transmembrane domain is located downstream of and operatively linked to the first coding region (FIG. 1). Therefore, a fusion protein is expressed that is capable of localizing onto the cell membrane where it can be detected using techniques well known in the art.

Transmembrane regions of proteins are highly hydrophobic or lipophilic domains that are the proper size to span the lipid bilayer of the cellular membrane, thereby anchoring proteins, peptides, or receptors in the cell membrane. They will typically, but not always, comprise 15-30 amino acids. See Chou et al. (1999 Biotechnology and Bioengineering 65(2):160-169), which describes using several transmembrane domains from different source proteins to express a different protein on the cell membrane. One skilled in the art can adapt the method performed in Chou et al. to optimize or screen different transmembrane domains and/or GPI-anchor domains for use in the present invention.

Transmembrane proteins may contain from one or multiple transmembrane domains. For example, receptor tyrosine kinases, certain cytokine receptors, receptor guanylyl cyclases and receptor serine/threonine protein kinases contain a single transmembrane domain. However, various other proteins including channels and adenylyl cyclases contain numerous transmembrane domains.

Many cell surface receptors are classified as "seven transmembrane domain" proteins, as they contain membrane spanning regions. Transmembrane protein receptors include, but are not limited to insulin receptor, insulin-like growth factor receptor, human growth hormone receptor, glucose transporters, transferrin receptor, epidermal growth factor receptor, low density lipoprotein receptor, epidermal growth factor receptor, leptin receptor, interleukin receptors, e.g. IL-1 receptor, IL-2 receptor, etc.

Various approaches in eukaryotic systems achieve surface display by producing fusion proteins that contain the polypeptide of interest and a transmembrane domain from another protein to anchor the fusion protein to the cell membrane. Not wishing to be bound by theory, in eukaryotic cells, the majority of secreted proteins and membrane-bound proteins are translocated across an endoplasmic reticulum membrane concurrently with translation (Wicker and Lodish, Science 230:400 (1985); Verner and Schatz, Science 241:1307 (1988); Hartmann et al., Proc. Nat'l Acad. Sci. USA 86:5786 (1989); Matlack et al., Cell 92:381 (1998)). In the first step of this co-translocational process, an N-terminal hydrophobic segment of the nascent polypeptide, called the "signal sequence," is recognized by a signal recognition particle and targeted to the endoplasmic reticulum membrane by an interaction between the signal recognition particle and a membrane receptor. The signal sequence enters the endoplasmic reticulum membrane and the following nascent polypeptide chain begins to pass through the translocation apparatus in the endoplasmic reticulum membrane. The signal sequence of a secreted protein or a type I membrane protein is cleaved by a signal peptidase on the luminal side of the endoplasmic reticulum membrane and is excised from the translocating chain. The rest of the secreted protein chain is released into the lumen of the endoplasmic reticulum. A type I membrane protein is anchored in the membrane by a second hydrophobic segment, which is usually referred to as a "transmembrane domain." The C-terminus of a type I membrane protein is located in the cytosol of the cell, while the N-terminus is displayed on the cell surface.

As used herein, the term "type II signal anchor domain," or "type II transmembrane domain," refers to a hydrophobic amino acid sequence found in eukaryotic type II integral membrane proteins that, during translation, targets and anchors a polypeptide in the endoplasmic reticulum membrane with a type II orientation. The phrase "type II orientation," refers to a protein topology in which the N-terminus resides in the cytoplasm, while the C-terminus resides within the lumen of the endoplasmic reticulum or on an extracellular cell surface.

In contrast, certain proteins have a signal sequence that is not cleaved, a "signal anchor sequence," which serves as a transmembrane segment. A signal anchor type I protein has a C-terminus that is located in the cytosol, which is similar to type I membrane proteins, whereas a signal anchor type II protein has an N-terminus that is located in the cytosol. Examples of type II signal anchors are described in, for example, Yokoyarna-Kobayashi et al., Gene 228:161 (1999).

In one embodiment, the transmembrane domain is from a type I membrane protein.

Described herein are examples of transmembrane domains, but the transmembrane domain of the fusion proteins of the invention can be any amino acid sequence that will span the plasma cell membrane and can anchor other domains to the membrane. Characteristics of transmembrane domains include generally consecutive hydrophobic amino acids that may be followed by charged amino acids. Therefore, upon analysis of the amino acid sequence of a particular protein, the localization and number of transmembrane domains within the protein may be predicted by those skilled in art. A transmembrane domain may comprise hydrophobic regions or amphipathic regions. Hydrophobic regions contain hydrophobic amino acids, which include, but are not limited to, phenylalanine, methionine, isoleucine, leucine, valine, cysteine, tryptophan, alanine, threonine, glycine and serine and include hydrophobic alpha-helices.

Amphipathic regions may have both hydrophobic and hydrophilic amino acids and moieties and include amphipathic alpha-helices. Hydrophilic amino acids include, but are not limited to, arginine, aspartate, lysine, glutamate, asparagine, glutamine, histidine, tyrosine and proline. Transmembrane domains that form stable alpha helices have been previously described in the art.

Essentially any transmembrane domain is compatible with the present invention. Transmembrane domains include, but are not limited to, those from: a member of the tumor necrosis factor receptor superfamily, CD30, platelet derived growth factor receptor (PDGFR, e.g. amino acids 514-562 of human PDGFR; Chestnut et al. 1996 *J Immunological Methods* 193: 17-27; also see Gronwald et al. 1988 *PNAS* 85:3435); nerve growth factor receptor, Murine B7-1 (Freeman et al. 1991 *J Exp Med* 174:625-631), asialoglycoprotein receptor H1 subunit (ASGPR; Speiss et al. 1985 *J Biol Chem* 260:1979-1982), CD27, CD40, CD120a, CD120b, CD80 (Freeman et al. 1989 *J Immunol* 143:2714-22) lymphotoxin beta receptor, galactosyltransferase (E.G. GenBank accession number AF155582), sialyly transferase (E.G. GenBank accession number NM-003032), aspartyl transferase 1 (Asp1; e.g. GenBank accession number AF200342), aspartyl transferase 2 (Asp2; e.g. GenBank accession number NM-012104), syntaxin 6 (e.g. GenBank accession number NM-005819), ubiquitin, dopamine receptor, insulin B chain, acetylglucosaminyl transferase (e.g. GenBank accession number NM-002406), APP (e.g. GenBank accession number A33292), a G-protein coupled receptor, thrombomodulin (Suzuki et al. 1987 *EMBO J.* 6, 1891) and TRAIL receptor. In one embodiment, the transmembrane domain is from a human protein. For the purposes of the present invention all or part of a transmembrane domain from a proteins may be utilized. In specific embodiments, the transmembrane domain is residues 454-477 of the Asp2, residues 598-661 of APP (e.g., of APP 695), residues 4-27 of galactosyltransferase, residues 470-492 of Asp1, residues 10-33 of sialyltransferase, residues 7-29 of acetylglucosaminyl transferase or residues 261-298 of syntaxin 6. Examples of transmembrane domains are also described in Patent Publications WO 03/104415 and US20040126859. In one embodiment, the transmembrane domain is derived from a human protein, e.g., described herein.

In one embodiment, a cell surface displayed antibody or fragment thereof of the current invention comprises the transmembrane domain of thrombomodulin having an amino acid sequence of LLIGISIASLCLVVALLALLCHLRKKQ (SEQ ID NO:109).

In one embodiment, the pDisplay™ vector from Invitrogen (Carlsbad, Calif.; Catalog no. V660-20) is used during one of the cloning steps for constructing the viral vector. The pDisplay™ vector is a mammalian expression vector designed to target recombinant proteins to the surface of mammalian cells. Proteins of interest are targeted and anchored to the cell surface by cloning the gene of interest in frame with the vector's N-terminal secretion signal and the C-terminal transmembrane anchoring domain of platelet-derived growth factor receptor (PDGFR). For further details see the product manual titled "pDisplay™ Vector for expression of proteins on the surface of mammalian cells" Version C from Invitrogen.

7.10 GPI-Anchor Signal Sequence

A wide range of cell-surface proteins, including enzymes, coat proteins, surface antigens, and adhesion molecules, are attached to plasma membranes via GPI anchors (Burikofer et al. 2002 *FASEB J* 15:545). GPI is a post-translationally added lipid anchor; therefore, unlike conventional polypeptide anchors which have different transmembrane domains and connect to specific cytoplasmic extensions, GPI anchors use a common lipid structure to attach to the membrane, which is irrespective of the proteins linked with it (Englund et al., *Annul Rev. Biochem.* 62:121 (1993)). GPI anchor signal sequences have been identified for many proteins (for example, see Cares et al., *Science* 243:1196 (1989)). The GPI anchor signals have been successfully engineered onto the C-terminus of other un-GPI anchored proteins, and these GPI anchored proteins are coated on the cell surface and are functional. (Anderson et al., P.N.A.S. 93:5894 (1996); Brunschwig et al., *J. Immunother.* 22:390 (1999)). GPI anchors are proposed to function in protein targeting, transmembrane signaling, and in the uptake of small molecules (endocytosis). GPI anchors of plasma membrane proteins are present in eukaryotes from protozoa and fungi to vertebrates. For examples of GPI anchor domains, which may be utilized in the present invention, see Doering, T. L. et al. (1990) *J. Biol. Chem.* 265:61 1-614; McConville, M. J. et al. (1993) *Biochem. J.* 294:305-324; and PCT Publication WO 03/017944).

Without wishing to be limited by theoretical considerations, immediately following protein synthesis, a protein comprising a GPI modification signal is anchored to the ER lumen by a hydrophobic sequence approximately 15-20 amino acids in length. Alberts et al., Molecular Biology Of The Cell, 3rd Edition, p. 591 (1994). A GPI anchor is pre-assembled in the ER and following GPI attachment, the modified protein is glycosylated and shuttled to the exterior surface of the plasma membrane. The process of covalently attaching a GPI anchor to the C-terminus of a peptide is catalyzed by enzymes in the rough ER. Enzymes of the ER cleave the original membrane-anchor sequence and then the new carboxyl-terminus is attached to the amino group of ethanolamine. The anchor typically comprises a phosphoethanolamine (EthN-P), several sugars, including N-acetylglucosamine (GlcNAc) and mannose, linked to an inositol phospholipid (Ikezawa 2002 *Biol Pharm Bull* 25: 409-417). Furthermore, the inositol phospholipid typically contains 1-alkyl, 2-acyl glycerol. The inositol phospholipids in anchors, however, can vary. For example, inositol phospholipids of proteins expressed on erythrocytes have an additional inositol-associated fatty acid that provides an additional point of attachment to the plasma membrane. Such anchors are described as being "two footed." Accordingly, the GPI anchors of to the present invention can be "one footed," "two footed" or "three footed".

There are some general requirements for creating a synthetic GPI anchor sequence. These are a hydrophobic region at the C-terminus of the molecule (10-20 amino acids) not followed by a cluster of basic residues, a "spacer domain" of 7-10 residues preceding the hydrophobic region and small amino acids after the spacer region, where cleavage of the precursor and attachment of the anchor occurs. The GPI anchor is preassembled and added to nascent protein in the endoplasmic reticulum (ER). Concomitant with this step, the initial C-terminal peptide is removed so that the GPI anchor is covalently attached to a new C-terminal amino acid on the protein.

The present invention utilizes a GPI-anchor signal sequence to express an antibody on a cell membrane as described herein. The GPI anchor signal sequence coding region is located downstream of and operatively linked to the first coding region. Therefore, a fusion protein is expressed that is capable of localizing onto the cell membrane where it can be detected using techniques well known in the art (FIG. 1).

It is thought that GPI-anchored proteins also utilize a N-terminal signal sequence that directs the protein to the ER. This signal can be engineered into the coding region by common methods known in the art.

Essentially any GPI-anchor signal sequence can be used in accordance with the invention. GPI-anchor signal sequences are known in the art and/or can be determined using methods known in the art, e.g. using the Big-P predictor analysis available at mendel.imp.univie.ac.at/gpi/gpi_server.html and described in Eisenhaber et al. 1999 *J Mol Biol* 292: 741-758; Eisenhaber et al. 2003 *Nucleic Acids Research* 31: 3631-3634; Eisenhaber et al. Protein Engineering 14: 17-25; Eisenhaber et al. 2000 *TIBS* 25: 340-341; and Eisenhaber et al. 1998 *Protein Engineering* 11: 1155-1161.

In one embodiment, the GPI-anchor signal sequence is selected from a GPI-anchor signal from a eukaryotic, mammalian, primate or human protein. GPI-anchor signal sequences include, but are not limited to, those from decay accelerating factor (DAF; Caras et al. 1987 Science 238: 1280-83); uromodulin, alkaline phosphatase, BP-3, dipeptidylpeptidase, *Trypanosoma brucei* variant surface protein (VSG; Doering et al. *J Bio Chem.* 1990 256:611-614); C8 binding protein (Doering et al. 1990); Alkaline phosphatase; Acetylcholinesterase; 59-Nucleotidase; Alkalinephosphodi-esterase I; Trehalase; *Leishmania* surface protease PSP (gp63); Renal dipeptidase (MDP); Aminopeptidase P; NAD 1 glycohydrolase; Carboxypeptidase M; Carbonic anhydrase IV; Silkworm aminopeptidaseN; ADP-ribosyltransferase; Yeast aspartyl protease; *Chlorella* nitrate reductase; *Plasmodium* transferrin receptor; CD14; CD16; CD48; Folate-binding protein; Urokinase receptor; CNTF receptor; *Trypanosoma* VSG and PARP (procyclin); *Toxoplasma* surface antigens (P22; P30 and P43); *Giardia* GP49; Paramecium surface antigens; Thy-1; CD55 (DAF); Ly6 family (CD59; Ly6A/E); Carcinoembryonic antigen (CEA); Qa-2; CD24, Prions (PrP C; PrP Sc); Squid Sgp-1 and Sgp-2; NCAM-120 (the shortest CD56); CD58 (LFA-3; Seed et al. 1987 Nature 329:840-842); *Dictyostelium* Contact site A; Mouse F3; ChickF11; Chicken axonin-1; Polysphondylium GP64; Grasshopper REGA-1; 5NTD_BOVIN; 5NTD_DISOM; 5NTD_HUMAN; 5NTD_RAT; ACES_TORCA; ACES_TORMA; AMPM_HELVI; AMPM_MANSE; AXO1_HUMAN; BCM1_HUMAN; BCM1_MOUSE; BCM1_RAT; BM86_BOOMI; BST1_HUMAN; BST1_MOUSE; BST1_RAT; CADD_CHICK; CADD_HUMAN; CAH4_HUMAN; CD24_HUMAN; CD24_MOUSE; CD24_RAT; CD48_HUMAN; CD48_MOUSE; CD48_RAT; CD52_HUMAN; CD52_MACFA; CD59_AOTTR; CD59_CALSQ; CD59_CERAE; CD59_HSVSA; CD59_HUMAN; CD59_PAPSP; CD59_PIG; CD59_RAT; CD59_SAISC; CEPU_CHICK; CGM6_HUMAN; CNTR_CHICK; CNTR_HUMAN; CNTR_RAT; CONN_DROME; CSA_DICDI; CWP1_YEAST; CWP2_YEAST; DAF_HUMAN; DAF_PONPY; DAF1_MOUSE; FOL1_HUMAN; FOL1_MOUSE; FOL2_HUMAN; FOL2_MOUSE; G13A_DICDI; G13B_DICDI; GAS1_YEAST; GLYP_HUMAN; GLYP_RAT; GP46_LEIAM; GP63_LEICH; GP63_LEIDO; GP63_LEIGU; GP63_LEIMA; GP85_TRYCR; GPCK_MOUSE; HYA1_CAVPO; HYA1_HUMAN; HYA1_MACFA; HYR1_CANAL; LACH_DROME; LACH_SCHAM; LAMP_HUMAN; LAMP_RAT; LY6A_MOUSE; LY6C_MOUSE; LY6E_MOUSE; LY6F_MOUSE; LY6G_MOUSE; MDP1_HUMAN; MDP1_MOUSE; MDP1_PIG; MDP1_RABIT; MDP1_RAT; MDP1_SHEEP; MKC7_YEAST; MSA1_SARMU; NAR3_HUMAN; NART_MOUSE; NCA_HUMAN; NRT1_RAT; NRT2_RAT; NRTR_CHICK; NRTR_HUMAN; NRTR_MOUSE; NTR1_RAT; OPCM_BOVIN; OPCM_HUMAN; OPCM_RAT; PAG1_TRYBB; PARA_TRYBB; PARB_TRYBB; PARC_TRYBB; PONA_DICDI; PPB1_HUMAN; PPB2_HUMAN; PPB3_HUMAN; PPBE_MOUSE; PPBI_BOVIN; PPBI_HUMAN; PPBI_RAT; PPBJ_RAT; PRIO_ATEGE; PRIO_ATEPA; PRIO_CALJA; PRIO_CEBAP; PRIO_CERAE; PRIO_CERAT; PRIO_CERMO; PRIO_CERNE; PRIO_CERPA; PRIO_CERTO; PRIO_COLGU; PRIO_CRIGR; PRIO_CRIMI; PRIO_GORGO; PRIO_HUMAN; PRIO_MACFA; PRIO_MACSY; PRIO_MANSP; PRIO_MESAU; PRIO_MOUSE; PRIO_PANTR; PRIO_PONPY; PRIO_PREFR; PRIO_RAT; PSA_DICDI; SP63_STRPU; THY1_CHICK; THY1_HUMAN; THY1_MACMU; THY1_MOUSE; THY1_RAT; TIP1_YEAST; TIR1_YEAST; TREA_HUMAN; TREA_RABIT; UPAR_BOVIN; UPAR_HUMAN; UPAR_MOUSE; UPAR_RAT; VCA1_MOUSE; VSA1_TRYBB; VSA8_TRYBB; VSAC_TRYBB; VSE2_TRYBR; VSG2_TRYEQ; VSG4_TRYBR; VSG7_TRYBR; VSI1_TRYBB; VSI2_TRYBB; VSI3_TRYBB; VSI4_TRYBB; VSI5_TRYBB; VSI6_TRYBB; VSIB_TRYBB; VSMO_TRYBB; VSM1_TRYBB; VSM2_TRYBB; VSM4_TRYBB; VSM5_TRYBB; VSM5_TRYBR; VSM6_TRYBB; VSWA_TRYBR; VSWB_TRYBR; VSY1_TRYCO; YAP3_YEAST; YJ9O_YEAST; and YJ9P_YEAST. In one embodiment, the GPI-anchor signal sequence is the C-terminal 37 amino acids of DAF. For further examples of GPI-anchored signal sequences see U.S. Pat. No. 5,968,742 and Doering et al. 1990, supra. Examples of specific GPI-anchored signal include, but are not limited to, those listed in Table 2.

TABLE 2

Examples of Signal Peptides for GPI-anchoring.

| Amino Acid Sequence | SEQ ID NO |
|---|---|
| DKLVKCGGISLLVQNTSWMLLLLLSLSLLQALDFISL | 56 |
| PSPTPTETATPSPTPKPTSTPEETEAPSSATTLISPLSL IVIFISFVLLI | 57 |
| LVPRGSIEGRGTSITAYNSEGESAEFFFLLILLLLLVLV | 58 |
| TSITAYKSEGESAEFFFLLILLLLLVLV | 59 |
| SNKGSGTTSGTARLLSGHTCFTLTGLLGTLVIMGLLT | 60 |
| PNKGSGTTSGTTRLLSGHTCFTLTGLLGTLVTMGLLT | 61 |
| PDHSAATKPSLFLFLVSLLHIFFK | 62 |

7.11 Internal Ribosome Entry Sites

IRESs are used to express two or more proteins from a single vector. An IRES sequence is commonly used to drive expression of a second, third, fourth coding sequence, etc.

IRES elements were first discovered in picornavirus mRNAs (Jackson et al., 1990, *Trends Biochem Sci* 15:477-S3; Jackson et al., 1995, *RNA* 1:985-1000). Examples of IRESs that can be used in accordance with the present invention include, but are not limited to, those from or derived from Picornavirus e.g., HAV (Glass et al. 1993, *Virol* 193:842-852), encephelomycarditis virus (EMCV) which is e.g., commercially available from Novagen (Duke et al., 1992, *J. Virol* 66:1602-9; Jang & Wimmer, 1990, *Gene Dev* 4:1560-1572), and Poliovirus (Borman et al., 1994, *EMBO J.* 13:3149-3157); HCV (Tsukiyama-Kohara et al., 1992, *J Virol* 66:1476-1483) BVDV (Frolov I et al., 1998, *RNA.* 4:1418-1435); *Leishmania* virus, e.g., LRV-1 (Maga et al., 1995, *Mol Cell Biol* 15:4884-4889); Retroviruses e.g., MoMLV (Torrent et al., 1996, *Hum Gene Ther* 7:603-612), VL30 (Harvey murine sarcoma virus), REV (Lopez-Lastra et al., 1997, *Hum Gene Ther* 8:1855-1865); and Eukaryotic mRNA e.g. immunoglobulin heavy-chain binding protein (BiP) (Macejak & Sarnow, 1991, *Nature* 353:90-94), antennapedia mRNA (Oh et al., 1992, *Gene & Dev* 6:1643-1653), fibroblast growth factor 2 (FGF-2) (Vagner et al., 1995, *Mol Cell Biol* 15:35-44), PDGF-B (Bernstein et al., 1997, *J Biol Chem* 272:9356-9362), IGFII (Teerink et al., 1995, *Biochim Biophys Acta* 1264:403-408), translational initiation factor eIF4G (Gan & Rhoads, 1996, *J Biol Chem* 271:623-626), insulin-like growth factor (IGFU), yeast transcription factors TFIID and HAP4, and the vascular endothelial growth factor (VEGF) (Stein et al., 1998, *Mol Cell Biol* 18:3112-3119; Huez et al., 1998, *Mol Cell Biol* 18:6178-6190) as well as those described in U.S. Pat. No. 6,692,736. IRESs have also been reported in different viruses such as cardiovirus, rhinovirus, aphthovirus, HCV, Friend murine leukemia virus (FrMLV) and Moloney murine I leukemia virus (MoMLV). As used herein, the term "IRES" encompasses functional variations of IRES sequences as long as the variation is able to promote direct internal ribosome entry to the initiation codon of a downstream cistron, leading to cap-independent translation. An IRES utilized in the present invention may be mammalian, viral or protozoan.

Thus, the product of a downstream cistron can be expressed from a bicistronic (or multicistronic) mRNA, without requiring either cleavage of a polyprotein or generation of a monocistronic mRNA. Commonly used internal ribosome entry sites are approximately 450 nucleotides in length and are characterized by moderate conservation of primary sequence and strong conservation of secondary structure. The most significant primary sequence feature of the IRES is a pyrimidine-rich site, whose start is located approximately 25 nucleotides upstream of the 3' end of the IRES. See Jackson et al., 1990 (*Trends Biochem Sci*, 15(12):477-83).

Three major classes of picornavirus IRES have been identified and characterized: (1) the cardio- and aphthovirus class (for example, the encephelomycarditis virus, Jang et al., 1990, *Gene Dev* 4:1560-1572); (2) the entero- and rhinovirus class (for example, polioviruses, Borman et al., 1994, *EMBO J.* 13:314903157); and (3) the hepatitis A virus (HAY) class, Glass et al., 1993, *Virol* 193:842-852). For the first two classes, two general principles apply. First, most of the about 450-nucleotide sequence of the IRES functions to maintain particular secondary and tertiary structures conducive to ribosome binding and translational initiation. Second, the ribosome entry site is an AUG triplet located at the 3' end of the IRES, approximately 25 nucleotides downstream of a conserved oligopyrimidine tract. Translation initiation can occur either at the ribosome entry site (cardioviruses) or at the next downstream AUG (entero/rhinovirus class). Initiation occurs at both sites in aphthoviruses.

HCV and pestiviruses such as bovine viral diarrhea virus (BVDV) or; classical swine fever virus (CSFV) have 341 nt and 370 nt long 5'-UTR respectively. These 5'-UTR fragments form similar RNA secondary structures and can have moderately efficient IRES function (Tsukiyama-Kohara et al., 1992, *J. Virol.* 66:1476-1483; Frolov I et al., 1998, *RNA* 4:1418-1435). Recent studies showed that both Friend-murine leukemia virus (MLV) 5'-UTR and rat retrotransposon virus-like 30S (VL30) sequences contain IRES structure of retroviral origin (Torrent et al., 1996, *Hum Gene Ther* 7:603-612).

In eukaryotic cells, translation is normally initiated by the ribosome scanning from the capped mRNA 5' end, under the control of initiation factors. However, several cellular mRNAs have been found to have IRES structure to mediate the cap-independent translation (van der Velde, et al., 1999, *Int J Biochem Cell Biol.* 31:87-106). Non-limiting examples are: immunoglobulin heavy-chain binding protein (BiP) (Macejak et al., 1991, *Nature* 353:90-94), antennapedia mRNA of *Drosophila* (Oh et al., 1992, *Gene & Dev* 6:1643-1653), fibroblast growth factor 2 (FGF-2) (Vagner et al., 1995, *Mol Cell Biol* 15:35-44), platelet-derived growth factor B (PDGF-B) (Bernstein et al., 1997, *J Biol Chem* 272:9356-9362), insulin-like growth factor II (Teerink et al., 1995, *Biochim Biophys Acta* 1264:403-408), the translation initiation factor eIF4G (Gan & Rhoads, 1996, *J Biol Chem* 271: 623-626) and vascular endothelial growth factor (VEGF) (Stein et al., 1998, *Mol Cell Biol* 18:3112-3119; Huez et al., 1998, *Mol Cell Biol* 18:6178-6190).

An IRES may be prepared using standard recombinant and synthetic methods known in the art. For cloning convenience, restriction sites may be engineered into the ends of the IRES fragments to be used.

7.12 Self-Processing Cleavage Sites or Sequences

Although the mechanism is not part of the invention, the activity of self-processing cleavage site, self-processing cleavage sequence or a 2A-like sequence may involve ribosomal skipping between codons which prevents formation of peptide bonds (de Felipe et al., 2000, *Human Gene Therapy* 11: 1921-1931; Donnelly et al., 2001, *J. Gen. Virol.* 82:1013-1025), although it has been considered that the domain acts more like an autolytic enzyme (Ryan et al., 1989, *Virol.* 173.35-45).

A "self-processing cleavage site" or "self-processing cleavage sequence" refers to a DNA or amino acid sequence, wherein upon translation, rapid intramolecular (cis) cleavage of a polypeptide comprising the self-processing cleavage site occurs to result in expression of discrete mature protein or polypeptide products. Also, a "self-processing cleavage site" or "self-processing cleavage sequence" refers to a DNA or amino acid sequence, wherein upon translation, the sequence results in "ribosomal skip" as known in the art and described herein. A "self-processing cleavage site", may also be referred to as a post-translational or co-translational processing cleavage site, exemplified herein by a 2A site, sequence or domain. It has been reported that a 2A site, sequence or domain demonstrates a translational effect by modifying the activity of the ribosome to promote hydrolysis of an ester linkage, thereby releasing the polypeptide from the translational complex in a manner that allows the synthesis of a discrete downstream translation product to proceed (Donnelly et al., 2001, *J Gen Virol.* 82:1013-25). Alternatively, a "self-processing cleavage site", "self-processing cleavage sequence" or a 2A sequence or domain demonstrates "auto-proteolysis" or "cleavage" by cleaving its own C-terminus in cis to produce primary cleavage products (Furler; Palmenberg, 1990, *Ann. Rev. Microbiol.* 44:603-623).

Although the mechanism is not part of the invention, the activity of a 2A-like sequence or self-processing cleavage site may involve ribosomal skipping between codons which prevents formation of peptide bonds (de Felipe et al., 2000, *Human Gene Therapy* 11: 1921-1931; Donnelly et al., 2001, *J. Gen. Virol.* 82:1013-1025), although it has also been considered that the domain acts more like an autolytic enzyme (Ryan et al., Virol. 173.35-45 (1989).

The Foot and Mouth Disease Virus 2A oligopeptide has previously been demonstrated to mediate the translation of two sequential proteins through a ribosomal skip mechanism (Donnelly et al., 2001, *J Gen Virol.* 82:1013-25; Szymczak et al., 2004, *Nat Biotechnol.* 5:589-94; Klump et al., 2001, *Gene Ther.* 10:811-7; De Felipe et al., 2000, *Hum Gene Ther.* 11:1921-31; Halpin et al., 1999, *Plant J.* 17:453-9; Mattion et al., 1996, *J. Virol.* 70:8124-7; and de Felipe P. et al., 1999, *Gene Ther.* 6:198-208). Multiple proteins are encoded as a single open reading frame (ORF). During translation in a bicistronic system, the presence of the FMDV 2A sequence at the 3' end of the upstream gene abrogates the peptide bond formation with the downstream cistron, resulting in a "ribosomal skip" and the attachment of the translated FMDV 2A oligopeptide to the upstream protein (Donnelly et al., 2001, *J Gen Virol.* 82(Pt 5): 1013-25). Processing occurs in a stoichiometric fashion, estimated to be as high as 90-99%, resulting in a near molar equivalency of both protein species (Donnelly et al., 2001, *J Gen Virol.* 82(Pt 5):1027-41). Furthermore, through deletion analysis the amino acid sequence-dependent processing activity has been localized to a small section at the c-terminal end of the FMDV 2A oligopeptide (Ryan et al., 1994, *EMBO J.* 13:928-33). Most members of the Picornavirus family (of which FMDV belongs) use similar mechanisms of cotranslational processing to generate individual proteins (Donnelly et al., 2001, *J Gen Virol.* 82(Pt 5):1027-41). In fact, publications have shown that fragments as small as 13 amino acids can cause the ribosomal skip (Ryan et al., 1994, *EMBO J.* 13:928-33). Incorporation of truncated versions of the peptide in bicistronic vector systems has demonstrated that almost all of the processing activity is preserved even in non-viral vector systems (Donnelly et al., 2001, *J Gen Virol.* 82(Pt 5):1027-41). At least four coding sequences that have been efficiently expressed under a single promoter by strategic placement of these types of elements (Szymczak et al., 2004, *Nat Biotechnol.* 22:589-94.). Therefore, self-processing cleavage sites such as the FMDV 2A oligopeptide may be utilized in the present invention to link expression of the heavy and light chain coding regions.

For the present invention, the DNA sequence encoding a self-processing cleavage site is exemplified by viral sequences derived from a picornavirus, including but not limited to an entero-, rhino-, cardio-, aphtho- or Foot-and-Mouth Disease Virus (FMDV). In one embodiment, the self-processing cleavage site coding sequence is derived from a FMDV.

The FMDV 2A domain is typically reported to be about nineteen amino acids in length (e.g., LLNFDLLKLAGDVESNPGP (SEQ ID NO: 56); TLNFDLLKLAGDVESNPGP (SEQ ID NO: 57), Ryan et al., J. Gen. Virol. 72.2727-2732 (1991)), however oligopeptides of as few as thirteen amino acid residues (e.g., LKLAGDVESNPGP (SEQ ID NO: 58)) have also been shown to mediate cleavage at the 2A C-terminus in a fashion similar to its role in the native FMDV polyprotein processing. Alternatively, a vector according to the invention may encode amino acid residues for other 2A-like regions as discussed in Donnelly et al., 2001, *J. Gen. Virol.* 82:1027-1041 and including but not limited to a 2A-like domain from picornavirus, insect virus, Type C rotavirus, trypanosome repeated sequences or the bacterium, *Thermatoga maritime*.

Variations of the 2A sequence have been studied for their ability to mediate efficient processing of polyproteins (Donnelly et al., 2001). Such variants are specifically contemplated and encompassed by the present invention. In one embodiment, the 2A sequence is a variant 2A sequence.

Further examples and descriptions of self-processing cleavage sites and vectors encoding them are found in US20050042721 and US2005003482.

7.13 Specific Embodiments

Additional embodiments of the present invention are presented in Table 3.

TABLE 3

| Specific embodiments. |
|---|
| 1  A recombinant antibody or fragment thereof that is displayed on the extracellular surface of the cell membrane. |
| 2  The antibody or fragment thereof of embodiment 1, comprising an amino acid sequence that targets the antibody to the cell surface wherein said amino acid sequence is fused to the heavy chain or the light chain of the antibody. |
| 3  The antibody or fragment thereof of embodiment 2, wherein said amino acid sequence is fused to the C-terminal end of the heavy chain or the light chain of the antibody. |
| 4  The antibody or fragment thereof of embodiment 2, wherein said amino acid sequence comprises a transmembrane domain or a GPI anchor signal sequence. |
| 5  The antibody or fragment thereof of embodiment 4, wherein said transmembrane domain is derived from thrombomodulin. |
| 6  The antibody or fragment thereof of embodiment 5, wherein said transmembrane domain comprises SEQ ID NO: 109. |
| 7  The antibody or fragment thereof of embodiment 4, wherein said GPI anchor domain is derived from DAF. |
| 8  The antibody or fragment thereof of embodiment 7, wherein said GPI anchor domain comprises SEQ ID NO: 60 or 61. |
| 9  The antibody or fragment thereof of embodiment 1, wherein said antibody or fragment thereof is from an immunoglobulin type selected from the group consisting of IgA, IgE, IgM, IgD, IgY and IgG. |
| 10  The antibody or fragment thereof of embodiment 1, wherein said antibody or fragment thereof is a murine antibody, a chimeric antibody, a humanized antibody or human antibody. |

TABLE 3-continued

Specific embodiments.

11 The antibody or fragment thereof of embodiment 1, wherein said antibody or fragment thereof is a human antibody.
12 The antibody or fragment thereof of embodiment 1, wherein said antibody or fragment thereof comprises an Fc region.
13 The antibody or fragment thereof of embodiment 1 wherein said antibody or fragment thereof comprises a heavy chain variable region, a light chain variable region or both a heavy chain and a light chain variable region.
14 A polynucleotide encoding the antibody or fragment thereof of any one of embodiments 1-13.
15 A vector comprising the polynucleotide sequence of embodiment 14.
16 The vector of embodiment 15, further comprising a polyadenylation signal sequence.
17 The vector of embodiment 16, wherein said polyadenylation signal sequence is selected from the group consisting of bovine growth hormone polyA signal sequence and SV40 polyA signal sequence.
18 The vector of embodiment 15, further comprising a promoter.
19 The vector of embodiment 18, wherein said promoter is a CMV or RSV promoter.
20 The vector of embodiment 15, further comprising an IRES or self processing cleavage site.
21 The vector of embodiment 15, wherein said vector is capable of replication.
22 The vector of embodiment 21, wherein said vector is a viral vector.
23 The vector of embodiment 22, wherein said viral vector is an adenoviral vector, a baculoviral vector, an adeno associated viral vector, a herpes viral vector or a lentiviral vector.
24 The vector of embodiment 22, wherein said vector is an adenoviral vector.
25 A cell comprising the vector of embodiment 14.
26 The cell of embodiment 25, wherein said cell is a mammalian cell.
27 The cell of embodiment 26, wherein said cell is selected from the group consisting of a NS0 cell, a CHO cell, a Vero cell, an Sf-9 cell, a COS7 cell, and a 293 cell.
28 The cell of embodiment 25, wherein said cell is a human cell.
29 A library of vectors comprising polynucleotides encoding recombinant antibodies or fragments thereof that are displayed on the extracellular surface of the cell membrane.
30 The library of embodiment 29, wherein said antibodies or fragments thereof comprise Fc region variants.
31 The library of embodiment 29, wherein said antibodies or fragments thereof comprise a library of light chain variable region sequences.
32 The library of embodiment 29, wherein said antibodies or fragments thereof comprise a library of heavy chain variable region sequences.
33 The library of embodiment 29, wherein said antibodies or fragments thereof comprise a library of light chain variable region sequences and a library of heavy chain variable region sequences.
34 The library of embodiment 29, 30, 31, 32 or 33, wherein said antibodies or fragments thereof comprise an amino acid sequence that targets the antibody to the cell surface wherein said amino acid sequence is fused to the heavy chain or the light chain of the antibody.
35 The library of embodiment 34, wherein said amino acid sequence is fused to the C-terminal end of the heavy chain or the light chain of the antibody.
36 The library of embodiment 34, wherein said amino acid sequence comprises a transmembrane domain or a GPI anchor signal sequence.
37 The library of embodiment 36, wherein said transmembrane domain is derived from thrombomodulin.
38 The library of embodiment 37, wherein said transmembrane domain comprises SEQ ID NO: 109.
39 The library of embodiment 36, wherein said GPI anchor domain is derived from DAF.
40 The library of embodiment 39, wherein said GPI anchor domain comprises SEQ ID NO: 60 or 61.
41 The library of embodiment 34, wherein said vectors are capable of replication.
42 The library of embodiment 41, wherein said vectors are viral vectors.
43 The library of embodiment 41, wherein said viral vectors are adenoviral vectors, baculoviral vectors, adeno associated viral vectors, herpes viral vectors or lentiviral vectors.
44 The library of embodiment 42, wherein said vectors are adenoviral vectors.
45 A population of cells comprising the library of embodiment 34.
46 The cells of embodiment 45, wherein said cells are mammalian cells.
47 The cells of embodiment 46, wherein said cells are selected from the group consisting of NS0 cells, CHO cells, Vero cells, Sf-9 cells, COS7 cells, and 293 cells.
48 A method of isolating an antibody or fragment thereof having a desirable characteristic comprising: a) culturing the population of cells of embodiment 45 under conditions that allow expression of the antibodies on the cell surface; b) subjecting the population of cells to selection thereby isolating at least one cell expressing an antibody or fragment thereof having the desired characteristic.
49 The method of embodiment 48, further comprising the step of isolating a polynucleotide from the selected cell wherein said polynucleotide encodes the antibody or fragment thereof having a desirable characteristic.
50 The method of embodiment 48, wherein said desirable characteristic is binding to a specific antigen.
51 The method of embodiment 48, wherein said desirable characteristic is increased binding to a specific antigen.
52 The method of embodiment 48, wherein said desirable characteristic is decreased binding to a specific antigen.
53 The method of embodiment 48, wherein said desirable characteristic is binding to an effector molecule.

TABLE 3-continued

Specific embodiments.

54 The method of embodiment 48, wherein said desirable characteristic is reduced binding to an effector molecule.
55 The method of embodiment 48, wherein said desirable characteristic is increased binding to an effector molecule.
56 The method of any one of embodiments 53 to 55, wherein said effector molecule is selected from the group consisting of C1q, FcγRI, FcγRII and FcγRIIIA.
57 The method of embodiment 48, wherein the selection is carried out by incubating the cells with a labeled reagent and sorting the cells based on the binding of the reagent to the cells.
58 A method for producing a library of cells displaying antibodies or antibody fragments on the cell surface comprising: a) infecting a population of cells with a library of vectors comprising polynucleotides encoding recombinant the antibodies or fragments thereof that are displayed on the extracellular surface of the cell membrane; and b) culturing the population of cells under conditions that allow expression of the antibodies on the cell surface.
59 An antibody or fragment thereof comprising an variant Fc region wherein said antibody has a reduced affinity for an effector molecule.
60 The antibody or fragment thereof of embodiment 59, wherein the effector molecule is FcγRIIIA.
61 The antibody or fragment thereof of embodiment 59, wherein the antibody has reduced effector function.
62 The antibody or fragment thereof of embodiment 61, wherein the effector function is ADCC.
63 The antibody or fragment thereof of embodiment 59 or 61, wherein the variant Fc region comprises at least one amino acid substitution, insertion or a combination thereof selected from the group consisting of: W277T; K246R/L251E/T260R; InR234/235; InV235/236; InR236/237; InR237/238; InV238/239; InN238/239; InL238/239; InE238/239; InG238/239; InS239/240; InG240/241; InE240/241; InG240/241/I198T; InL238/239/P238Q; InE238/239/V348A; InS239/240/V266A; InR237/238/G236A.
64 A kit comprising: i) the library of embodiment 34.
65 The kit of embodiment 64, further comprising a cell.
66 The kit of embodiment 65, wherein said cell is a mammalian cell.
67 The kit of embodiment 66, wherein said cell is selected from the group consisting of NS0, CHO, Vero, Sf-9, COS7, 293 or a derivative thereof.

8. EXAMPLES

The invention is now described with reference to the following examples. These examples are provided for the purpose of illustration only and the invention should in no way be construed as being limited to these examples.

8.1 Example 1

Mammalian Cell Surface Display of Antibodies

The following sections describe the generation and characterization of antibody fusion polypeptides that are efficiently displayed on the surface of mammalian cells.

Polynucleotides encoding an immunoglobulin heavy chain fusion polypeptide comprising a transmembrane domain and/or a GPI anchor signal are generated by PCR. Experiments described herein use the heavy chain of anti-EphA2 antibody 12G3H11 as an example unless otherwise noted. Representative examples of GPI anchor signal fusion partners are listed in Table 2. Polynucleotides encoding the various fusion proteins are cloned into pABHL, an antibody expression vector comprising an expression cassette having the following operatively linked sequence elements: 5' end-CMV immediate early promoter-polynucleotide encoding light chain signal peptide-polynucleotide encoding light chain variable region-polynucleotide encoding kappa light chain constant region-ECMV IRES-polynucleotide encoding heavy chain leader peptide (sequence comprises a unique XbaI restriction endonuclease recognition element)-polynucleotide encoding heavy chain variable region-polynucleotide encoding IgG1 heavy chain constant region-unique NotI restriction endonuclease recognition element-Mo-MuLV IRES-polynucleotide encoding Neomycin resistance polypeptide-SV40 polyA-3' end. pABDisplay is a derivative of pABHL that further comprises a DAF variant GPI anchor signal encoding polynucleotide operatively linked to the 3' end of the heavy chain constant region gene; the pABDisplay vector encodes an immunoglobulin heavy chain-DAF vGPI anchor signal fusion polypeptide.

A polynucleotide encoding a heavy chain fusion polypeptide is generated by PCR from a plasmid encoding the heavy chain gene of the 12G3H11 anti-EphA2 antibody. The PCR reaction mix comprises a single forward primer UniXbaI (SEQ ID NO:) and multiple reverse primers. The UniXbaI primer includes a recognition sequence for the XbaI restriction endonuclease to facilitate cloning. The fusion partner specific reverse primer sets were designed to include nucleotide residues encoding the fusion partner (e.g., a transmembrane domain) in frame with the heavy chain, each set comprises multiple partially overlapping reverse primers of approximately 70 nucleotides. The first reverse primer of each set comprises approximately 20 nucleotide residues at its 3' end that anneal to the DNA sequence encoding the heavy chain portion of the junction between heavy chain and fusion partner. The second and subsequent reverse primers comprise ~20 residues at their 3' end that are identical to the 5' most ~20 residues of the preceding reverse primer. The last reverse primer comprises nucleotide residues encoding the C terminus of the fusion partner and a recognition sequence for the NotI restriction endonuclease to facilitate subsequent cloning procedures. The sequence of the three reverse primers used to generate the polynucleotide sequence encoding an anti-Eph2 heavy chain fused to a variant GPI anchor signal of decay accelerated factor (DAF vGPI) are listed in Table 4, as an example for the primer design principles described above.

TABLE 4

Primers For Cell Surface Displayed
Fusion Protein Generation.

| | |
|---|---|
| GPIDAFrev1 | ACGGGTAGTACCTGAAGTGGTTCCACTTCCTTTAT TTGGTTTACCCGGAGACAG GGAGAG (SEQ ID NO: 48) |
| GPIDAF ev2 | CAAACCTGTCAACGTGAAACACGTGTGCCCAGATA GAAGACGGGTAGTACC TGAAGTGGT (SEQ ID NO: 49) |
| GPIDAFrev3 | TGAATTCGCGGCCGCTCAAGTCAGCAAGCCCATGG TTACTAGCGT CCCAAGCAAACCTGTCAACGTGAA ACA (SEQ ID NO: 50) |

A PCR product of the expected size is digested with XbaI and Not I and ligated into a similarly digested pABHL vector to facilitate expression in a mammalian cell. The ligation product is used to transform DH10B competent *E. coli* cells according to the manufacturer's protocols. Colonies of pABHL comprising the correct insert can be identified using various methods known in the art (e.g. restriction digest of DNA preparation, diagnostic PCR amplification of test sequences); their identity can be further confirmed by sequencing using dideoxy sequencing reaction (e.g., Big-Dye® Terminator v3.0 Cycle Sequencing Ready Reaction Kit, ABI). Plasmid DNA is prepared from selected clones using the QIAGEN Mini and Maxi Plasmid Kit according to the manufacturer's protocols.

HEK-293T cells are transiently transfected with a vector encoding an anti-EphA2 antibody fusion polypeptide tested. Transfected cells are cultured for approximately 24-48 hrs to allow antibody expression.

Cell surface display of an anti-EphA2 fusion antibody is detected by staining the transfected cells with a FITC conjugated anti-human IgG antibody and analyzing them on a flow cytometer following standard protocols. Shown in FIG. 2 (left side) are flow cytometry profiles obtained with cells expressing a DAF vGPI, CM GPI or thrombomodulin TM fused anti-EphA2 antibody.

The antigen binding characteristics of a cell surface displayed anti-EphA2 fusion antibody are ascertained by incubating the cells with a biotinylated EphA2-Fc fusion polypeptide. EphA2-Fc fusion protein bound to the cell surface is visualized by further staining the cells with FITC conjugated anti-biotin antibody and analyzing them on a flow cytometer following standard protocols. Shown in FIG. 2 (right side) are flow cytometry profiles obtained with cells expressing a DAF vGPI, CM GPI or thrombomodulin TM fused to the C terminus of the anti-EphA2 antibody heavy chain.

8.2 Example 2

Fc Variant Library Construction

The following Example describes the generation of libraries comprising Fc variants of the anti-EphA2 antibody fused to DAF vGPI. Two different libraries were constructed: an Fc Substitution Library (SL-Fc) and an Fc Insertion Library (IL-Fc).

A231, P232, E233, L242, K246, T250, L251, P257, V259, T260, C261, V273, K274, F275, W277, G281, and V282 with any one of the 19 other naturally occurring amino acids. For example, the substitution library comprises Fc regions having a substitution of the A residue at position 231 with an amino acid residue selected from the group consisting of G, L, M, F, W, K, Q, E, S, P, V, I, C, Y, H, R, N, D, and T. Individual substitutions are identified using standard nomenclature. For example an Fc variant having a substitution of alanine (A) for glycine (G) at residue 231 is identified as A231G.

Fc variants comprising the SL-Fc library are generated by PCR reactions using degenerate primers. Primers for SL-Fc generation are listed in Table 5. Separate sets of PCR reactions are used to generate polynucleotides encoding heavy chains representing all possible substitutions of each amino acid residues targeted in the Fc Substitution Library. For example, polynucleotides encoding the substitution mutants of residue A231 are generated by the following three PCR reactions: 1) 231A residue specific primer and MDAD-20 universal primer are used to amplify the Fc region of DAF vGPI fused anti-EphA2 heavy chain. 2) UniXbaI universal and 231A/232P/233Erev residue specific primers are used to amplify the Fd region of DAF vGPI fused anti-EphA2 heavy chain. 3) PCR fragments from the first two reactions are joined by overlap PCR using universal primers UniXbaI and MDAD-20. PCR fragments of the correct size representing all possible substitution mutations of residue A231 are isolated from reaction 3, digested with XbaI and NotI restriction endonucleases and quantified. The SL-Fc library is generated by mixing an equimolar amount of PCR fragments representing each residue targeted and ligating the mixture into the pABDisplay vector comprising the light chain of 12G3H11 anti-EphA2 antibody.

TABLE 5

Primers Used For Fc
Substitution Library Generation.

| | |
|---|---|
| UniXbaI. | GCT TGA GGT CTA GAC ATA TAT ATG GGT GAC AAT GAC ATC CAC TTT GCC TTT CTC TCC ACA GGT GTC CAC TCC (SEQ ID NO: 10) |
| MDAD-20 | AAC CTC TAC AAA TGT GGT ATG GCT (SEQ ID NO: 11) |
| 231Afor | ACA TGC CCA CCG TGC CCA NNS CCT GAA CTC CTG GGG GGA (SEQ ID NO: 12) |
| 232Pfor | ACA TGC CCA CCG TGC CCA GCA NNS GAA CTC CTG GGG GGA CCG (SEQ ID NO: 13) |
| 233Efor | ACA TGC CCA CCG TGC CCA GCA CCT NNS CTC CTG GGG GGA CCG TCA (SEQ ID NO: 14) |
| 231A/232P/ 233Erev | TGG GCA CGG TGG GCA TGT (SEQ ID NO: 15) |
| 242Lfor | GGG GGA CCG TCA GTC TTC NNS TTC CCC CCA AAA CCC AAG (SEQ ID NO: 16) |
| 246Kfor | GGG GGA CCG TCA GTC TTC CTC TTC CCC CCA NNS CCC AAG GAC ACC CTC ATG (SEQ ID NO: 17) |
| 242l/246Krev | GAA GAC TGA CGG TCC CCC (SEQ ID NO: 18) |
| 250Tfor | CCC CCA AAA CCC AAG GAC NNS CTC ATG ATC TCC CGG ACC (SEQ ID NO: 19) |
| 251Lfor | CCC CCA AAA CCC AAG GAC ACC NNS ATG ATC TCC CGG ACC CCT (SEQ ID NO: 20) |

TABLE 5-continued

Primers Used For Fc Substitution Library Generation.

| | |
|---|---|
| 250T/251Lrev | GTC CTT GGG TTT TGG GGG (SEQ ID NO: 21) |
| 257Pfor | CTC ATG ATC TCC CGG ACC NNS GAG GTC ACA TGC GTG GTG (SEQ ID NO: 22) |
| 259Vfor | CTC ATG ATC TCC CGG ACC CCT GAG NNS ACA TGC GTG GTG GTG GAC (SEQ ID NO: 23) |
| 260Tfor | CTC ATG ATC TCC CGG ACC CCT GAG GTC NNS TGC GTG GTG GTG GAC GTG (SEQ ID NO: 24) |
| 261Cfor | CTC ATG ATC TCC CGG ACC CCT GAG GTC ACA NNS GTG GTG GTG GAC GTG AGC (SEQ ID NO: 25) |
| 257P/259V/260T/261Crev | GGT CCG GGA GAT CAT GAG (SEQ ID NO: 26) |
| 273Vfor | AGC CAC GAA GAC CCT GAG NNS AAG TTC AAC TGG TAC GTG (SEQ ID NO: 27) |
| 274Kfor | AGC CAC GAA GAC CCT GAG GTC NNS TTC AAC TGG TAC GTG GAC (SEQ ID NO: 28) |
| 275Ffor | AGC CAC GAA GAC CCT GAG GTC AAG NNS AAC TGG TAC GTG GAC GGC (SEQ ID NO: 29) |
| 277Wfor | AGC CAC GAA GAC CCT GAG GTC AAG TTC AAC NNS TAC GTG GAC GGC GTG GAG (SEQ ID NO: 30) |
| 273V/274K/275F/277Wrev | CTC AGG GTC TTC GTG GCT (SEQ ID NO: 31) |
| 281Gfor | TTC AAC TGG TAC GTG GAC NNS GTG GAG GTG CAT AAT GCC (SEQ ID NO: 32) |
| 282Vfor | TTC AAC TGG TAC GTG GAC GGC NNS GAG GTG CAT AAT GCC AAG (SEQ ID NO: 33) |
| 284Vfor | TTC AAC TGG TAC GTG GAC GGC GTG GAG NNS CAT AAT GCC AAG ACA AAG (SEQ ID NO:34) |
| 281G/282V/284Vrev | GTC CAC GTA CCA GTT GAA (SEQ ID NO:35) |

The Fc Insertion Library (IL-Fc) comprises variant Fc regions having an insertion of a single amino acid residue between amino acid residues 230 and 231, 231 and 232, 232 and 233, 233 and 234, 234 and 235, 235 and 236, 236 and 237, 237 and 238, 238 and 239, 239 and 240, or 240 and 241 wherein the inserted residue may comprise any one of the twenty naturally occurring amino acids. Individual insertions are identified as "In" followed by the one letter code of the inserted amino acid residue and the position of the residues immediately flanking the insertion. For example InG231/232 denotes a variant Fc comprising an insertion of a glycine between residues 231 and 232.

Fc variants comprising the IL-Fc library are generated by PCR reactions using degenerate primers. Primers for IL-Fc generation are listed in Table 6. Separate sets of PCR reactions are used to generate polynucleotides encoding heavy chains representing all possible amino acid insertions at each of the positions targeted in the Fc Insertion Library. For example, polynucleotides encoding the insertion mutants at position 230/231 are generated by the following three PCR reactions: 1) Position specific primer 230/231Infor and universal primer MDAD-20 are used to amplify the Fc region of DAF vGPI fused anti-EphA2 heavy chain. 2) Universal primers UniXbaI and Inrev are used to amplify the Fd region of DAF vGPI fused anti-EphA2 heavy chain. 3) PCR fragments from the first two reactions are joined by overlap PCR using universal primers UniXbaI and MDAD-20. PCR fragments of the correct size representing all possible insertion mutations of position 230/231 are isolated from reaction 3, digested with XbaI and NotI restriction endonucleases and quantified. The IL-Fc library is generated by mixing an equimolar amount of PCR fragments representing each targeted position and ligating the mixture into the pABDisplay vector comprising the light chain of 12G3H11 anti-EphA2 antibody.

TABLE 6

Primers Used For Fc Insertion Library Generation.

| | |
|---|---|
| 230/231Infor | ACA TGC CCA CCG TGC CCA NNS GCA CCT GAA CTC CTG GGG (SEQ ID NO: 36) |
| 231/232Infor | ACA TGC CCA CCG TGC CCA GCA NNS CCT GAA CTC CTG GGG GGA (SEQ ID NO: 37) |
| 232/233Infor | ACA TGC CCA CCG TGC CCA GCA CCT NNS GAA CTC CTG GGG GGA CCG (SEQ ID NO: 38) |
| 233/234Infor | ACA TGC CCA CCG TGC CCA GCA CCT GAA NNS CTC CTG GGG GGA CCG TCA (SEQ ID NO: 39) |
| 234/235Infor | ACA TGC CCA CCG TGC CCA GCA CCT GAA CTC NNS CTG GGG GGA CCG TCA GTC TTC CTC (SEQ ID NO: 40) |
| 235/236Infor | ACA TGC CCA CCG TGC CCA GCA CCT GAA CTC CTG NNS GGG GGA CCG TCA GTC TTC CTC TTC (SEQ ID NO: 41) |
| 236/237Infor | GCA CCT GAA CTC CTG GGG NNS GGA CCG TCA GTC TTC CTC (SEQ ID NO: 42) |
| 237/238Infor | GCA CCT GAA CTC CTG GGG GGA NNS CCG TCA GTC TTC CTC TTC (SEQ ID NO: 43) |
| 238/239Infor | GCA CCT GAA CTC CTG GGG GGA CCG NNS TCA GTC TTC CTC TTC CCC (SEQ ID NO: 44) |
| 239/240Infor | GCA CCT GAA CTC CTG GGG GGA CCG TCA NNS GTC TTC CTC TTC CCC CCA (SEQ ID NO: 45) |
| 240/241Infor | GCA CCT GAA CTC CTG GGG GGA CCG TCA GTC NNS TTC CTC TTC CCC CCA AAA (SEQ ID NO:46) |
| Inrev | CCC CAG GAG TTC AGG TGC (SEQ ID NO: 47) |

8.3 Example 3

Streptavidin Fused FcγRIIIA Reagent

Primer pair SA1/SA2 (see Table 7.) is used to PCR amplify polynucleotide S encoding streptavidin from template genomic DNA of *Streptomyces avidinii*. Primer pair A1/A2 (see Table 7.) is used to PCR amplify polynucleotide F encoding the extracellular domain of FcγRIIIA from a human bone marrow cDNA library (Clontech) template. Overlapping PCR exploiting the partial sequence complementarity of primers A2 and SA1 is used to generate polynucleotides FA encoding a FcγRIIIA-streptavidin fusion polypeptide. NcoI/NheI digested polynucleotide FA is cloned into the pET-28a (Novagen) expression vector and FcγRIIIA-streptavidin fusion polypeptide is expressed in bacteria following the manufacturer's instructions. Recombinant FcγRIIIA-streptavidin fusion protein is recovered from inclusion bodies and refolded as described by Gao, et al. (1997, *Proc Natl Acad Sci USA*. 94:11777-82). The refolded fusion protein is subsequently purified on an immunobiotin column (PIERCE) according to manufacturer's instructions. The final concentration of the FcγRIIIA-streptavidin preparation is approximately 2.4 mg/ml.

TABLE 7

PCR Primers For Amplifying Streptavidin
And The Extracellular Domains Of FcγRIIIA.

| | |
|---|---|
| A1 primer | AAGCTTCGGTCCG CCACCATGGCAACTGAAGATC TCCCAAAG (SEQ ID NO: 51) |
| A2 primer | GTCTGCCGAACCGCTGCCTGCCAAACCTTGAGTGA TGGT (SEQ ID NO: 52) |
| SA1 primer | GGCAGCGGTTCGGCAGACCCCTCCAAGGAC (SEQ ID NO: 53) |
| SA2 primer | CAGGGGCTAGCTTACTGCTGAACGGCGTCGAGCGG (SEQ ID NO:54) |

8.4 Example 4

Selection of Fc Variants with Altered FcγRIIIA Binding Properties

Figure 3:
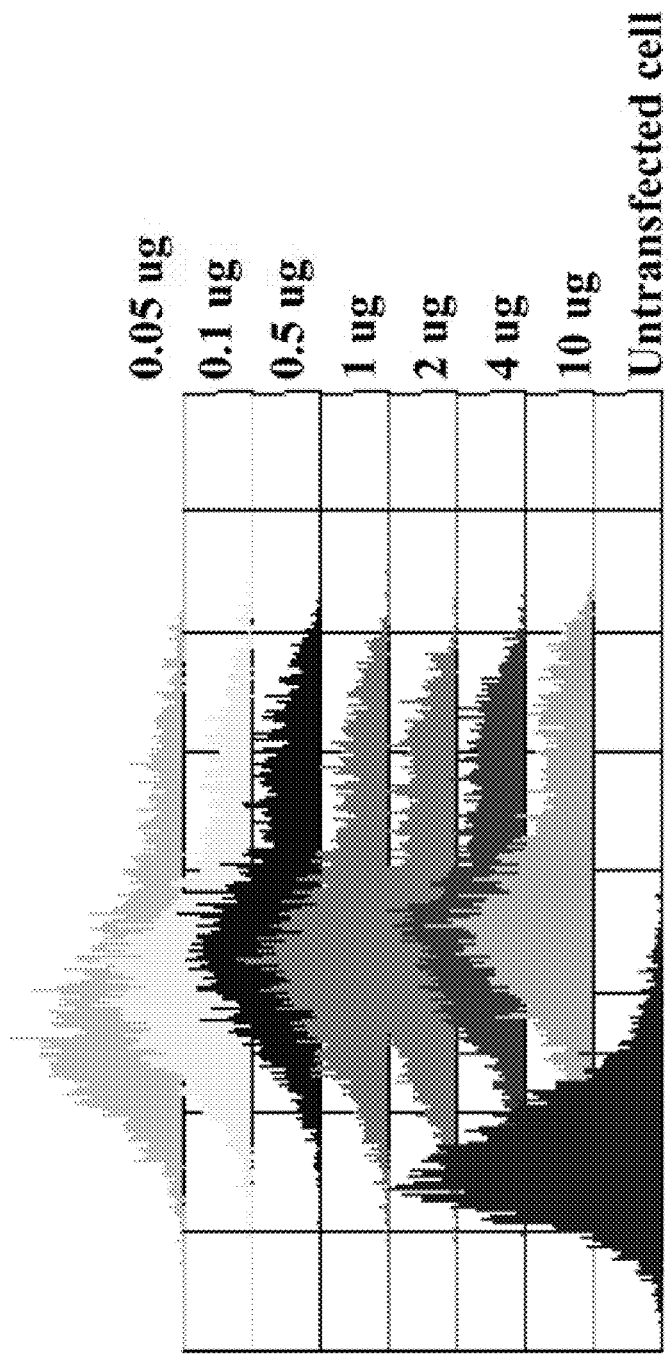

Control experiments are performed to optimize the conditions for transient transfection with Lipofectamine™ 2000 (Invitrogen). HEK-293 cells are transfected with different amounts (e.g., 0.05, 0.1, 0.5, 1.0, 2.0, 4, and 10 μg) of a pABDisplay vector expressing an anti-EphA2 antibody fused to the DAF vGPI signal sequence. The expression level of anti-EphA2 antibody-DAF vGPI fusion polypeptide is ascertained by contacting the transfected cells with FcγRIIIA-streptavidin fusion protein followed by staining with FITC conjugated anti-streptavidin antibody. The cells are subsequently analyzed with a flow cytometer. A reproducible shift in fluorescence intensity is seen for each vector amount tested. The largest shift is observed for plasmid amounts of 4 μg and above. Representative flow cytometry profiles are shown in FIG. 3.

Control experiments are performed to optimize the conditions for a cell surface FcγRIIIA binding assay. HEK-293 cells are transfected with 10 μg of a pABDisplay vector expressing a DAF GPI signal fused anti-EphA2 antibody. Separate aliquots of the transfected cells are contacted with 1:500, 1:1000, 1:2000, 1:3000, 1:4000 or 1:5000 fold diluted FcγRIIIA-streptavidin fusion protein followed by staining with FITC conjugated anti-streptavidin antibody. Cells are subsequently analyzed with a flow cytometer. While each concentration of FcγRIIIA-streptavidin fusion protein used results in a shift of fluorescence intensity, the shifts are less pronounced at dilutions of FcγRIIIA-SA above 1:1000. Representative of flow cytometry profiles are shown in FIG. 4.

Transient transfection of an Fc variant library: HEK-293 cells ($6 \times 10^6$ cells) in 12 ml of growth medium are plated in 100×20 mm tissue culture plates the day before transfection. On the day of transfection, 0.5-10 μg of Fc mutant library plasmid is mixed with 30 μl of Lipofectamine 2000 in OPTI-MEM medium and added into the medium of HEK-293 cells. After 48 hrs incubation post-transfection at 37° C. the transfected cells are detached by using Accutase™ enzyme cell detachment medium (Chemicon) and washed with cold FACS buffer (PBS/10% FBS). Cells are resuspended in 200 μl of FACS buffer containing 1:500 to 1:5000 diluted recombinant FcγRIIIA-streptavidin fusion protein and incubated for 20 min at RT. Cells are washed again with FACS buffer and stained with FITC conjugated anti-streptavidin antibody for 20 min at RT following standard protocols. Cells are washed to remove any unbound anti-streptavidin antibody and resuspended at a density of $2 \times 10^6$/ml.

Isolation of cells expressing Fc variants with altered affinity for FcγRIIIA: Resuspended cells are analyzed on a flow cytometer. A representative example of a fluorescent staining profile is shown in FIG. 5A. Cells with very low or very high fluorescence intensity can be isolated via FACS. An example of the gates suitable for sorting cells with very low staining is shown in FIG. 5A. Isolated cells are re-analyzed on the flow cytometer to check the quality of the sort (FIG. 5B).

Recovery of transiently transfected library DNA: Sorted cells are collected by centrifugation and resuspended in 0.4 ml of cell lysis solution (0.6% SDS and 10 mM EDTA). After 20 min incubation at RT 100 μl of 5 M NaCl is added to the cell lysate. Cell lysate is cleared by centrifugation and the supernatant is extracted with phenol/chloroform/isoamylalcohol (25:24:1). DNA is precipitated with ethanol from the aqueous fraction. DH10B *E. coli* cells are transformed by electroporation with half of the recovered DNA and plated on LB agar plate containing 100 μg/ml carbencilline. After overnight growth, all of the bacterial cells are scraped off the agar plate and used for plasmid DNA extraction.

Additional round(s) of selection: The plasmid DNA recovered may be subjected to additional round(s) (e.g., a total of three rounds) of the above described selection process to further enrich for clones encoding an Fc variant with altered FcγRIIIA binding affinity.

8.5 Example 5

Initial Characterization of Isolated Fc Variants

Fc variants isolated using the selection procedure described in Example 4 are initially characterized as follows. After approximately three rounds of selection, DH10B *E. coli* cells are transformed with DNA recovered from the sorted cell population, individual bacterial clones are selected and plasmid DNA is isolated following standard protocols.

HEK-293 cells are transfected with the isolated plasmid DNA. An aliquot of the transfected cells are stained with FITC conjugated anti-human IgG(H+L) antibody and analyzed on a flow cytometer to ascertain the cell surface expression level of the Fc variant. Examples of staining profiles are shown in FIGS. 6A, B, and C.

The FcγRIIIA binding affinity of the isolated Fc variant is also determined A separate aliquot of transfected cells are incubated with recombinant FcγRIIIA-streptavidin fusion protein followed by staining with FITC conjugated anti-streptavidin antibody as described in Example 3. The staining profile of the cells is determined using a flow cytometer. Examples of staining profiles are shown in FIGS. 6D, E, and F.

Fc variant clones with staining profile indicative of high cell surface expression and low FcγRIIIA affinity are selected for further characterization. An example of such a clone is Fc variant InR236/237 shown in FIGS. 6C and F.

Example 6

Mammalian Expression of Soluble Fc Variants

To express a soluble Fc variant, an oligonucleotide encoding the Fc variant without the DAF vGPI signal sequence is generated by PCR using the UniXbaI and BackNotI (BackNotI: TCAATGAATTCGCGGCCGCTCATTTAC-CCGGAGACAGGGAGAGGC (SEQ ID NO:55)) primers. The PCR product of expected size is digested with XbaI and Not I restriction endonucleases and ligated into an XbaI NotI cleaved pABHL expression vector comprising the light chain of 12G3H11 anti-EphA2 antibody. Bacterial clones having the correct expression construct can be identified using various methods known in the art (e.g. restriction digest of vector DNA preparation, diagnostic PCR amplification of vector sequences). The identity of the clones can be further confirmed by sequencing using the dideoxy method (e.g., Big-Dye® Terminator v3.0 Cycle Sequencing Ready Reaction Kit, ABI). Plasmid DNA is prepared from selected clones using the QIAGEN Mini and Maxi Plasmid Kit according to the manufacturer's protocols HEK-293 cells are transfected with a pABHL vector comprising a polynucleotide encoding a soluble Fc variant using Lipofectamine™ 2000 (Invitrogen) transfection reagent. Transfected cells are incubated for nine days to allow for Fc variant production. Conditioned medium is collected on day 3, 6, and 9 of the incubation period. The Fc variant is purified using a pre-cast protein A column (GE Healthcare). The bound Fc variant is eluted from the column with low pH buffer, neutralized, and dialyzed against PBS. The concentration of the purified Fc variant is calculated from the solution's optical density at 280 nm.

8.6 Example 7

Fc Binding Assays

Fc variants isolated using the methods described above are assayed for their binding affinity to one or more isolated Fc receptors and/or Fc ligand (e.g., FcγRIIIA, C1q) in an ELISA assay format. ELISA assays are performed following standard protocols. Commercially available reagents are used according to the manufacturer's instructions.

Microtiter plates are coated with protein A/G (PIERCE) solution (0.25 µg/ml) and incubated at 4° C. overnight. Any remaining binding sites are blocked with 4% skimmed milk in PBS buffer (blocking buffer) for 1 h at 37° C. Approximately 25-50 µl of control, wild type or Fc variant mutant antibody solution is added to each well and incubated for 1 h at 37° C. After washing the wells, FcγRIIIA-streptavidin fusion protein (1:1000 dilution in 1% BSA) is added for 1 hour at 37° C., followed by washing and incubation with biotin-conjugated HRP for 30 min. Detection is carried out by adding 30 µl of tetramethylbenzidine (TMB) substrate (Pierce) followed by neutralization with 30 µl of 0.2 M $H_2SO_4$. The absorbance is read at 450 nm. IC50 values may be determined and normalized to those obtained for a wild type antibody control assayed at the same time (e.g., in the same microtiter plate). Examples of binding curves for wild type and several Fc variants are shown in FIG. 7.

Microtiter plates coated with protein A/G (PIERCE) solution (0.25 µg/ml) are incubated at 4° C. overnight. Any remaining binding sites are blocked with blocking buffer for 1 h at 37° C. Approximately, 25-50 µl per well of wild type or Fc variant mutant antibody solution is added to each well and incubated for 1 h at 37° C. After washing the wells, approximately 100 µl of 2 µg/ml human C1q (Quidel, CA) is added for 1 h at 37° C. After washing the wells, they are incubated with sheep anti-human C1q antibody (BioDesign) for 1 h at 37° C. After another wash the wells are incubated with a horseradish peroxydase conjugated donkey anti-sheep IgG (Serotec, NC) for 1 h at room temperature. Horseradish peroxydase activity is detected with TMB substrate (KPL, MD). The reaction is quenched with 0.2 M $H_2SO_4$. The absorbance is read at 450 nm. IC50 values are determined and may be normalized to those obtained for a wild type antibody control assayed at the same time (e.g., in the same microtiter plate). Examples of binding curves for wild type and several Fc variants are shown in FIG. 8.

Representative binding curves of several Fc variants to FcγRIIIA-streptavidin and C1q are shown in FIGS. 7 and 8, respectively. The anti-EphA2 wild type antibody and an IgG4 isotype control antibody are used as positive and negative controls, respectively, for each assay performed. Each of the Fc variants assayed has a reduced binding to FcγRIIIA and C1q compared to the wild type antibody. The data for these Fc variants and others are summarized in Table 8.

Example 8

Cell Surface Receptor Binding Assays

Soluble Fc variants isolated using the methods described above are assayed for their binding affinity to the surface of cells expressing one or more Fc receptors (e.g., FcγRIIIA, FcγRII).

Two cell types are utilized, THP-1 cells which predominantly express FcγRII with a small amount of FcγRI present on the cell surface and NK cells which express FcγRIIIA almost exclusively. Early passage THP-1 cells are used and NK cells are isolated from healthy donors by using an NK cell isolation kit from Miltenyi Biotec. For binding of Fc variants to Human NK cell surface (FcγRIIIA), ~10 µl of the Fc variant at different concentrations (e.g., 10 mg/ml to 1 µg/ml) is added to the cells and incubated at 4° C. for 30 min. The cells are washed with FACS buffer, then stained with FITC conjugated goat anti-human IgG(H+L) Fab (Pierce) for 30 min at 4° C. The cells are then washed and analyzed by Guava EasyCyte cytometer. For binding of Fc variants to THP-1 cell surface (FcγRI and FcγRII), ~10 µl of the Fc variant at different concentrations (e.g., 10 µg/ml to 1 µg/ml) is added to the cells, incubated at 4° C. for 30 min. The cells are washed with FACS buffer, then stained with FITC conjugated goat ant-human IgG(H+L) Fab (Pierce) for 30 min at 4° C. The cells are then washed and analyzed by Guava EasyCyte cytometer.

The percentage of THP-1 and NK cells bound by several Fc variants are shown in FIGS. 9 and 10, respectively. The anti-EphA2 wild type antibody and an IgG4 isotype control antibody are used as positive and negative controls, respectively, for each assay performed. Each of the Fc variants assayed has a reduced binding to the cell surface receptors present on THP-1 and NK cells compared to the wild type antibody. The data for these Fc variants and others are summarized in Table 8.

Example 9

Antigen Binding

Antigen binding may be determined using methods well known in the art. For example an ELISA based assay following standard protocols may be used. Briefly, Microtiter plates are coated with protein A/G (PIERCE) solution (0.25 µg/ml) and incubated at 4° C. overnight. The plates are then washed with PBS/0.1% Tween-20 and any remaining binding sites are blocked with blocking buffer. 50 µl of test antibody at concentrations from ~5000 ng/ml to ~5 ng/ml, are added to each well and incubated for ~60 min at 37° C. ~50 µl of an appropriate dilution of biotin conjugated EphA2 protein (e.g., EphA2-Fc fusion described in Dall'Acqua, F. M. et al., *J Immunol*, 177: 1129-1138 (2006)) is added to each well and incubated for ~60 min at 37° C., followed by washing. Horseradish peroxidase conjugated streptavidin is added to each well and incubated for 30 min at 37° C. following the manufacturer's instructions. Detection is carried out by adding 30 µl of tetramethylbenzidine (TMB) substrate (Pierce) followed by neutralization with 30 µl of 0.2 M $H_2SO_4$. The absorbance is read at 450 nm.

The ligand binding activity of several Fc variants that showed reduced Fc receptor binding and/or ADCC activity was examined by ELISA. The wild type anti-EphA2 antibody and two antibodies of irrelevant specificity (Vitaxin and anti-HMBG1) were used as positive and negative controls, respectively, for each assay. The antibodies were tested by ELISA assay using a biotinylated human EphA2 protein. All of the Fc variants examined showed binding affinity for human EphA2 similar to that of the wild type antibody; the IC50 values are indicated (FIG. 11).

Example 10

Antibody Dependent Cell Mediated Cytotoxicity (ADCC) Assay

Antibody dependent cell cytotoxicity (ADCC) is assayed in a four-hour non-radioactive lactate dehydrogenase (LDH) release assay (Promega Corporation, Madison, Wis.). Briefly, EphA2 expressing A549 target cells are distributed into 96-well U-bottomed plates ($1\times10^4$/50 µl) and pre-incubated with serial dilution of antibodies (50 µl) for 20 min at 37° C. Human effector cells (100 µl) are then added at effector to target cell ratios of 50:1 and 25:1. Peripheral blood mononuclear cells (PBMC) purified from healthy human donors using Lymphocyte Separation Medium (MP Biomedicals, Irvine, Calif.), resuspended in the medium (RPMI-1640 10% FBS—2 mM L-Glu-Pen/Strep, 5 ng/ml of IL-2), and incubated at 37° C. for overnight were used as effector cells. After 4 hrs of incubation at 37° C., plates are centrifuged, and cell death is analyzed by measuring the release of LDH into the cell supernatant with a 30-minute coupled enzymatic assay. The percentage of specific lysis is calculated according to the formula: % specific lysis=100×(EX−ESpon−TSpon)/(Tmax−Tspon), where EX represents the release from experimental wells, Espon is the spontaneous release of effector cells alone, Tspon is spontaneous release of target cells alone, and $T_{max}$ is the maximum release from lysed target cells.

Shown in FIG. 12 are cytotoxicity curves from representative ADCC assays performed using several of the isolated Fc variants. A positive control wild type anti-EphA2 antibody and a negative control anti-CD4 antibody (R347) are also included in the assay. A549 cells expressing EphA2, but not CD4, are used as targets. Effector cells are purified from healthy human donors. The assays are performed using two different ratios of target to effector cell (50:1 and 25:1) and antibody concentrations ranging from 0.1 to 10000 ng per well. Each of the Fc variants and the negative control have little to no activity above background while the wild type antibody mediates efficient lysis of the target cells at both target to effector ratios. The results for a number of Fc variants are summarized in Table 8.

TABLE 8

Binding Affinity and ADCC Activity of Fc Variants

| Fc mutants | FcγRIIIA Binding | C1q binding | FcγRI&II Binding | ADCC activity |
|---|---|---|---|---|
| Wild type | 0.15 ug/ml | | | |
| W277T | 0.5 ug/ml | ND | ND | ND |
| K246R/L251E/T260R | >20 ug/ml | 2 fold les | 9 fold less | not induce |
| InR236/237 | >20 ug/ml | 2 fold les | 20 fold less | not induce |
| InN238/239 | >20 ug/ml | 5 fold less | 20 fold less | not induce |
| InE240/241 | 4.927 ug/ml | ND | ND | |
| InV238/239 | >20 ug/ml | 2 fold less | 5 fold less | not induce |
| InG240/241 + I198T | >20 ug/ml | 4 fold less | 20 fold less | not induce |
| InR234/235 | >20 ug/ml | 3 fold less | 20 fold less | not induce |
| InL238/239 + P238Q | >20 ug/ml | 4 fold less | 9 fold less | not induce |
| InE238/239 + V348A | >20 ug/ml | 6 fold less | 6 fold less | not induce |
| InS239/240 + V266A | >20 ug/ml | 3 fold less | 27 fold less | not induce |
| InR237/238 + G236A | >20 ug/ml | 5 fold less | 27 fold less | not induce |

Example 11 cDNA Library Synthesis

First, total RNA is isolated from the peripheral blood mononuclear cells (PBMC) of twelve healthy donors e.g., by using QIAgen RNeasy kit. In addition, a pool of mRNA is obtained by combining material from several sources (Bioscience, Cat#636170, BD Bioscience Cat. 6594-1, Origene technologies and Biochain Institute, Inc. Cat#M1234246). A human cDNA library is synthesized by using Superscript III RT kit (Invitrogen) following the manufacturer's instructions.

Example 12 pENABdisplay Vector Construction

The pENTR™2B (Invitrogen) is digested with XbaI and SfoI to delete the ccdB gene. The larger fragment from the SpeI and BSTZ17I digested 12G3H11 pABdisplay vector comprising the antibody expression cassette was cloned into the XbaI SfoI digested pENTR™2B vector. The resulting vector, designated as pENPABdisplay, comprises a 12G3H11 anti-EphA2-DAF vGPI fusion antibody expression cassette flanked by the attL1 and attL2 recombination signals.

Example 13 pENABdisplay Heavy Chain Library Construction

Rearranged VH segments are PCR amplified from a human cDNA library (see Example 11). Primers used are listed in Table 9. PCR reactions to amplify polynucleotides encoding a signal sequence are performed in a volume of 100 μl containing 40 ng of pENABdisplay, 10 μmol of the Hcldf-forward and 84830-D10-reverse primers, and Pfu ultra Taq polymerase (Stratagene, Cat. 600380) following the manufacturer's suggestion. The PCR reaction is initially heated to 95° C. for 5 minutes, followed by 25 cycles of 95° C. for 30 sec, 55° C. for 30 sec, 68° C. for 45 sec and held at 68° C. for 7 minutes. The PCR product is purified for example by using the QIAgen PCR purification Kit (Cat. 28106). The heavy chain variable regions are amplified separately from the cDNA library using Taq DNA polymerase (Invitrogen, cat. 18038-018), 50 μmol of Medieu-VH1-15 and 50 μmol of the pooled reverse-Medieu-JH1, JH2 and JH3 primers following the manufacturer's instructions. After 5 minutes of denaturing, the template is amplified for 8 cycles at 95° C. for 30 sec, 52° C. for 60 sec and 72° C. for 60 sec; the template is further amplified for 32 cycles at 95° C. for 30 sec, 62° C. for 30 sec, 72° C. for 60 sec and held at 72° C. for 7 minutes. The VH fragments are agarose gel purified and an overlapping PCR is performed with the VH fragments and the signal sequence using the forward-HcldF and pooled reverse-medieu-JHL JH2 and JH3 primers; the PCR reaction is performed with Taq DNA polymerase, 20 ng of each template and 50 μmol of the primers. After 5 minutes of denaturing, the template is amplified for 8 cycles without the primers at 95° C. for 30 sec, 55° C. for 45 sec and 68° C. for 60 sec; the template is further amplified for 25 cycles with primers at 95° C. for 30 sec, 55° C. for 30 sec, 68° C. for 60 sec and held at 72° C. for 7 minutes. The PCR product is gel purified as described previously. An equal amount of each product is mixed and digested with XbaI and SalI restriction endonucleases (New England Biolabs) and cloned into the pENPAB-display vector to create the heavy chain (IgG1) library. The library degree of diversity is determined by sequencing 96 clones.

TABLE 9

Primers used for human naïve antibody library generation.

Human V heavy specific forward primers

| Medieu-VH1 | GCCTTTCTCTCCACAGGTGTACACTCCCAGGTKC AGCTGGTGCAGTCTGG (SEQ ID NO: 63) |
|---|---|
| Medieu-VH2 | GCCTTTCTCTCCACAGGTGTACACTCCCAGGTCC AGCTTGTGCAGTCTGG (SEQ ID NO: 64) |
| Medieu-VH3 | GCCTTTCTCTCCACAGGTGTACACTCCSAGGTCC AGCTGGTACAGTCTGG (SEQ ID NO: 65) |
| Medieu-VH4 | GCCTTTCTCTCCACAGGTGTACACTCCCARATGC AGCTGGTGCAGTCTGG (SEQ ID NO: 66) |
| Medieu-VH5 | GCCTTTCTCTCCACAGGTGTACACTCCCAGATCA CCTTGAAGGAGTCTGG (SEQ ID NO: 67) |

TABLE 9-continued

Primers used for human naïve antibody library generation.

| Medieu-VH6 | GCCTTTCTCTCCACAGGTGTACACTCCCAGGTCA CCTTGAAGGAGTCTGG (SEQ ID NO: 68) |
|---|---|
| Medieu-VH7 | GCCTTTCTCTCCACAGGTGTACACTCCGARGTGC AGCTGGTGGAGTCT (SEQ ID NO: 69) |
| Medieu-VH8 | GCCTTTCTCTCCACAGGTGTACACTCCCAGGTGC AGCTGGTGGAGTCTGG (SEQ ID NO: 70) |
| Medieu-VH9 | GCCTTTCTCTCCACAGGTGTACACTCCGAGGTGC AGCTGTTGGAGTCTGG (SEQ ID NO: 71) |
| Medieu-VH10 | GCCTTTCTCTCCACAGGTGTACACTCCGAGGTGC AGCTGGTGCAGWCYGG (SEQ ID NO: 72) |
| Medieu-VH11 | GCCTTTCTCTCCACAGGTGTACACTCCCAGSTGC AGCTGCAGGAGTCSGG (SEQ ID NO: 73) |
| Medieu-VH12 | GCCTTTCTCTCCACAGGTGTACACTCCCAGGTGC AGCTACAGCAGTGGGG (SEQ ID NO: 74) |
| Medieu-VH13 | GCCTTTCTCTCCACAGGTGTACACTCCGARGTGC AGCTGGTGCAGTCTGG (SEQ ID NO: 75) |
| Medieu-VH14 | GCCTTTCTCTCCACAGGTGTACACTCCCAGGTAC AGCTGCAGCAGTCAGG (SEQ ID NO: 76) |
| Medieu-VH15 | GCCTTTCTCTCCACAGGTGTACACTCCCAGGTGC AGCTGGTGCAATCTGG (SEQ ID NO: 77) |

Human V heavy specific reverse primers

| Medieu-JH1 | GAAGACGGATGGGCCCTTGGTCGACGCTGAGGAG ACRGTGACCAGGGT (SEQ ID NO: 78) |
|---|---|
| Medieu-JH2 | GAAGACGGATGGGCCCTTGGTCGACGCTGAAGAG ACGGTGACCATTGT (SEQ ID NO: 79) |
| Medieu-JH3 | GAAGACGGATGGGCCCTTGGTCGACGCTGAGGAG ACGGTGACCGTGGT (SEQ ID NO: 80) |

Human V kappa specific forward primers

| Medieu-VK1 | CTCTGGCTCCCCGGGGCGCGCTGTRACATCCAGA TGACCCAGTCTCC (SEQ ID NO: 81) |
|---|---|
| Medieu-VK2 | CTCTGGCTCCCCGGGGCGCGCTGTGMCATCCRGW TGACCCAGTCTCC (SEQ ID NO: 82) |
| Medieu-VK3 | CTCTGGCTCCCCGGGGCGCGCTGTGTCATCTGGA TGACCCAGTCTCC (SEQ ID NO: 83) |
| Medieu-VK4 | CTCTGGCTCCCCGGGGCGCGCTGTGATATTGTGA TGACCCAGACTCC (SEQ ID NO: 84) |
| Medieu-VK5 | CTCTGGCTCCCCGGGGCGCGCTGTGATRTTGTGA TGACWCAGTCTCC (SEQ ID NO: 85) |

TABLE 9-continued

Primers used for human naïve antibody library generation.

| | |
|---|---|
| Medieu-VK6 | CTCTGGCTCCCCGGGGCGCGCTGTGAAATTGTGT<br>TGACRCAGTCTCC<br>(SEQ ID NO: 86) |
| Medieu-VK7 | CTCTGGCTCCCCGGGGCGCGCTGTGAAATAGTGA<br>TGACGCAGTCTCC<br>(SEQ ID NO: 87) |
| Medieu-VK8 | CTCTGGCTCCCCGGGGCGCGCTGTGAAATTGTAA<br>TGACACAGTCTCC<br>(SEQ ID NO: 88) |
| Medieu-VK9 | CTCTGGCTCCCCGGGGCGCGCTGTGACATCGTGA<br>TGACCCAGTCTCC<br>(SEQ ID NO: 89) |
| Medieu-VK10 | CTCTGGCTCCCCGGGGCGCGCTGTGAAACGACAC<br>TCACGCAGTCTCC<br>(SEQ ID NO: 90) |
| Medieu-VK11 | CTCTGGCTCCCCGGGGCGCGCTGTGAAATTGTGC<br>TGACTCAGTCTCC<br>(SEQ ID NO: 91) |

Human V kappa specific reverse primers

| | |
|---|---|
| Ckappa | GCATGCTCGACATCGATTCACTAACACTCTCCCC<br>TGTTGAAGCTC<br>(SEQ ID NO: 92) |

Human V lambda specific forward primers

| | |
|---|---|
| Medieu-Vλ1 | CTCTGGCTCCCCGGGGCGCGCTGTCAGTCTGTGC<br>TGACTCAGCCACC<br>(SEQ ID NO: 93) |
| Medieu-Vλ2 | CTCTGGCTCCCCGGGGCGCGCTGTCAGTCTGTGY<br>TGACGCAGCCGCC<br>(SEQ ID NO: 94) |
| Medieu-Vλ3 | CTCTGGCTCCCCGGGGCGCGCTGTCAGTCTGCCC<br>TGACTCAGCCT<br>(SEQ ID NO: 95) |
| Medieu-Vλ4 | CTCTGGCTCCCCGGGGCGCGCTGTTCCTATGWGC<br>TGACWCAGCCA<br>(SEQ ID NO: 96) |
| Medieu-Vλ5 | CTCTGGCTCCCCGGGGCGCGCTGTTCCTATGAGC<br>TGACACAGCTACC<br>(SEQ ID NO: 97) |
| Medieu-Vλ6 | CTCTGGCTCCCCGGGGCGCGCTGTTCTTCTGAGC<br>TGACTCAGGACC<br>(SEQ ID NO: 98) |
| Medieu-Vλ7 | CTCTGGCTCCCCGGGGCGCGCTGTTCCTATGAGC<br>TGATGCAGCCAC<br>(SEQ ID NO: 99) |
| Medieu-Vλ8 | CTCTGGCTCCCCGGGGCGCGCTGTCAGCYTGTGC<br>TGACTCAATC<br>(SEQ ID NO: 100) |
| Medieu-Vλ9 | CTCTGGCTCCCCGGGGCGCGCTGTCWGSCTGTGC<br>TGACTCAGCC<br>(SEQ ID NO:101) |
| Medieu-Vλ10 | CTCTGGCTCCCCGGGGCGCGCTGTAATTTTATGC<br>TGACTCAGCCCCA<br>(SEQ ID NO: 102) |
| Medieu-Vλ11 | CTCTGGCTCCCCGGGGCGCGCTGTCAGRCTGTGG<br>TGACYCAGGAGCC<br>(SEQ ID NO: 103) |
| Medieu-Vλ12 | CTCTGGCTCCCCGGGGCGCGCTGTCAGGCAGGGC<br>TGACTCAGCCACC<br>(SEQ ID NO: 104) |

TABLE 9-continued

Primers used for human naïve antibody library generation.

Human Vlambda specific reverse primers

| | |
|---|---|
| Clambda1 | GCATGCTCGACATCGATTCACTATGAACATTCTG<br>TAGGGGCCACTG<br>(SEQ ID NO: 105) |
| Clambda2 | CAGCATGCTCGACATCGATTCACTAAGAGCATTC<br>TGGGGGCCACTG<br>(SEQ ID NO: 106) |

V heavy signal sequence specific primers

| | |
|---|---|
| Hc1dF | CCATGGGATGGAGCTGTATCA<br>(SEQ ID NO:107) |
| 84830-D10 | GGAGTGTACACCTGTGGAGAGAAAGGC<br>(SEQ ID NO:108) |

Example 14 pENABdisplay Light Chain Library Construction

Rearranged antibody kappa and lambda light chain segments are PCR amplified from a human cDNA library (see Example 11). Primers used are listed in Table 9. Twelve VHλ forward primers are paired with two λ reverse primers to amplify the antibody λ light chain variable and constant regions. Similarly, eleven VHK forward primers are paired with the K reverse primer to amplify the antibody K light chain variable and constant regions. Using Pfu Ultra (Stratagene) and following the manufacture's instructions, each reaction is done separately using 10 µmol of each primer. After the initial 3 minutes denaturation, the PCR reaction is amplified for 30 cycles at 95° C. for 30 sec, 52° C. for 30 sec, 68° C. for 90 sec and held at 68° C. for 10 minutes. The PCR products are pooled, agarose gel purified and digested with BssHII and ClaI restriction endonucleases. Using similarly digested pENABdisplay vector, the products are T4 DNA ligated, phenol-chloroform extracted, precipitated and transformed into DH10B electrocompetent cells. The library's degree of diversity is determined by sequencing 96 clones.

Example 15 pENABdisplay Heavy Chain-Light Chain Library Construction

To combine the diverse antibody heavy chains and light chains of the heavy chain and light chain libraries, respectively, into a single heavy chain-light chain library, the pENPABdisplay light chain library is digested with Xba I and Not I restriction endonucleases. The pENPABdisplay heavy chain library is similarly digested to release the diverse heavy chain encoding fragments, which are then agarose gel purified and ligated into the XbaI NotI digested pENABdisplay light chain library.

Example 16

Adenoviral Expression Vector Construction

Using the Gateway® system, the antibody expression cassette of the pENABdisplay VH-VL library is recombined into the pAd/PL-DEST (Invitrogen, cat. V494-20) vector via the LR reaction following the manufacturer's instructions. The reaction is phenol-chloroform extracted, precipitated and transformed into the DH10B electrocompetent cells. Following plasmid DNA isolation of the resulting pAd/PL-VH-VL expression vector, a digestion is performed with Pac Ito expose left and right viral ITRs and remove bacterial sequences. The ITR fragment is phenol-chloroform extracted, precipitated and transfected into HEK-293A cells using Lipofectamine 2000 (Invitrogen). The virus is harvested after the cytopathic effect is observed. Viral titers are determined by BD AdenoX Rapid titer kit (Becton Dickinson, CA).

pAd/PL-DEST is based on a replication incompetent adenovirus that can only be propagated in cell lines that provide the E1 protein in trans (e.g., 293A cells). The pAd/PL-DEST based library described above is well suited for screens using a cell line that conditionally expresses E1 protein, and thus conditionally supports viral replication. Such a line can be generated via stable transfection of suitable cells with an E1 protein expression construct comprising an inducible mammalian promoter (e.g., tetracycline inducible promoters from Clonetech). The screening process itself may be performed as describe in the example below. E1 protein expression should be kept off during 1) infection with the library, 2) incubation of infected cells to allow cell surface display of library encoded antibody 3) selection of the cells expressing an antibody with the desired characteristics. E1 protein expression should be induced in the selected cells comprising an adenovirus encoding an antibody with desired characteristics to promote viral replication and thus to aid recovery of the virus.

Alternatively, the pENABdisplay heavy chain-light chain library may be recombined into a modified pAd/PL-DEST vector comprising the ts369 mutation (Hasson, T. B. et al., *J Virol* 63(9):3612-21 (1989)). Methods for generating a pAd/PL-DEST vector comprising the ts369 mutation are described bellow. Screen of library may be performed using a protocol described in Example 17.

8.7 Example 17

Proof of Principle

Screen of an Artificial Adenoviral Library pAd/PL-DEST vector comprising the ts369 mutation (Hasson, T. B. et al., *J Virol* 63(9):3612-21 (1989)) is generated by replacing an RsrII fragment (position 9666 to 17373) of the pAd/PL-DEST vector comprising the wild type sequence with a fragment comprising the ts369 mutation. Briefly, the RsrII fragment (position 9666 to 17373) of pAd/PL-DEST is cloned into a pUC18 vector with a modified multiple cloning site having two RsrII sites. Basepair substitutions corresponding to ts369 are introduced into the wild type fragment with the QuickChange kit (Stratagene) using oligonucleotides TS369F and TS369R (SEQ ID NO: 110 and 111, respectively) according the manufacturer's instruction. The RsrII fragment comprising ts369 is inserted into RsrII cut pAd/PL-DEST to generate pAd/PL-DEST/ts369. All of the cloning steps are performed using standard laboratory protocols.

pENPABdisplay expression constructs comprising the 10C2 anti-EphA2 antibody, the 3F2 anti-EphA2 antibody, the Abegrin anti-αvβ3 integrin antibody, an anti-PCDGF antibody, a 3F2 anti-EphA2 ScFvFc (single chain Fv-Fc fusion), and a Abegrin anti-αvβ3 integrin ScFvFc are generated using standard cloning procedures. These expression constructs are delivered into the pAd/PL-DEST/ts369 vector using the LR reaction of the Gateway® (Invitrogen) system following the manufacturer's recommendations. The LR reaction is phenol-chloroform extracted, precipitated and transformed into the DH10B electrocompetent cells. Following plasmid DNA isolation of the resulting pAd/PL/ts369 expression vector, a digestion is performed with Pac I to expose left and right viral ITRs and remove bacterial sequences. The ITR fragment is phenol-chloroform extracted, precipitated and transfected into HEK-293A cells using Lipofectamine 2000 (Invitrogen). The virus is harvested after the cytopathic effect is observed. Viral titers expressed as Viral Particle/ml (VP/ml) are determined using Quick Titer™ Adenovirus Quantitation Kit (Cell Biolabs, Inc). Multiplicity of infection (MOI) is calculated based on VP/ml titer.

Artificial libraries were prepared by mixing aliquots of a) Abegrin anti-αvβ3 integrin antibody and 3F2 anti-EphA2 ScFvFc expressing viruses, b) an anti-PCDGF antibody and 10C2 anti-EphA2 antibody expressing viruses, and c) 3F2 anti-EphA2 antibody and Abegrin anti-αvβ3 integrin ScFvFc expressing viruses to reach a final ratio of 100:1 viral particles.

A polynucleotide encoding a human EphA2-Fc fusion protein consisting of the extracellular domain of human EphA2 fused with the Fc portion of a human IgG1 (SEQ ID NO: 112), can be generated via overlap PCR following standard protocols. Commercially available human cDNA may be used as template for the PCR reactions (e.g., FirstChoice® PCR-Ready and RACE-Ready cDNA from Ambion). Human EphA2-Fc fusion protein can be expressed in human embryonic kidney (HEK) 293 cells and purified by protein A affinity chromatography using standard protocols. Human EphA2-Fc biotinylation may be carried out using an EZ-Link Sulfo-NHS-LC-Biotinylation Kit according to the manufacturer's instructions (Pierce, Rockford, Ill.).

Human αvβ3 integrin (Chemicon, #CC1018) is biotinylated utilizing an EZ-Link Sulfo-NHS-LC-Biotinylation Kit according to the manufacturer's instructions (Pierce, Rockford, Ill.).

Control experiments are performed to optimize the conditions for the detection of cell surface displayed antibodies with αVβ3-biotin. 293A cells are infected at MOI=2.5 with adenoviruses encoding either the Abegrin anti-αvβ3 integrin ScFvFc or 3F2 anti-EphA2 ScFvFc. Infected cells are incubated for 24 hrs at 40° C. Cells are harvested, resuspended at $4 \times 10^6$ cells/ml, and incubated in 4% milk at room temperature (RT) for 20 minutes. Separate aliquots of the infected cells are contacted with 10 µg/ml, 5 µg/ml, 2.5 µg/ml, 1 µg/ml or 0.5 µg/ml αVβ3-biotin in 4% milk at RT for 30 minutes and on ice for an additional 10 minutes. Cells are washed to remove any unbound sαVβ3-biotin and stained with FITC conjugated anti-human IgG-Fc (Pierce) or APC-conjugated streptavidin (Pierce) following manufacturers recommendations. Uninfected 293A cells are processed the same way and used as negative control. Fluorescently stained cells are analyzed on a flow cytometer. Data obtained are summarized in Table 10.

TABLE 10

Titration of αVβ3-biotin staining of Abegrin anti-αvβ3 integrin ScFvFc (α-αVβ3) or 3F2 anti-EphA2 ScFvFc (α-EphA2) displaying cells.
Percentage of positively stained cell

| sαVβ3-biotin conc. used | | 10 ug/ml | | 5 ug/ml | | 2.5 ug/ml | | 1 ug/ml | | 0.5 ug/ml | |
|---|---|---|---|---|---|---|---|---|---|---|---|
| secondary stain | | Fc[a] | Str[b] | Fc[a] | Str[b] | Fc[a] | Str[b] | Fc[a] | Str[b] | Fc[a] | Str[b] |
| surface Ab expressed | α-αVβ3 | 91 | 90 | 84 | 84 | 85 | 85 | 85 | 83 | 86 | 81 |
| | α-EphA2 | 88 | 3 | 85 | 1 | 83 | 1 | 82 | 0 | 82 | 0 |
| | none | 2 | 0 | 3 | 0 | 1 | 0 | 0 | 0 | 0 | 0 |

[a]Fc secondary stain denotes FITC conjugated anti-human IgG-Fc
[b]Str secondary stain denotes APC-conjugated streptavidin Proof of principle selection experiment I: 293A cells (15× $10^6$ cells) in 30 ml of growth medium are plated in T-175 tissue culture flask the day before infection and incubated at 37° C. overnight. Cells are infected with the artificial library containing a mix of 3F2 anti-EphA2 antibody and Abegrin anti-αvβ3 integrin ScFvFc expressing viruses at a ratio of 100:1. Cells were infected at an MOI of 1-2.5 using standard protocols. Following 24 hrs of incubation at 40° C., the restrictive temperature for growth of ts369 mutant adenoviruses, infected cells are harvested, resuspended at 4×10$^6$ cells/ml, and incubated in 4% milk at room temperature (RT) for 20 minutes. Cells are then contacted with 0.5-1 μg/ml αVβ3-biotin in 4% milk at RT for 30 minutes and on ice for an additional 10 minutes. Cells are washed to remove any unbound αVβ3-biotin. Cells with surface bound αVβ3-biotin are positively selected with a magnetic bead conjugated anti-biotin antibody (Miltenyi Biotech) following the manufacturer's instructions. Isolated cells are double stained with FITC conjugated anti-human IgG-Fc (Pierce) and APC-conjugated streptavidin (Pierce) following manufacturers recommendations. Stained cells are examined on a flow cytometer and cells displaying both FITC and APC staining are isolated using a FACS machine. Flow cytometry profiles of cells representing various stages of the selection process, as well as the gate defining the selection criteria for sorting double positive cells are displayed in FIG. 13. Half of the isolated double positive cells are incubated at the permissive temperature of 37° C. to allow for the recovery of adenoviruses. Recovered virus may be subjected to a second round of selection. The second half of the cells are lysed in lysis buffer (10 mM EDTA and 0.6% SDS), phenol-chloroform extracted, ethanol precipitated to recover viral DNA. Virus encoded antibody sequences are PCR amplified from the isolated DNA and cloned using standard procedures. A sufficiently large number of clones are sequenced to determine the efficiency of the selection process. 86% of the clones from the selection experiment depicted in FIG. 13 contained Abegrin anti-αvβ3 integrin ScFvFc specific sequences; prior to selection Abegrin anti-αvβ3 integrin ScFvFc represents 1% of the starting artificial library.

Proof of principle selection experiment II: Artificial library used contains 100:1 ratio of viruses encoding Abegrin anti-αvβ3 integrin antibody and 3F2 anti-EphA2 ScFvFc. Biotinylated EphA2 ligand is used for detection of cell surface displayed 3F2 anti-EphA2 ScFvFc. Experiment was performed as described in paragraph [0250]. 34% of the clones derived from cells isolated in the selection experiment depicted in FIG. 14 contained 3F2 anti-EphA2 ScFvFc specific sequences; prior to selection 3F2 anti-EphA2 ScFvFc represents 1% of the starting artificial library.

Proof of principle selection experiment III: Artificial library used contains 100:1 ratio of viruses encoding an anti-PCDGF full length antibody and the 10C2 anti-EphA2 full length antibody. Biotinylated EphA2 ligand is used for detection of cell surface displayed 10C2 anti-EphA2 antibody. Experiment was performed as described in paragraph [0250]. 87% of the clones derived from cells isolated in the selection experiment depicted in FIG. 15 contained 10C2 anti-EphA2 antibody specific sequences; prior to selection 10C2 anti-EphA2 antibody represents 1% of the starting artificial library.

Whereas, particular embodiments of the invention have been described above for purposes of description, it will be appreciated by those skilled in the art that numerous variations of the details may be made without departing from the invention as described in the appended claims.

All publications, patents and patent applications mentioned in this specification are herein incorporated by reference into the specification to the same extent as if each individual publication, patent or patent application was specifically and individually indicated to be incorporated herein by reference.

The invention claimed is:

1. An isolated antibody comprising a variant human IgG1 Fc region having a reduced affinity for an effector molecule wherein said human IgG1 Fc region comprises an amino acid substitution, insertion or combination thereof selected from the group consisting of: W277T; K246R/L251E/T260R; InR234/235; InV235/236; InR236/237; InR237/238; InV238/239; InN238/239; InL238/239; InE238/239; InG238/239; InS239/240; InG240/241; InE240/241; InG240/241/I198T; InL238/239/P238Q; InE238/239N348A; InS239/240/V266A; InR237/238/G236A, wherein the numbering is according to EU index as set forth in Kabat.

2. The antibody of claim 1, wherein the effector molecule is selected from the group consisting of C1q, FcγRI, FcγRII and FcγRIIIA.

3. The antibody of claim 1, wherein the antibody has reduced effector function.

4. The antibody of claim 3, wherein the effector function is antibody-dependent cell-mediated cytotoxicity (ADCC.

5. The antibody of claim 1, wherein the human IgG1 Fc region has a reduced affinity for C1q, FcγRI, FcγRII and FcγRIIIA.

6. The antibody of claim 3, wherein the effector function is complement dependent cytotoxicity (CDC).

7. An Fc fusion protein comprising a human IgG1 Fc region having a reduced affinity for an effector molecule wherein said human IgG1 Fc region comprises an amino acid substitution, insertion or combination thereof selected from the group consisting of: W277T; K246R/L251E/T260R; InR234/235; InV235/236; InR236/237; InR237/238; InV238/239; InN238/239; InL238/239; InE238/239; InG238/239; InS239/240; InG240/241; InE240/241; InG240/241/I198T; InL238/239/P238Q; InE238/

239N348A; InS239/240/V266A; InR237/238/G236A, wherein the numbering is according to EU index as set forth in Kabat.

8. The Fc fusion protein of claim 7, wherein the effector molecule is selected from the group consisting of C1q, FcγRI, FcγRII and FcγRIIIA.

9. The Fc fusion protein of claim 7, wherein the human IgG1 Fc region has a reduced affinity for C1q, FcγRI, FcγRII and FcγRIIIA.

10. The Fc fusion protein of claim 7, wherein the antibody has reduced effector function.

11. The Fc fusion protein of claim 10, wherein the effector function is ADCC.

12. The Fc fusion protein of claim 10, wherein the effector function is CDC.

* * * * *

UNITED STATES PATENT AND TRADEMARK OFFICE
CERTIFICATE OF CORRECTION

PATENT NO. : 8,409,568 B2  Page 1 of 1
APPLICATION NO. : 12/837208
DATED : April 2, 2013
INVENTOR(S) : Gao et al.

It is certified that error appears in the above-identified patent and that said Letters Patent is hereby corrected as shown below:

In the Claims

In Column 113, Line 51, in Claim 1, after "comprising a", delete "variant".

In Column 113, Line 60, in Claim 1, delete "239N348A;" and insert -- 239/V348A; --, therefor.

In Column 114, Line 51, in Claim 4, delete "(ADCC." and insert -- (ADCC). --, therefor.

In Column 115, Line 1, in Claim 7, delete "239N348A;" and insert -- 239/V348A; --, therefor.

Signed and Sealed this
Twenty-first Day of May, 2013

Teresa Stanek Rea
*Acting Director of the United States Patent and Trademark Office*

SEQUENCE LISTING

<160> NUMBER OF SEQ ID NOS: 112

<210> SEQ ID NO 1
<211> LENGTH: 19
<212> TYPE: PRT
<213> ORGANISM: Aphtovirus A

<400> SEQUENCE: 1

Leu Leu Asn Phe Asp Leu Leu Lys Leu Ala Gly Asp Val Glu Ser Asn
1               5                   10                  15

Pro Gly Pro

<210> SEQ ID NO 2
<211> LENGTH: 19
<212> TYPE: PRT
<213> ORGANISM: Aphtovirus A

<400> SEQUENCE: 2

Thr Leu Asn Phe Asp Leu Leu Lys Leu Ala Gly Asp Val Glu Ser Asn
1               5                   10                  15

Pro Gly Pro

<210> SEQ ID NO 3
<211> LENGTH: 13
<212> TYPE: PRT
<213> ORGANISM: Aphtovirus A

<400> SEQUENCE: 3

Leu Lys Leu Ala Gly Asp Val Glu Ser Asn Pro Gly Pro
1               5                   10

<210> SEQ ID NO 4
<211> LENGTH: 17
<212> TYPE: PRT
<213> ORGANISM: Aphtovirus A

<400> SEQUENCE: 4

Asn Phe Asp Leu Leu Lys Leu Ala Gly Asp Val Glu Ser Asn Pro Gly
1               5                   10                  15

Pro

<210> SEQ ID NO 5
<211> LENGTH: 20
<212> TYPE: PRT
<213> ORGANISM: Aphtovirus A

<400> SEQUENCE: 5

Gln Leu Leu Asn Phe Asp Leu Leu Lys Leu Ala Gly Asp Val Glu Ser
1               5                   10                  15

Asn Pro Gly Pro
            20

<210> SEQ ID NO 6
<211> LENGTH: 24
<212> TYPE: PRT
<213> ORGANISM: Aphtovirus O

<400> SEQUENCE: 6

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 7
<211> LENGTH: 58
<212> TYPE: PRT
<213> ORGANISM: Aphtovirus O

<400> SEQUENCE: 7

Val Thr Glu Leu Leu Tyr Arg Met Lys Arg Ala Glu Thr Tyr Cys Pro
1               5                   10                  15

Arg Pro Leu Leu Ala Ile His Pro Thr Glu Ala Arg His Lys Gln Lys
            20                  25                  30

Ile Val Ala Pro Val Lys Gln Thr Leu Asn Phe Asp Leu Leu Lys Leu
            35                  40                  45

Ala Gly Asp Val Glu Ser Asn Pro Gly Pro
        50                  55

<210> SEQ ID NO 8
<211> LENGTH: 40
<212> TYPE: PRT
<213> ORGANISM: Aphtovirus O

<400> SEQUENCE: 8

Leu Leu Ala Ile His Pro Thr Glu Ala Arg His Lys Gln Lys Ile Val
1               5                   10                  15

Ala Pro Val Lys Gln Thr Leu Asn Phe Asp Leu Leu Lys Leu Ala Gly
            20                  25                  30

Asp Val Glu Ser Asn Pro Gly Pro
        35                  40

<210> SEQ ID NO 9
<211> LENGTH: 33
<212> TYPE: PRT
<213> ORGANISM: Aphtovirus O

<400> SEQUENCE: 9

Glu Ala Arg His Lys Gln Lys Ile Val Ala Pro Val Lys Gln Thr Leu
1               5                   10                  15

Asn Phe Asp Leu Leu Lys Leu Ala Gly Asp Val Glu Ser Asn Pro Gly
            20                  25                  30

Pro

<210> SEQ ID NO 10
<211> LENGTH: 72
<212> TYPE: DNA
<213> ORGANISM: artificial
<220> FEATURE:
<223> OTHER INFORMATION: PCR primer

<400> SEQUENCE: 10
gcttgaggtc tagacatata tatgggtgac aatgacatcc actttgcctt tctctccaca       60
ggtgtccact cc                                                           72

<210> SEQ ID NO 11
<211> LENGTH: 24
<212> TYPE: DNA
<213> ORGANISM: artificial
<220> FEATURE:
<223> OTHER INFORMATION: PCR primer

<400> SEQUENCE: 11
aacctctaca aatgtggtat ggct                                              24

<210> SEQ ID NO 12
<211> LENGTH: 39
<212> TYPE: DNA
<213> ORGANISM: artificial
<220> FEATURE:
<223> OTHER INFORMATION: PCR primer
<220> FEATURE:
<221> NAME/KEY: misc_feature
<222> LOCATION: (19)..(20)
<223> OTHER INFORMATION: n is a, c, g, or t

<400> SEQUENCE: 12
acatgcccac cgtgcccann scctgaactc ctgggggga                              39

<210> SEQ ID NO 13
<211> LENGTH: 42
<212> TYPE: DNA
<213> ORGANISM: artificial
<220> FEATURE:
<223> OTHER INFORMATION: PCR primer
<220> FEATURE:
<221> NAME/KEY: misc_feature
<222> LOCATION: (22)..(23)
<223> OTHER INFORMATION: n is a, c, g, or t

<400> SEQUENCE: 13
acatgcccac cgtgcccagc annsgaactc ctgggggac cg                42

<210> SEQ ID NO 14
<211> LENGTH: 45
<212> TYPE: DNA
<213> ORGANISM: artificial
<220> FEATURE:
<223> OTHER INFORMATION: PCR primer
<220> FEATURE:
<221> NAME/KEY: misc_feature
<222> LOCATION: (25)..(26)
<223> OTHER INFORMATION: n is a, c, g, or t

<400> SEQUENCE: 14
acatgcccac cgtgcccagc acctnnsctc ctgggggac cgtca           45

<210> SEQ ID NO 15
<211> LENGTH: 18
<212> TYPE: DNA
<213> ORGANISM: artificial
<220> FEATURE:
<223> OTHER INFORMATION: PCR primer

<400> SEQUENCE: 15
tgggcacggt gggcatgt                                         18

<210> SEQ ID NO 16
<211> LENGTH: 39
<212> TYPE: DNA
<213> ORGANISM: artificial
<220> FEATURE:
<223> OTHER INFORMATION: PCR primer
<220> FEATURE:
<221> NAME/KEY: misc_feature
<222> LOCATION: (19)..(20)
<223> OTHER INFORMATION: n is a, c, g, or t

<400> SEQUENCE: 16
gggggaccgt cagtcttcnn sttcccccca aaacccaag                  39

<210> SEQ ID NO 17
<211> LENGTH: 51
<212> TYPE: DNA
<213> ORGANISM: artificial
<220> FEATURE:
<223> OTHER INFORMATION: PCR primer
<220> FEATURE:
<221> NAME/KEY: misc_feature
<222> LOCATION: (31)..(32)
<223> OTHER INFORMATION: n is a, c, g, or t

<400> SEQUENCE: 17
gggggaccgt cagtcttcct cttcccccca nnscccaagg acaccctcat g    51

<210> SEQ ID NO 18
<211> LENGTH: 18

```
<212> TYPE: DNA
<213> ORGANISM: artificial
<220> FEATURE:
<223> OTHER INFORMATION: PCR primer

<400> SEQUENCE: 18
gaagactgac ggtccccc                                                    18

<210> SEQ ID NO 19
<211> LENGTH: 39
<212> TYPE: DNA
<213> ORGANISM: artificial
<220> FEATURE:
<223> OTHER INFORMATION: PCR primer
<220> FEATURE:
<221> NAME/KEY: misc_feature
<222> LOCATION: (19)..(20)
<223> OTHER INFORMATION: n is a, c, g, or t

<400> SEQUENCE: 19
cccccaaaac ccaaggacnn sctcatgatc tcccggacc                              39

<210> SEQ ID NO 20
<211> LENGTH: 42
<212> TYPE: DNA
<213> ORGANISM: artificial
<220> FEATURE:
<223> OTHER INFORMATION: PCR primer
<220> FEATURE:
<221> NAME/KEY: misc_feature
<222> LOCATION: (22)..(23)
<223> OTHER INFORMATION: n is a, c, g, or t

<400> SEQUENCE: 20
cccccaaaac ccaaggacac cnnsatgatc tcccggaccc ct                          42

<210> SEQ ID NO 21
<211> LENGTH: 18
<212> TYPE: DNA
<213> ORGANISM: artificial
<220> FEATURE:
<223> OTHER INFORMATION: PCR primer

<400> SEQUENCE: 21
gtccttgggt tttgggggg                                                    18

<210> SEQ ID NO 22
<211> LENGTH: 39
<212> TYPE: DNA
<213> ORGANISM: artificial
<220> FEATURE:
<223> OTHER INFORMATION: PCR primer
<220> FEATURE:
<221> NAME/KEY: misc_feature
<222> LOCATION: (19)..(20)
<223> OTHER INFORMATION: n is a, c, g, or t

<400> SEQUENCE: 22
ctcatgatct cccggaccnn sgaggtcaca tgcgtggtg                              39

<210> SEQ ID NO 23
<211> LENGTH: 45
<212> TYPE: DNA
<213> ORGANISM: artificial
<220> FEATURE:
<223> OTHER INFORMATION: PCR primer
<220> FEATURE:
<221> NAME/KEY: misc_feature
<222> LOCATION: (25)..(26)
<223> OTHER INFORMATION: n is a, c, g, or t
```

<400> SEQUENCE: 23
ctcatgatct cccggacccc tgagnnsaca tgcgtggtgg tggac                    45

<210> SEQ ID NO 24
<211> LENGTH: 48
<212> TYPE: DNA
<213> ORGANISM: artificial
<220> FEATURE:
<223> OTHER INFORMATION: PCR primer
<220> FEATURE:
<221> NAME/KEY: misc_feature
<222> LOCATION: (28)..(29)
<223> OTHER INFORMATION: n is a, c, g, or t

<400> SEQUENCE: 24
ctcatgatct cccggacccc tgaggtcnns tgcgtggtgg tggacgtg                 48

<210> SEQ ID NO 25
<211> LENGTH: 51
<212> TYPE: DNA
<213> ORGANISM: artificial
<220> FEATURE:
<223> OTHER INFORMATION: PCR primer
<220> FEATURE:
<221> NAME/KEY: misc_feature
<222> LOCATION: (31)..(32)
<223> OTHER INFORMATION: n is a, c, g, or t

<400> SEQUENCE: 25
ctcatgatct cccggacccc tgaggtcaca nnsgtggtgg tggacgtgag c             51

<210> SEQ ID NO 26
<211> LENGTH: 18
<212> TYPE: DNA
<213> ORGANISM: artificial
<220> FEATURE:
<223> OTHER INFORMATION: PCR primer

<400> SEQUENCE: 26
ggtccgggag atcatgag                                                  18

<210> SEQ ID NO 27
<211> LENGTH: 39
<212> TYPE: DNA
<213> ORGANISM: artificial
<220> FEATURE:
<223> OTHER INFORMATION: PCR primer
<220> FEATURE:
<221> NAME/KEY: misc_feature
<222> LOCATION: (19)..(20)
<223> OTHER INFORMATION: n is a, c, g, or t

<400> SEQUENCE: 27
agccacgaag accctgagnn saagttcaac tggtacgtg                           39

<210> SEQ ID NO 28
<211> LENGTH: 42
<212> TYPE: DNA
<213> ORGANISM: artificial
<220> FEATURE:
<223> OTHER INFORMATION: PCR primer
<220> FEATURE:
<221> NAME/KEY: misc_feature
<222> LOCATION: (22)..(23)
<223> OTHER INFORMATION: n is a, c, g, or t

<400> SEQUENCE: 28
agccacgaag accctgaggt cnnsttcaac tggtacgtgg ac                       42

```
<210> SEQ ID NO 29
<211> LENGTH: 45
<212> TYPE: DNA
<213> ORGANISM: artificial
<220> FEATURE:
<223> OTHER INFORMATION: PCR primer
<220> FEATURE:
<221> NAME/KEY: misc_feature
<222> LOCATION: (25)..(26)
<223> OTHER INFORMATION: n is a, c, g, or t

<400> SEQUENCE: 29
agccacgaag accctgaggt caagnnsaac tggtacgtgg acggc            45

<210> SEQ ID NO 30
<211> LENGTH: 51
<212> TYPE: DNA
<213> ORGANISM: artificial
<220> FEATURE:
<223> OTHER INFORMATION: PCR primer
<220> FEATURE:
<221> NAME/KEY: misc_feature
<222> LOCATION: (31)..(32)
<223> OTHER INFORMATION: n is a, c, g, or t

<400> SEQUENCE: 30
agccacgaag accctgaggt caagttcaac nnstacgtgg acggcgtgga g      51

<210> SEQ ID NO 31
<211> LENGTH: 18
<212> TYPE: DNA
<213> ORGANISM: artificial
<220> FEATURE:
<223> OTHER INFORMATION: PCR primer

<400> SEQUENCE: 31
ctcagggtct tcgtggct                                          18

<210> SEQ ID NO 32
<211> LENGTH: 39
<212> TYPE: DNA
<213> ORGANISM: artificial
<220> FEATURE:
<223> OTHER INFORMATION: PCR primer
<220> FEATURE:
<221> NAME/KEY: misc_feature
<222> LOCATION: (19)..(20)
<223> OTHER INFORMATION: n is a, c, g, or t

<400> SEQUENCE: 32
ttcaactggt acgtggacnn sgtggaggtg cataatgcc                   39

<210> SEQ ID NO 33
<211> LENGTH: 42
<212> TYPE: DNA
<213> ORGANISM: artificial
<220> FEATURE:
<223> OTHER INFORMATION: PCR primer
<220> FEATURE:
<221> NAME/KEY: misc_feature
<222> LOCATION: (22)..(23)
<223> OTHER INFORMATION: n is a, c, g, or t

<400> SEQUENCE: 33
ttcaactggt acgtggacgg cnnsgaggtg cataatgcca ag               42

<210> SEQ ID NO 34
<211> LENGTH: 48
```

<212> TYPE: DNA
<213> ORGANISM: artificial
<220> FEATURE:
<223> OTHER INFORMATION: PCR primer
<220> FEATURE:
<221> NAME/KEY: misc_feature
<222> LOCATION: (28)..(29)
<223> OTHER INFORMATION: n is a, c, g, or t

<400> SEQUENCE: 34
ttcaactggt acgtggacgg cgtggagnns cataatgcca agacaaag                48

<210> SEQ ID NO 35
<211> LENGTH: 18
<212> TYPE: DNA
<213> ORGANISM: artificial
<220> FEATURE:
<223> OTHER INFORMATION: PCR primer

<400> SEQUENCE: 35
gtccacgtac cagttgaa                                                 18

<210> SEQ ID NO 36
<211> LENGTH: 39
<212> TYPE: DNA
<213> ORGANISM: artificial
<220> FEATURE:
<223> OTHER INFORMATION: PCR primer
<220> FEATURE:
<221> NAME/KEY: misc_feature
<222> LOCATION: (19)..(20)
<223> OTHER INFORMATION: n is a, c, g, or t

<400> SEQUENCE: 36
acatgcccac cgtgcccann sgcacctgaa ctcctgggg                          39

<210> SEQ ID NO 37
<211> LENGTH: 42
<212> TYPE: DNA
<213> ORGANISM: artificial
<220> FEATURE:
<223> OTHER INFORMATION: PCR primer
<220> FEATURE:
<221> NAME/KEY: misc_feature
<222> LOCATION: (22)..(23)
<223> OTHER INFORMATION: n is a, c, g, or t

<400> SEQUENCE: 37
acatgcccac cgtgcccagc annscctgaa ctcctggggg ga                      42

<210> SEQ ID NO 38
<211> LENGTH: 45
<212> TYPE: DNA
<213> ORGANISM: artificial
<220> FEATURE:
<223> OTHER INFORMATION: PCR primer
<220> FEATURE:
<221> NAME/KEY: misc_feature
<222> LOCATION: (25)..(26)
<223> OTHER INFORMATION: n is a, c, g, or t

<400> SEQUENCE: 38
acatgcccac cgtgcccagc acctnnsgaa ctcctggggg gaccg                   45

<210> SEQ ID NO 39
<211> LENGTH: 48
<212> TYPE: DNA
<213> ORGANISM: artificial
<220> FEATURE:
<223> OTHER INFORMATION: PCR primer

```
<220> FEATURE:
<221> NAME/KEY: misc_feature
<222> LOCATION: (28)..(29)
<223> OTHER INFORMATION: n is a, c, g, or t

<400> SEQUENCE: 39
acatgcccac cgtgcccagc acctgaanns ctcctgggggg gaccgtca                    48

<210> SEQ ID NO 40
<211> LENGTH: 57
<212> TYPE: DNA
<213> ORGANISM: artificial
<220> FEATURE:
<223> OTHER INFORMATION: PCR primer
<220> FEATURE:
<221> NAME/KEY: misc_feature
<222> LOCATION: (31)..(32)
<223> OTHER INFORMATION: n is a, c, g, or t

<400> SEQUENCE: 40
acatgcccac cgtgcccagc acctgaactc nnsctgggggg gaccgtcagt cttcctc          57

<210> SEQ ID NO 41
<211> LENGTH: 60
<212> TYPE: DNA
<213> ORGANISM: artificial
<220> FEATURE:
<223> OTHER INFORMATION: PCR primer
<220> FEATURE:
<221> NAME/KEY: misc_feature
<222> LOCATION: (34)..(35)
<223> OTHER INFORMATION: n is a, c, g, or t

<400> SEQUENCE: 41
acatgcccac cgtgcccagc acctgaactc ctgnnsgggg gaccgtcagt cttcctcttc        60

<210> SEQ ID NO 42
<211> LENGTH: 39
<212> TYPE: DNA
<213> ORGANISM: artificial
<220> FEATURE:
<223> OTHER INFORMATION: PCR primer
<220> FEATURE:
<221> NAME/KEY: misc_feature
<222> LOCATION: (19)..(20)
<223> OTHER INFORMATION: n is a, c, g, or t

<400> SEQUENCE: 42
gcacctgaac tcctggggnn sggaccgtca gtcttcctc                              39

<210> SEQ ID NO 43
<211> LENGTH: 42
<212> TYPE: DNA
<213> ORGANISM: artificial
<220> FEATURE:
<223> OTHER INFORMATION: PCR primer
<220> FEATURE:
<221> NAME/KEY: misc_feature
<222> LOCATION: (22)..(23)
<223> OTHER INFORMATION: n is a, c, g, or t

<400> SEQUENCE: 43
gcacctgaac tcctgggggg annsccgtca gtcttcctct tc                          42

<210> SEQ ID NO 44
<211> LENGTH: 45
<212> TYPE: DNA
<213> ORGANISM: artificial
<220> FEATURE:
<223> OTHER INFORMATION: PCR primer
```

```
<220> FEATURE:
<221> NAME/KEY: misc_feature
<222> LOCATION: (25)..(26)
<223> OTHER INFORMATION: n is a, c, g, or t

<400> SEQUENCE: 44
gcacctgaac tcctgggggg accgnnstca gtcttcctct tcccc                      45

<210> SEQ ID NO 45
<211> LENGTH: 48
<212> TYPE: DNA
<213> ORGANISM: artificial
<220> FEATURE:
<223> OTHER INFORMATION: PCR primer
<220> FEATURE:
<221> NAME/KEY: misc_feature
<222> LOCATION: (28)..(29)
<223> OTHER INFORMATION: n is a, c, g, or t

<400> SEQUENCE: 45
gcacctgaac tctgggggg accgtcanns gtcttcctct tcccccca                    48

<210> SEQ ID NO 46
<211> LENGTH: 51
<212> TYPE: DNA
<213> ORGANISM: artificial
<220> FEATURE:
<223> OTHER INFORMATION: PCR primer
<220> FEATURE:
<221> NAME/KEY: misc_feature
<222> LOCATION: (31)..(32)
<223> OTHER INFORMATION: n is a, c, g, or t

<400> SEQUENCE: 46
gcacctgaac tcctgggggg accgtcagtc nnsttcctct tccccccaaa a               51

<210> SEQ ID NO 47
<211> LENGTH: 18
<212> TYPE: DNA
<213> ORGANISM: artificial
<220> FEATURE:
<223> OTHER INFORMATION: PCR primer

<400> SEQUENCE: 47
ccccaggagt tcaggtgc                                                    18

<210> SEQ ID NO 48
<211> LENGTH: 60
<212> TYPE: DNA
<213> ORGANISM: artificial
<220> FEATURE:
<223> OTHER INFORMATION: PCR primer

<400> SEQUENCE: 48
acgggtagta cctgaagtgg ttccacttcc tttatttggt ttacccggag acagggagag      60

<210> SEQ ID NO 49
<211> LENGTH: 60
<212> TYPE: DNA
<213> ORGANISM: artificial
<220> FEATURE:
<223> OTHER INFORMATION: PCR primer

<400> SEQUENCE: 49
caaacctgtc aacgtgaaac acgtgtgccc agatagaaga cgggtagtac ctgaagtggt      60

<210> SEQ ID NO 50
<211> LENGTH: 72
```

```
<212> TYPE: DNA
<213> ORGANISM: artificial
<220> FEATURE:
<223> OTHER INFORMATION: PCR primer

<400> SEQUENCE: 50
tgaattcgcg gccgctcaag tcagcaagcc catggttact agcgtcccaa gcaaacctgt       60
caacgtgaaa ca                                                          72

<210> SEQ ID NO 51
<211> LENGTH: 42
<212> TYPE: DNA
<213> ORGANISM: artificial
<220> FEATURE:
<223> OTHER INFORMATION: PCR primer

<400> SEQUENCE: 51
aagcttcggt ccgccaccat ggcaactgaa gatctcccaa ag                         42

<210> SEQ ID NO 52
<211> LENGTH: 39
<212> TYPE: DNA
<213> ORGANISM: artificial
<220> FEATURE:
<223> OTHER INFORMATION: PCR primer

<400> SEQUENCE: 52
gtctgccgaa ccgctgcctg ccaaaccttg agtgatggt                             39

<210> SEQ ID NO 53
<211> LENGTH: 30
<212> TYPE: DNA
<213> ORGANISM: artificial
<220> FEATURE:
<223> OTHER INFORMATION: PCR primer

<400> SEQUENCE: 53
ggcagcggtt cggcagaccc ctccaaggac                                       30

<210> SEQ ID NO 54
<211> LENGTH: 35
<212> TYPE: DNA
<213> ORGANISM: artificial
<220> FEATURE:
<223> OTHER INFORMATION: PCR primer

<400> SEQUENCE: 54 cagggggctag cttactgctg aacggcgtcg agcgg                                35

<210> SEQ ID NO 55
<211> LENGTH: 45
<212> TYPE: DNA
<213> ORGANISM: artificial
<220> FEATURE:
<223> OTHER INFORMATION: PCR primer

<400> SEQUENCE: 55
tcaatgaatt cgcggccgct catttacccg gagacaggga gaggc                      45

<210> SEQ ID NO 56
<211> LENGTH: 37
<212> TYPE: PRT
<213> ORGANISM: Mus musculus

<400> SEQUENCE: 56

Asp Lys Leu Val Lys Cys Gly Gly Ile Ser Leu Leu Val Gln Asn Thr
```

```
                1               5                  10                 15
Ser Trp Met Leu Leu Leu Leu Ser Leu Ser Leu Leu Gln Ala Leu
                        20                 25                 30

Asp Phe Ile Ser Leu
                35

<210> SEQ ID NO 57
<211> LENGTH: 50
<212> TYPE: PRT
<213> ORGANISM: Dictyostelium discoideum

<400> SEQUENCE: 57

Pro Ser Pro Thr Pro Thr Glu Thr Ala Thr Pro Ser Pro Thr Pro Lys
1               5                  10                 15

Pro Thr Ser Thr Pro Glu Glu Thr Glu Ala Pro Ser Ser Ala Thr Thr
                20                 25                 30

Leu Ile Ser Pro Leu Ser Leu Ile Val Ile Phe Ile Ser Phe Val Leu
            35                 40                 45

Leu Ile
    50

<210> SEQ ID NO 58
<211> LENGTH: 39
<212> TYPE: PRT
<213> ORGANISM: artificial
<220> FEATURE:
<223> OTHER INFORMATION: signal sequence for attachment of GPI

<400> SEQUENCE: 58

Leu Val Pro Arg Gly Ser Ile Glu Gly Arg Gly Thr Ser Ile Thr Ala
1               5                  10                 15

Tyr Asn Ser Glu Gly Glu Ser Ala Glu Phe Phe Phe Leu Leu Ile Leu
                20                 25                 30

Leu Leu Leu Leu Val Leu Val
                35

<210> SEQ ID NO 59
<211> LENGTH: 28
<212> TYPE: PRT
<213> ORGANISM: artificial
<220> FEATURE:
<223> OTHER INFORMATION: signal sequence for attachment of GPI

<400> SEQUENCE: 59

Thr Ser Ile Thr Ala Tyr Lys Ser Glu Gly Glu Ser Ala Glu Phe Phe
1               5                  10                 15

Phe Leu Leu Ile Leu Leu Leu Leu Leu Val Leu Val
                20                 25

<210> SEQ ID NO 60
<211> LENGTH: 37
<212> TYPE: PRT
<213> ORGANISM: Homo sapiens

<400> SEQUENCE: 60

Ser Asn Lys Gly Ser Gly Thr Thr Ser Gly Thr Ala Arg Leu Leu Ser
1               5                  10                 15

Gly His Thr Cys Phe Thr Leu Thr Gly Leu Leu Gly Thr Leu Val Ile
                20                 25                 30

Met Gly Leu Leu Thr
                35
```

```
<210> SEQ ID NO 61
<211> LENGTH: 37
<212> TYPE: PRT
<213> ORGANISM: Homo sapiens

<400> SEQUENCE: 61

Pro Asn Lys Gly Ser Gly Thr Thr Ser Gly Thr Thr Arg Leu Leu Ser
1               5                   10                  15

Gly His Thr Cys Phe Thr Leu Thr Gly Leu Leu Gly Thr Leu Val Thr
            20                  25                  30

Met Gly Leu Leu Thr
        35

<210> SEQ ID NO 62
<211> LENGTH: 24
<212> TYPE: PRT
<213> ORGANISM: Homo sapiens

<400> SEQUENCE: 62

Pro Asp His Ser Ala Ala Thr Lys Pro Ser Leu Phe Leu Phe Leu Val
1               5                   10                  15

Ser Leu Leu His Ile Phe Phe Lys
            20

<210> SEQ ID NO 63
<211> LENGTH: 50
<212> TYPE: DNA
<213> ORGANISM: artificial
<220> FEATURE:
<223> OTHER INFORMATION: PCR primer

<400> SEQUENCE: 63
gcctttctct ccacaggtgt acactcccag gtkcagctgg tgcagtctgg          50

<210> SEQ ID NO 64
<211> LENGTH: 50
<212> TYPE: DNA
<213> ORGANISM: artificial
<220> FEATURE:
<223> OTHER INFORMATION: PCR primer

<400> SEQUENCE: 64
gcctttctct ccacaggtgt acactcccag gtccagcttg tgcagtctgg          50

<210> SEQ ID NO 65
<211> LENGTH: 50
<212> TYPE: DNA
<213> ORGANISM: artificial
<220> FEATURE:
<223> OTHER INFORMATION: PCR primer

<400> SEQUENCE: 65
gcctttctct ccacaggtgt acactccsag gtccagctgg tacagtctgg          50

<210> SEQ ID NO 66
<211> LENGTH: 50
<212> TYPE: DNA
<213> ORGANISM: artificial
<220> FEATURE:
<223> OTHER INFORMATION: PCR primer

<400> SEQUENCE: 66
gcctttctct ccacaggtgt acactcccar atgcagctgg tgcagtctgg          50
```

```
<210> SEQ ID NO 67
<211> LENGTH: 50
<212> TYPE: DNA
<213> ORGANISM: artificial
<220> FEATURE:
<223> OTHER INFORMATION: PCR primer

<400> SEQUENCE: 67
gcctttctct ccacaggtgt acactcccag atcaccttga aggagtctgg          50

<210> SEQ ID NO 68
<211> LENGTH: 50
<212> TYPE: DNA
<213> ORGANISM: artificial
<220> FEATURE:
<223> OTHER INFORMATION: PCR primer

<400> SEQUENCE: 68
gcctttctct ccacaggtgt acactcccag gtcaccttga aggagtctgg          50

<210> SEQ ID NO 69
<211> LENGTH: 48
<212> TYPE: DNA
<213> ORGANISM: artificial
<220> FEATURE:
<223> OTHER INFORMATION: PCR primer

<400> SEQUENCE: 69
gcctttctct ccacaggtgt acactccgar gtgcagctgg tggagtct            48

<210> SEQ ID NO 70
<211> LENGTH: 50
<212> TYPE: DNA
<213> ORGANISM: artificial
<220> FEATURE:
<223> OTHER INFORMATION: PCR primer

<400> SEQUENCE: 70
gcctttctct ccacaggtgt acactcccag gtgcagctgg tggagtctgg          50

<210> SEQ ID NO 71
<211> LENGTH: 50
<212> TYPE: DNA
<213> ORGANISM: artificial
<220> FEATURE:
<223> OTHER INFORMATION: PCR primer

<400> SEQUENCE: 71
gcctttctct ccacaggtgt acactccgag gtgcagctgt tggagtctgg          50

<210> SEQ ID NO 72
<211> LENGTH: 50
<212> TYPE: DNA
<213> ORGANISM: artificial
<220> FEATURE:
<223> OTHER INFORMATION: PCR primer

<400> SEQUENCE: 72
gcctttctct ccacaggtgt acactccgag gtgcagctgg tgcagwcygg          50

<210> SEQ ID NO 73
<211> LENGTH: 50
<212> TYPE: DNA
<213> ORGANISM: artificial
<220> FEATURE:
<223> OTHER INFORMATION: PCR primer

<400> SEQUENCE: 73
```

```
gcctttctct ccacaggtgt acactcccag stgcagctgc aggagtcsgg           50
```

<210> SEQ ID NO 74
<211> LENGTH: 50
<212> TYPE: DNA
<213> ORGANISM: artificial
<220> FEATURE:
<223> OTHER INFORMATION: PCR primer

<400> SEQUENCE: 74

```
gcctttctct ccacaggtgt acactcccag gtgcagctac agcagtgggg           50
```

<210> SEQ ID NO 75
<211> LENGTH: 50
<212> TYPE: DNA
<213> ORGANISM: artificial
<220> FEATURE:
<223> OTHER INFORMATION: PCR primer

<400> SEQUENCE: 75

```
gcctttctct ccacaggtgt acactccgar gtgcagctgg tgcagtctgg           50
```

<210> SEQ ID NO 76
<211> LENGTH: 50
<212> TYPE: DNA
<213> ORGANISM: artificial
<220> FEATURE:
<223> OTHER INFORMATION: PCR primer

<400> SEQUENCE: 76

```
gcctttctct ccacaggtgt acactcccag gtacagctgc agcagtcagg           50
```

<210> SEQ ID NO 77
<211> LENGTH: 50
<212> TYPE: DNA
<213> ORGANISM: artificial
<220> FEATURE:
<223> OTHER INFORMATION: PCR primer

<400> SEQUENCE: 77

```
gcctttctct ccacaggtgt acactcccag gtgcagctgg tgcaatctgg           50
```

<210> SEQ ID NO 78
<211> LENGTH: 48
<212> TYPE: DNA
<213> ORGANISM: artificial
<220> FEATURE:
<223> OTHER INFORMATION: PCR primer

<400> SEQUENCE: 78

```
gaagacggat gggcccttgg tcgacgctga ggagacrgtg accagggt             48
```

<210> SEQ ID NO 79
<211> LENGTH: 48
<212> TYPE: DNA
<213> ORGANISM: artificial
<220> FEATURE:
<223> OTHER INFORMATION: PCR primer

<400> SEQUENCE: 79

```
gaagacggat gggcccttgg tcgacgctga agagacggtg accattgt             48
```

<210> SEQ ID NO 80
<211> LENGTH: 48
<212> TYPE: DNA
<213> ORGANISM: artificial

```
<220> FEATURE:
<223> OTHER INFORMATION: PCR primer

<400> SEQUENCE: 80
gaagacggat gggcccttgg tcgacgctga ggagacggtg accgtggt        48

<210> SEQ ID NO 81
<211> LENGTH: 47
<212> TYPE: DNA
<213> ORGANISM: artificial
<220> FEATURE:
<223> OTHER INFORMATION: PCR primer

<400> SEQUENCE: 81
ctctggctcc ccggggcgcg ctgtracatc cagatgaccc agtctcc         47

<210> SEQ ID NO 82
<211> LENGTH: 47
<212> TYPE: DNA
<213> ORGANISM: artificial
<220> FEATURE:
<223> OTHER INFORMATION: PCR primer

<400> SEQUENCE: 82
ctctggctcc ccggggcgcg ctgtgmcatc crgwtgaccc agtctcc         47

<210> SEQ ID NO 83
<211> LENGTH: 47
<212> TYPE: DNA
<213> ORGANISM: artificial
<220> FEATURE:
<223> OTHER INFORMATION: PCR primer

<400> SEQUENCE: 83
ctctggctcc ccggggcgcg ctgtgtcatc tggatgaccc agtctcc         47

<210> SEQ ID NO 84
<211> LENGTH: 47
<212> TYPE: DNA
<213> ORGANISM: artificial
<220> FEATURE:
<223> OTHER INFORMATION: PCR primer

<400> SEQUENCE: 84
ctctggctcc ccggggcgcg ctgtgatatt gtgatgaccc agactcc         47

<210> SEQ ID NO 85
<211> LENGTH: 47
<212> TYPE: DNA
<213> ORGANISM: artificial
<220> FEATURE:
<223> OTHER INFORMATION: PCR primer

<400> SEQUENCE: 85
ctctggctcc ccggggcgcg ctgtgatrtt gtgatgacwc agtctcc         47

<210> SEQ ID NO 86
<211> LENGTH: 47
<212> TYPE: DNA
<213> ORGANISM: artificial
<220> FEATURE:
<223> OTHER INFORMATION: PCR primer

<400> SEQUENCE: 86
ctctggctcc ccggggcgcg ctgtgaaatt gtgttgacrc agtctcc         47
```

```
<210> SEQ ID NO 87
<211> LENGTH: 47
<212> TYPE: DNA
<213> ORGANISM: artificial
<220> FEATURE:
<223> OTHER INFORMATION: PCR primer

<400> SEQUENCE: 87
ctctggctcc ccggggcgcg ctgtgaaata gtgatgacgc agtctcc                47

<210> SEQ ID NO 88
<211> LENGTH: 47
<212> TYPE: DNA
<213> ORGANISM: artificial
<220> FEATURE:
<223> OTHER INFORMATION: PCR primer

<400> SEQUENCE: 88
ctctggctcc ccggggcgcg ctgtgaaatt gtaatgacac agtctcc                47

<210> SEQ ID NO 89
<211> LENGTH: 47
<212> TYPE: DNA
<213> ORGANISM: artificial
<220> FEATURE:
<223> OTHER INFORMATION: PCR primer

<400> SEQUENCE: 89
ctctggctcc ccggggcgcg ctgtgacatc gtgatgaccc agtctcc                47

<210> SEQ ID NO 90
<211> LENGTH: 47
<212> TYPE: DNA
<213> ORGANISM: artificial
<220> FEATURE:
<223> OTHER INFORMATION: PCR primer

<400> SEQUENCE: 90
ctctggctcc ccggggcgcg ctgtgaaacg acactcacgc agtctcc                47

<210> SEQ ID NO 91
<211> LENGTH: 47
<212> TYPE: DNA
<213> ORGANISM: artificial
<220> FEATURE:
<223> OTHER INFORMATION: PCR primer

<400> SEQUENCE: 91
ctctggctcc ccggggcgcg ctgtgaaatt gtgctgactc agtctcc                47

<210> SEQ ID NO 92
<211> LENGTH: 45
<212> TYPE: DNA
<213> ORGANISM: artificial
<220> FEATURE:
<223> OTHER INFORMATION: PCR primer

<400> SEQUENCE: 92
gcatgctcga catcgattca ctaacactct cccctgttga agctc                  45

<210> SEQ ID NO 93
<211> LENGTH: 47
<212> TYPE: DNA
<213> ORGANISM: artificial
<220> FEATURE:
<223> OTHER INFORMATION: PCR primer

<400> SEQUENCE: 93
```
ctctggctcc ccggggcgcg ctgtcagtct gtgctgactc agccacc         47

<210> SEQ ID NO 94
<211> LENGTH: 47
<212> TYPE: DNA
<213> ORGANISM: artificial
<220> FEATURE:
<223> OTHER INFORMATION: PCR primer

<400> SEQUENCE: 94
ctctggctcc ccggggcgcg ctgtcagtct gtgytgacgc agccgcc         47

<210> SEQ ID NO 95
<211> LENGTH: 45
<212> TYPE: DNA
<213> ORGANISM: artificial
<220> FEATURE:
<223> OTHER INFORMATION: PCR primer

<400> SEQUENCE: 95
ctctggctcc ccggggcgcg ctgtcagtct gccctgactc agcct           45

<210> SEQ ID NO 96
<211> LENGTH: 45
<212> TYPE: DNA
<213> ORGANISM: artificial
<220> FEATURE:
<223> OTHER INFORMATION: PCR primer

<400> SEQUENCE: 96
ctctggctcc ccggggcgcg ctgttcctat gwgctgacwc agcca           45

<210> SEQ ID NO 97
<211> LENGTH: 47
<212> TYPE: DNA
<213> ORGANISM: artificial
<220> FEATURE:
<223> OTHER INFORMATION: PCR primer

<400> SEQUENCE: 97
ctctggctcc ccggggcgcg ctgttcctat gagctgacac agctacc         47

<210> SEQ ID NO 98
<211> LENGTH: 46
<212> TYPE: DNA
<213> ORGANISM: artificial
<220> FEATURE:
<223> OTHER INFORMATION: PCR primer

<400> SEQUENCE: 98
ctctggctcc ccggggcgcg ctgttcttct gagctgactc aggacc          46

<210> SEQ ID NO 99
<211> LENGTH: 46
<212> TYPE: DNA
<213> ORGANISM: artificial
<220> FEATURE:
<223> OTHER INFORMATION: PCR primer

<400> SEQUENCE: 99
ctctggctcc ccggggcgcg ctgttcctat gagctgatgc agccac          46

<210> SEQ ID NO 100
<211> LENGTH: 44
<212> TYPE: DNA
<213> ORGANISM: artificial

-continued

```
<220> FEATURE:
<223> OTHER INFORMATION: PCR primer

<400> SEQUENCE: 100
ctctggctcc ccggggcgcg ctgtcagcyt gtgctgactc aatc            44

<210> SEQ ID NO 101
<211> LENGTH: 44
<212> TYPE: DNA
<213> ORGANISM: artificial
<220> FEATURE:
<223> OTHER INFORMATION: PCR primer

<400> SEQUENCE: 101
ctctggctcc ccggggcgcg ctgtcwgsct gtgctgactc agcc            44

<210> SEQ ID NO 102
<211> LENGTH: 47
<212> TYPE: DNA
<213> ORGANISM: artificial
<220> FEATURE:
<223> OTHER INFORMATION: PCR primer

<400> SEQUENCE: 102
ctctggctcc ccggggcgcg ctgtaattt atgctgactc agccca          47

<210> SEQ ID NO 103
<211> LENGTH: 47
<212> TYPE: DNA
<213> ORGANISM: artificial
<220> FEATURE:
<223> OTHER INFORMATION: PCR primer

<400> SEQUENCE: 103
ctctggctcc ccggggcgcg ctgtcagrct gtggtgacyc aggagcc         47

<210> SEQ ID NO 104
<211> LENGTH: 47
<212> TYPE: DNA
<213> ORGANISM: artificial
<220> FEATURE:
<223> OTHER INFORMATION: PCR primer

<400> SEQUENCE: 104
ctctggctcc ccggggcgcg ctgtcaggca gggctgactc agccacc         47

<210> SEQ ID NO 105
<211> LENGTH: 46
<212> TYPE: DNA
<213> ORGANISM: artificial
<220> FEATURE:
<223> OTHER INFORMATION: PCR primer

<400> SEQUENCE: 105
gcatgctcga catcgattca ctatgaacat tctgtagggg ccactg          46

<210> SEQ ID NO 106
<211> LENGTH: 46
<212> TYPE: DNA
<213> ORGANISM: artificial
<220> FEATURE:
<223> OTHER INFORMATION: PCR primer

<400> SEQUENCE: 106
gcatgctcga catcgattca ctaagagcat tctgcagggg ccactg          46
```

-continued

<210> SEQ ID NO 107
<211> LENGTH: 21
<212> TYPE: DNA
<213> ORGANISM: artificial
<220> FEATURE:
<223> OTHER INFORMATION: PCR primer

<400> SEQUENCE: 107
ccatgggatg gagctgtatc a                                         21

<210> SEQ ID NO 108
<211> LENGTH: 27
<212> TYPE: DNA
<213> ORGANISM: artificial
<220> FEATURE:
<223> OTHER INFORMATION: PCR primer

<400> SEQUENCE: 108
ggagtgtaca cctgtggaga gaaaggc                                   27

<210> SEQ ID NO 109
<211> LENGTH: 27
<212> TYPE: PRT
<213> ORGANISM: Homo sapiens

<400> SEQUENCE: 109

Leu Leu Ile Gly Ile Ser Ile Ala Ser Leu Cys Leu Val Val Ala Leu
1               5                   10                  15

Leu Ala Leu Leu Cys His Leu Arg Lys Lys Gln
            20                  25

<210> SEQ ID NO 110
<211> LENGTH: 32
<212> TYPE: DNA
<213> ORGANISM: artificial
<220> FEATURE:
<223> OTHER INFORMATION: oligonucleotide for site directed mutagnensis

<400> SEQUENCE: 110
gagccggcgg cgcgggccca gcgaccgcga gc                             32

<210> SEQ ID NO 111
<211> LENGTH: 32
<212> TYPE: DNA
<213> ORGANISM: artificial
<220> FEATURE:
<223> OTHER INFORMATION: oligonucleotide for site directed mutagenesis

<400> SEQUENCE: 111
gctcgcggtc gctgggcccg cgccgccggc tc                             32

<210> SEQ ID NO 112
<211> LENGTH: 742
<212> TYPE: PRT
<213> ORGANISM: artificial
<220> FEATURE:
<223> OTHER INFORMATION: EphA2 extracellular domain fused to Fc region
      of IgG1

<400> SEQUENCE: 112

Gln Gly Lys Glu Val Val Leu Leu Asp Phe Ala Ala Ala Gly Gly Glu
1               5                   10                  15

Leu Gly Trp Leu Thr His Pro Tyr Gly Lys Gly Trp Asp Leu Met Gln
            20                  25                  30

Asn Ile Met Asn Asp Met Pro Ile Tyr Met Tyr Ser Val Cys Asn Val
        35                  40                  45

-continued

```
Met Ser Gly Asp Gln Asp Asn Trp Leu Arg Thr Asn Trp Val Tyr Arg
 50                  55                  60
Gly Glu Ala Glu Arg Ile Phe Ile Glu Leu Lys Phe Thr Val Arg Asp
 65                  70                  75                  80
Cys Asn Ser Phe Pro Gly Gly Ala Ser Ser Cys Lys Glu Thr Phe Asn
                 85                  90                  95
Leu Tyr Tyr Ala Glu Ser Asp Leu Asp Tyr Gly Thr Asn Phe Gln Lys
            100                 105                 110
Arg Leu Phe Thr Lys Ile Asp Thr Ile Ala Pro Asp Glu Ile Thr Val
            115                 120                 125
Ser Ser Asp Phe Glu Ala Arg His Val Lys Leu Asn Val Glu Arg
130                 135                 140
Ser Val Gly Pro Leu Thr Arg Lys Gly Phe Tyr Leu Ala Phe Gln Asp
145                 150                 155                 160
Ile Gly Ala Cys Val Ala Leu Leu Ser Val Arg Val Tyr Tyr Lys Lys
                165                 170                 175
Cys Pro Glu Leu Leu Gln Gly Leu Ala His Phe Pro Glu Thr Ile Ala
            180                 185                 190
Gly Ser Asp Ala Pro Ser Leu Ala Thr Val Ala Gly Thr Cys Val Asp
            195                 200                 205
His Ala Val Val Pro Pro Gly Gly Glu Glu Pro Arg Met His Cys Ala
210                 215                 220
Val Asp Gly Glu Trp Leu Val Pro Ile Gly Gln Cys Leu Cys Gln Ala
225                 230                 235                 240
Gly Tyr Glu Lys Val Glu Asp Ala Cys Gln Ala Cys Ser Pro Gly Phe
                245                 250                 255
Phe Lys Phe Glu Ala Ser Glu Ser Pro Cys Leu Glu Cys Pro Glu His
            260                 265                 270
Thr Leu Pro Ser Pro Glu Gly Ala Thr Ser Cys Glu Cys Glu Glu Gly
            275                 280                 285
Phe Phe Arg Ala Pro Gln Asp Pro Ala Ser Met Pro Cys Thr Arg Pro
290                 295                 300
Pro Ser Ala Pro His Tyr Leu Thr Ala Val Gly Met Gly Ala Lys Val
305                 310                 315                 320
Glu Leu Arg Trp Thr Pro Pro Gln Asp Ser Gly Gly Arg Glu Asp Ile
                325                 330                 335
Val Tyr Ser Val Thr Cys Glu Gln Cys Trp Pro Glu Ser Gly Glu Cys
            340                 345                 350
Gly Pro Cys Glu Ala Ser Val Arg Tyr Ser Glu Pro Pro His Gly Leu
            355                 360                 365
Thr Arg Thr Ser Val Thr Val Ser Asp Leu Glu Pro His Met Asn Tyr
370                 375                 380
Thr Phe Thr Val Glu Ala Arg Asn Gly Val Ser Gly Leu Val Thr Ser
385                 390                 395                 400
Arg Ser Phe Arg Thr Ala Ser Val Ser Ile Asn Gln Thr Glu Pro Pro
                405                 410                 415
Lys Val Arg Leu Glu Gly Arg Ser Thr Thr Ser Leu Ser Val Ser Trp
            420                 425                 430
Ser Ile Pro Pro Pro Gln Gln Ser Arg Val Trp Lys Tyr Glu Val Thr
            435                 440                 445
```

-continued

```
Tyr Arg Lys Lys Gly Asp Ser Asn Ser Tyr Asn Val Arg Arg Thr Glu
        450                 455                 460
Gly Phe Ser Val Thr Leu Asp Asp Leu Ala Pro Asp Thr Thr Tyr Leu
465                 470                 475                 480
Val Gln Val Gln Ala Leu Thr Gln Glu Gly Gln Gly Ala Gly Ser Lys
                485                 490                 495
Val His Glu Phe Gln Thr Leu Ser Pro Glu Gly Ser Gly Asn Glu Pro
                500                 505                 510
Lys Ser Cys Asp Lys Thr His Thr Cys Pro Pro Cys Pro Ala Pro Glu
            515                 520                 525
Leu Leu Gly Gly Pro Ser Val Phe Leu Phe Pro Pro Lys Pro Lys Asp
        530                 535                 540
Thr Leu Met Ile Ser Arg Thr Pro Glu Val Thr Cys Val Val Val Asp
545                 550                 555                 560
Val Ser His Glu Asp Pro Glu Val Lys Phe Asn Trp Tyr Val Asp Gly
                565                 570                 575
Val Glu Val His Asn Ala Lys Thr Lys Pro Arg Glu Glu Gln Tyr Asn
                580                 585                 590
Ser Thr Tyr Arg Val Val Ser Val Leu Thr Val Leu His Gln Asp Trp
            595                 600                 605
Leu Asn Gly Lys Glu Tyr Lys Cys Lys Val Ser Asn Lys Ala Leu Pro
        610                 615                 620
Ala Pro Ile Glu Lys Thr Ile Ser Lys Ala Lys Gly Gln Pro Arg Glu
625                 630                 635                 640
Pro Gln Val Tyr Thr Leu Pro Pro Ser Arg Glu Glu Met Thr Lys Asn
                645                 650                 655
Gln Val Ser Leu Thr Cys Leu Val Lys Gly Phe Tyr Pro Ser Asp Ile
                660                 665                 670
Ala Val Glu Trp Glu Ser Asn Gly Gln Pro Glu Asn Asn Tyr Lys Thr
            675                 680                 685
Thr Pro Pro Val Leu Asp Ser Asp Gly Ser Phe Phe Leu Tyr Ser Lys
        690                 695                 700
Leu Thr Val Asp Lys Ser Arg Trp Gln Gln Gly Asn Val Phe Ser Cys
705                 710                 715                 720
Ser Val Met His Glu Ala Leu His Asn His Tyr Thr Gln Lys Ser Leu
                725                 730                 735
Ser Leu Ser Pro Gly Lys
                740
```